(12) United States Patent
Chou et al.

(10) Patent No.: US 8,282,914 B2
(45) Date of Patent: Oct. 9, 2012

(54) METHOD FOR TREATING ATHEROSCLEROSIS BY ADMINISTERING HUMAN MCP1 FUSIONS

(75) Inventors: Chuan-Chu Chou, Westfield, NJ (US); Loretta A. Bober, Linden, NJ (US); Lee Sullivan, Somerset, NJ (US)

(73) Assignee: Merck, Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/098,641

(22) Filed: May 2, 2011

(65) Prior Publication Data

US 2011/0206669 A1 Aug. 25, 2011

Related U.S. Application Data

(60) Continuation of application No. 12/621,228, filed on Nov. 18, 2009, now Pat. No. 7,972,591, which is a division of application No. 11/502,064, filed on Aug. 10, 2006, now Pat. No. 7,713,521.

(60) Provisional application No. 60/707,731, filed on Aug. 12, 2005.

(51) Int. Cl.
*A61K 38/19* (2006.01)
(52) U.S. Cl. ...................... 424/85.1; 514/21.2
(58) Field of Classification Search ................ None
See application file for complete search history.

(56) References Cited

U.S. PATENT DOCUMENTS

| | | | |
|---|---|---|---|
| 4,588,585 A | 5/1986 | Mark et al. |
| 4,751,180 A | 6/1988 | Cousens et al. |
| 5,098,833 A | 3/1992 | Lasky et al. |
| 5,116,964 A | 5/1992 | Capon et al. |
| 5,179,078 A | 1/1993 | Rollins et al. |
| 5,212,073 A | 5/1993 | Rollins et al. |
| 5,216,131 A | 6/1993 | Lasky et al. |
| 5,225,538 A | 7/1993 | Capon et al. |
| 5,278,287 A | 1/1994 | Rollins et al. |
| 5,359,046 A | 10/1994 | Capon et al. |
| 5,428,130 A | 6/1995 | Capon et al. |
| 5,455,165 A | 10/1995 | Capon et al. |
| 5,459,128 A | 10/1995 | Rollins et al. |
| 5,514,582 A | 5/1996 | Capon et al. |
| 5,532,144 A | 7/1996 | Yoshimura et al. |
| 5,571,713 A | 11/1996 | Lyle et al. |
| 5,605,671 A | 2/1997 | Lyle et al. |
| 5,705,360 A | 1/1998 | Rollins et al. |
| 5,714,147 A | 2/1998 | Capon et al. |
| 5,714,578 A | 2/1998 | Yoshimura et al. |
| 5,739,103 A | 4/1998 | Rollins et al. |
| 5,840,844 A | 11/1998 | Lasky et al. |
| 5,854,412 A | 12/1998 | Rollins et al. |
| 5,932,703 A | 8/1999 | Godiska et al. |
| 6,001,567 A | 12/1999 | Brow et al. |
| 6,090,795 A | 7/2000 | Yoshimura et al. |
| 6,403,782 B1 | 6/2002 | Luster et al. |
| 6,406,697 B1 | 6/2002 | Capon et al. |
| 6,485,910 B1 | 11/2002 | Walker et al. |
| 6,498,015 B1 | 12/2002 | Godiska et al. |
| 6,569,418 B1 | 5/2003 | Garzino-Demo et al. |
| 6,590,075 B2 | 7/2003 | Ruben et al. |
| 6,607,879 B1 | 8/2003 | Cocks et al. |
| 6,706,471 B1 | 3/2004 | Brow et al. |
| 6,737,513 B1 | 5/2004 | Gray et al. |
| 6,767,535 B1 | 7/2004 | Rollins et al. |
| 6,780,973 B1 | 8/2004 | Luster et al. |
| 6,780,982 B2 | 8/2004 | Lyamichev et al. |
| 6,787,645 B1 | 9/2004 | Rollins et al. |
| 6,869,924 B1 | 3/2005 | Yoshimura et al. |
| 6,878,687 B1 | 4/2005 | Ruben et al. |
| 2002/0009724 A1 | 1/2002 | Schlegel et al. |
| 2002/0009730 A1 | 1/2002 | Chenchik et al. |
| 2002/0137081 A1 | 9/2002 | Bandman |
| 2002/0198362 A1 | 12/2002 | Gaiger et al. |
| 2003/0073144 A1 | 4/2003 | Benson et al. |
| 2003/0078396 A1 | 4/2003 | Gaiger et al. |
| 2003/0099974 A1 | 5/2003 | Lillie et al. |
| 2003/0129214 A1 | 7/2003 | Bornstein et al. |
| 2003/0143220 A1 | 7/2003 | Capon et al. |
| 2003/0162737 A1 | 8/2003 | Egashira et al. |
| 2003/0166903 A1 | 9/2003 | Astromoff et al. |
| 2003/0175704 A1 | 9/2003 | Lasek et al. |
| 2004/0002068 A1 | 1/2004 | Gaiger et al. |
| 2004/0029179 A1 | 2/2004 | Koentgen |
| 2004/0031072 A1 | 2/2004 | La Rosa et al. |
| 2004/0077835 A1 | 4/2004 | Offord et al. |
| 2004/0110792 A1 | 6/2004 | Raponi |
| 2004/0157253 A1 | 8/2004 | Xu et al. |
| 2004/0177387 A1 | 9/2004 | Jayakrishna |
| 2004/0224875 A1 | 11/2004 | Schilling et al. |
| 2004/0248169 A1 | 12/2004 | Liew |
| 2004/0265808 A1 | 12/2004 | Garcia et al. |
| 2005/0058635 A1 | 3/2005 | Demuth et al. |
| 2005/0058639 A1 | 3/2005 | Gudas et al. |
| 2005/0232923 A1 | 10/2005 | Yan et al. |
| 2006/0263774 A1 | 11/2006 | Clark et al. |

FOREIGN PATENT DOCUMENTS

| | | |
|---|---|---|
| CA | 2152141 | 12/1996 |
| CA | 2343602 | 10/2001 |
| CN | 1144845 | 5/2000 |
| CN | 1435433 | 8/2003 |
| JP | 2003310272 | 11/2003 |
| JP | 2004307427 | 11/2004 |
| WO | WO90/07863 | 7/1990 |
| WO | WO92/19737 | 11/1992 |
| WO | WO95/04158 | 2/1995 |
| WO | WO95/09232 | 4/1995 |

(Continued)

OTHER PUBLICATIONS

The Merck Manual of Diagnosis and Therapy (1999), Beers and Berkow, 17th edition, pp. 1654-1658.*

(Continued)

*Primary Examiner* — Prema Mertz

(57) ABSTRACT

The present invention provides polypeptides including MCP1 fused, optionally, by a linker, to an immunoglobulin. Methods for using the polypeptides to treat medical disorders are also covered.

7 Claims, 1 Drawing Sheet

FOREIGN PATENT DOCUMENTS

| | | |
|---|---|---|
| WO | WO95/13295 | 5/1995 |
| WO | WO95/19167 | 7/1995 |
| WO | WO98/45435 | 10/1998 |
| WO | WO99/05297 | 2/1999 |
| WO | WO99/12968 | 3/1999 |
| WO | WO00/04926 | 2/2000 |
| WO | WO00/09525 | 2/2000 |
| WO | WO00/21991 | 4/2000 |
| WO | WO00/42071 | 7/2000 |
| WO | WO01/46697 | 6/2001 |
| WO | WO02/18413 | 3/2002 |
| WO | WO02/066510 | 8/2002 |
| WO | WO02/068579 | 9/2002 |
| WO | WO02/085308 | 10/2002 |
| WO | WO02/085309 | 10/2002 |
| WO | WO003/037376 | 5/2003 |
| WO | WO03/082920 | 10/2003 |
| WO | WO03/083059 | 10/2003 |
| WO | WO03/084993 | 10/2003 |
| WO | WO03/091391 | 11/2003 |
| WO | WO2004/022778 | 3/2004 |
| WO | WO2004/031233 | 4/2004 |
| WO | WO2004/065545 | 8/2004 |
| WO | WO2004/078777 | 9/2004 |
| WO | WO2004/080273 | 9/2004 |
| WO | WO2004/092368 | 10/2004 |
| WO | WO2004/096850 | 11/2004 |
| WO | WO2004/097052 | 11/2004 |
| WO | WO2004/112829 | 12/2004 |
| WO | WO2004/113522 | 12/2004 |
| WO | WO2005/002416 | 1/2005 |
| WO | WO2005/037305 | 4/2005 |
| WO | WO2007/113285 | 10/2007 |

OTHER PUBLICATIONS

Chintalacharuvu et al. Hybrid IgA2/IgG1 antibodies with tailor-made effector functions. Clin Immunol. Oct. 2001;101(1):21-31.

Esposito & Chatterjee. Enhancement of soluble protein expression through the use of fusion tags. Curr Opin Biotechnol. Aug. 2006;17(4):353-8.

Ferrara et al. Vascular endothelial growth factor is essential for corpus luteum angiogenesis. Nat Med. Mar. 1998;4(3):336-40.

Gerber et al. VEGF couples hypertrophic cartilage remodeling, ossification and angiogenesis during endochondral bone formation. Nat Med. Jun. 1999;5(6):623-8.

Hilbert et al. Pharmacokinetics ABS pharmacodynamics of BIWH 3 in healthy duffy antigen positive and duffy antigen negative male volunteers. Am. Soc. Clin. Pharm. Therap. 2006, PII-60.

Holash et al. VEGF-Trap: a VEGF blocker with potent antitumor effects. Proc Natl Acad Sci U S A. Aug. 20, 2002;99(17):11393-8.

Kurlander & Batker. The binding of human immunoglobulin G1 monomer and small, covalently cross-linked polymers of immunoglobulin G1 to human peripheral blood monocytes and polymorphonuclear leukocytes. J Clin Invest, Jan. 1982;69(1):1-8.

Ohtsuki et al. Detection of monocyte chemoattractant protein-1 receptor expression in experimental atherosclerotic lesions: an autoradiographic study. Circulation. Jul. 10, 2001;104(2):203-8.

Pashine et al. Failed efficacy of soluble human CD83-Ig in allogeneic mixed lymphocyte reactions and experimental autoimmune encephalomyelitis: Implications for a lack of therapeutic potential. Immunol Lett. Jan. 15, 2008;115(1):9-15. Epub Nov. 29, 2007.

Saphire et al, Contrasting IgG structures reveal extreme asymmetry and flexibility. J Mol Biol. May 24, 2002;319(1):9-18.

Terpe. Overview of tag protein fusions: from molecular and biochemical fundamentals to commercial systems. Appl Microbiol Biotechnol. Jan. 2003;60(5):523-33.

Unanue & Benacerraf. Textbook of Immunology (2d ed.). Williams & Wilkins, Baltimore/London, 1984. pp. 46-51.

Galimberti D, Bresolin N, Scarpini E., Chemokine network in multiple sclerosis: role in pathogenesis and targeting for future treatments, Expert Rev Neurother, May 2004;4(3):439-53.

Nigrovic PA, Lee DM Mast cells in inflammatory arthritis, Arthritis Res Ther, 2005:7(1):1-11, Epub Nov. 2, 2004.

Genbank accession No. BC025985 (released Mar. 22, 2002).

Genbank accession No. BC057688 (released Sep. 16, 2003).

Genbank accession No. NM_002982; derived from S71513.1 (released May 7, 1993).

Genbank accession No. NM_009915; derived from U56819.1 (released Sep. 12, 1996).

Genbank accession No. NM_006274; derived from AB000887.1 (released Jun. 6, 1997).

Genbank accession No. NP_002975; derived from AY766446.1 (released Oct. 1, 2005).

Genbank accession No. NP_006265; derived from AB000887.1 (released Jun. 6, 1997).

Genbank accession No. NP_954637; derived from BC031072.1 (released Jun. 13, 2002).

Brodmerkel, Carrie M., et al.; "Discovery and Pharmacological Characterizatin of a Novel Rodent-Active CCR2 Antagonist, INCB3344"; The Journal of Immunology; 175:5370-5378 (2005).

Chou, Chuan-Chu, et al.; "Pharmacological characterization of the chemokine receptor, hCCR1 in a stable transfectant and differentiated HL-60 cells: antagonism of hCCR1 activation by MIP-1β"; British Journal of Pharmacology; 137:663-675 (2002).

Conti, Ilaria, et al.; "CCL2 (monocyte chemoattractant protein-1) and cancer"; Seminars in Cancer Biology; 14:149-154 (2004).

Elhofy, Adam, et al.; "Transgenic expression of CCL2 in the central nervous system prevents experimental autoimmune encephalomyelitis"; Journal of Leukocyte Biology; 77:229-237 (2005).

Fan, Xuedong, et al.; "Molecular cloning of a gene selectively induced by gamma interferon from human macrophage cell line U937"; Mol. Cell. Biol.; 9(5):1922-1928 (1989).

Grewal, Iqbal S., et al.; "Transgenic Monocyte Chemoattractant Protein-1 (MCP-1) in Pancreatic Islets Produces Monocyte-Rich Insulitis Without Diabetes"; The Journal of Immunology; 159:401-408 (1997).

Gu, Long, et al.; "In vivo properties of monocyte chemoattractant protein-1"; Journal of Leukocyte Biology; 62:577-580 (1997).

Gu, Long, et al.; "Control of $T_H2$ polarization by the chemokine monocyte chemoattractant protein-1"; Nature; 404:407-411 (2000).

Jefferis, Roy, et al.; "Interaction sites on human IgG-Fc for FegammaR: current models"; Immunol Lett.; 82(1-2):57-65 (2002).

Kennedy, Kevin, J., et al.; "Acute and relapsing experimental autoimmune encephalomyelitis are regulated by differential expression of the CC chemokines macrophage inflammatory protein-1α and monocyte chemotactic protein-1"; Journal of Neuroimmunology; 92:98-108 (1998).

Lu, Bao, et al.; "Abnormalities in Monocyte Recruitment and Cytokine Expression in Monocyte Chemoattractant Protein 1-deficient Mice"; Journal Exp. Med.; 187(4):601-608 (1998).

Neels, Jaap G., et al.; "Inflamed fat: what starts the fire?"; The Journal of Clinical Investigation; 116(1):33-35 (2006).

Sartipy, Peter, et al.; "Monocyte chemoattractant protein 1 in obesity and insulin resistance"; PNAS; 100(12):7265-7270 (2003).

Weisberg, Stuart P., et al.; "CCR2 modulates inflammatory and metabolic effects of high-fat feeding"; The Journal of Clinical Investigation; 116(1):115-124 (2006).

Xu, Yuanyuan, et al.; "Residue at position 331 in the IgG1 and IgG4 CH2 domains contributes to their differential ability to bind and activate complement"; J Biol Chem.; 269(5):3469-3474 (1994).

Yoshimura, Teizo el al.; << Human monocyte chemoattractant protein-1 (MCP-1). Full-length cDNA cloning, expression in mitogen-stimulated blood mononuclear leukocytes, and sequence similarity to mouse competence gene JE; FEBS Lett.; 244(2):487-493 (1989).

Zijlmans, H. Imaa, et al.; "The absence of CCL2 expression in cervical carcinoma is associated with increased survival and loss of heterozygosity at 17q11.2", Journal of Pathology; 208:507-517 (2006).

Charo, Israel F., et al., Chemokines in the Pathogenesis of Vascular Disease, Journal of the American Heart Association, 95:858-866 (2004).

Francis, G.E., et al., PEGylation of cytokines and other therapeutic proteins and peptides: the importance of biological optimisation of coupling techniques, International Journal of Hematology, 68:1-18 (1998).

Huang, Deren, et al., Absence of Monocyte Chemoattractant Protein 1 in Mice Leads to Decreased Local Macrophage Recruitment and Antigen-specific T Helper Cell Type 1 immune Response in Experimental Autoimmune Encephalomyelitis, Journal of Exp. Med., 193(6):713-725 (2001).

Izikson, Leonid, et al., Resistance to Experimental Autoimmune Encephalomyelitis in Mice Lacking the CC Chemokine Receptor $(CCR)^2$, Journal of Exp. Med., 192(7):1075-1080 (2000).

Krautwald, Stefan, et al., Ectopic expression of CCL19 impairs alloimmune response in mice, Immunology, 112:301-309 (2004).

Mahad, Don J., et al., The role of MCP-1 (CCL2) and CCR2 in multiple sclerosis and experimental autoimmune encephalomyelitis (EAE), Seminars in Immunology, 15:23-32 (2003).

Quinones, Marlon P., et al., Experimental arthritis in CC chemokine receptor 2-null mice closely mimics severe human rheumatoid arthritis, The Journal of Clinical Investigation, 113(6):856-866 (2004).

International Search Report, International Application No. PCT/US2006/031155, Date of Mailing Dec. 12, 2006.

Genbank record No. NM_000648. *Homo sapiens* chemokine (C-C motif) receptor 2 (CCR2), transcript variant B, mRNA. Mar. 15, 2009.

Gu L, Okada Y, Clinton SK, Gerard C, Sukhova GK, Libby P, Rollins BJ. Absence of monocyte chemoattractant protein-1 reduces atherosclerosis in low density lipoprotein receptor-deficient mice. Mol Cell. Aug. 1998;2(2):275-81.

Taub DD. Chemokine-leukocyte interactions. The voodoo that they do so well.Cytokine Growth Factor Rev. Dec. 1996;7(4):355-76. Review.

* cited by examiner

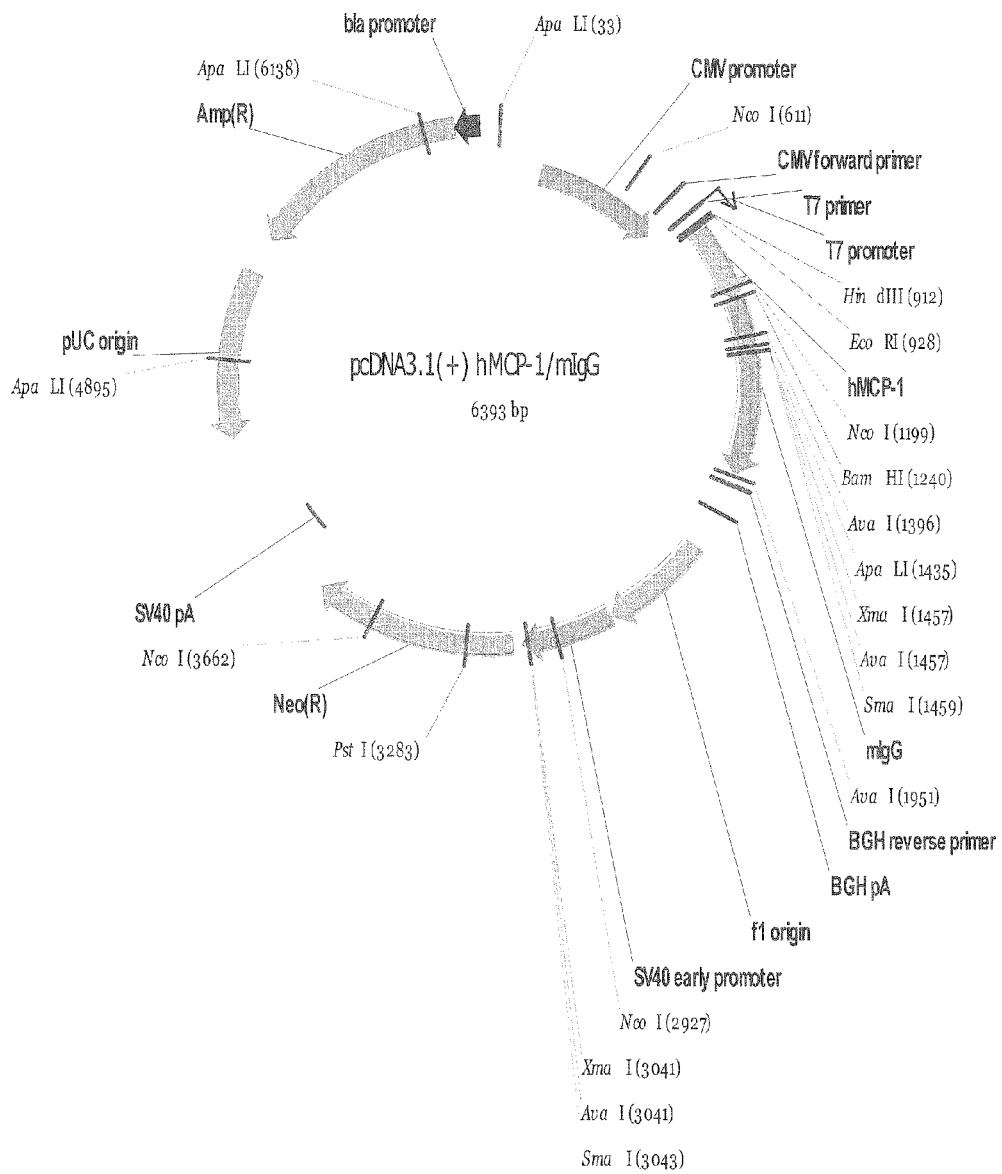

SEQUENCE LISTING

```
<160> NUMBER OF SEQ ID NOS: 30

<210> SEQ ID NO 1
<211> LENGTH: 99
<212> TYPE: PRT
<213> ORGANISM: Homo sapiens

<400> SEQUENCE: 1

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 2
<211> LENGTH: 76
<212> TYPE: PRT
<213> ORGANISM: Homo sapiens

<400> SEQUENCE: 2

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45
```

Lys Glu Ile Cys Ala Asp Pro Lys Gln Lys Trp Val Gln Asp Ser Met
            50                  55                  60

Asp His Leu Asp Lys Gln Thr Gln Thr Pro Lys Thr
65                  70                  75

<210> SEQ ID NO 3
<211> LENGTH: 227
<212> TYPE: PRT
<213> ORGANISM: Artificial Sequence
<220> FEATURE:
<223> OTHER INFORMATION: mature polypeptide sequence of mouse
      immunoglobulin heavy chain constant region (hinge to CH3 only),
      isotype gamma 1

<400> SEQUENCE: 3

Val Pro Arg Asp Cys Gly Cys Lys Pro Cys Ile Cys Thr Val Pro Glu
1               5                   10                  15

Val Ser Ser Val Phe Ile Phe Pro Pro Lys Pro Lys Asp Val Leu Thr
                20                  25                  30

Ile Thr Leu Thr Pro Lys Val Thr Cys Val Val Val Asp Ile Ser Lys
            35                  40                  45

Asp Asp Pro Glu Val Gln Phe Ser Trp Phe Val Asp Asp Val Glu Val
        50                  55                  60

His Thr Ala Gln Thr Lys Pro Arg Glu Glu Gln Phe Asn Ser Thr Phe
65                  70                  75                  80

Arg Ser Val Ser Glu Leu Pro Ile Met His Gln Asp Trp Leu Asn Gly
                85                  90                  95

Lys Glu Phe Lys Cys Arg Val Asn Ser Ala Ala Phe Pro Ala Pro Ile
            100                 105                 110

Glu Lys Thr Ile Ser Lys Thr Lys Gly Arg Pro Lys Ala Pro Gln Val
        115                 120                 125

Tyr Thr Ile Pro Pro Pro Lys Glu Gln Met Ala Lys Asp Lys Val Ser
    130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Asp Thr Asp Gly Ser Tyr Phe Val Tyr Ser Lys Leu Asn Val
            180                 185                 190

Gln Lys Ser Asn Trp Glu Ala Gly Asn Thr Phe Thr Cys Ser Val Leu
        195                 200                 205

His Glu Gly Leu His Asn His Thr Glu Lys Ser Leu Ser His Ser
    210                 215                 220

Pro Gly Lys
225

<210> SEQ ID NO 4
<211> LENGTH: 229
<212> TYPE: PRT
<213> ORGANISM: Artificial Sequence
<220> FEATURE:
<223> OTHER INFORMATION: human immunoglobulin heavy chain constant
      region (hinge to CH3 only), isotype gamma 4

<400> SEQUENCE: 4

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

```
Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys
225

<210> SEQ ID NO 5
<211> LENGTH: 229
<212> TYPE: PRT
<213> ORGANISM: Artificial Sequence
<220> FEATURE:
<223> OTHER INFORMATION: human immunoglobulin heavy chain constant
      region (hinge to CH3 only), isotype gamma 4 monomeric variant

<400> SEQUENCE: 5

Glu Ser Lys Tyr Gly Pro Pro Ser Pro Ser Pro Ala Pro Glu Phe
1                5                  10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160
```

-continued

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 6
<211> LENGTH: 233
<212> TYPE: PRT
<213> ORGANISM: Artificial Sequence
<220> FEATURE:
<223> OTHER INFORMATION: human immunoglobulin heavy chain constant
      region (hinge to CH3 only), isotype gamma 1

<400> SEQUENCE: 6

Val Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 7
<211> LENGTH: 233
<212> TYPE: PRT
<213> ORGANISM: Artificial Sequence
<220> FEATURE:
<223> OTHER INFORMATION: human immunoglobulin heavy chain constant
      region (hinge to CH3 only), isotype gamma 1 monomeric variant -continued

<400> SEQUENCE: 7

```
Val Glu Pro Lys Ser Ser Asp Lys Thr His Thr Ser Pro Pro Ser Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230
```

<210> SEQ ID NO 8
<211> LENGTH: 305
<212> TYPE: PRT
<213> ORGANISM: Artificial Sequence
<220> FEATURE:
<223> OTHER INFORMATION: human MCP-1 fused to mouse IgG1

<400> SEQUENCE: 8

```
Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Lys Thr Gly Ser Val Pro
65                  70                  75                  80

Arg Asp Cys Gly Cys Lys Pro Cys Ile Cys Thr Val Pro Glu Val Ser
                85                  90                  95

Ser Val Phe Ile Phe Pro Pro Lys Pro Lys Asp Val Leu Thr Ile Thr
            100                 105                 110

Leu Thr Pro Lys Val Thr Cys Val Val Val Asp Ile Ser Lys Asp Asp
        115                 120                 125
```

```
Pro Glu Val Gln Phe Ser Trp Phe Val Asp Asp Val Glu Val His Thr
    130                 135                 140

Ala Gln Thr Lys Pro Arg Glu Glu Gln Phe Asn Ser Thr Phe Arg Ser
145                 150                 155                 160

Val Ser Glu Leu Pro Ile Met His Gln Asp Trp Leu Asn Gly Lys Glu
                165                 170                 175

Phe Lys Cys Arg Val Asn Ser Ala Ala Phe Pro Ala Pro Ile Glu Lys
            180                 185                 190

Thr Ile Ser Lys Thr Lys Gly Arg Pro Lys Ala Pro Gln Val Tyr Thr
        195                 200                 205

Ile Pro Pro Pro Lys Glu Gln Met Ala Lys Asp Lys Val Ser Leu Thr
    210                 215                 220

Cys Met Ile Thr Asp Phe Phe Pro Glu Asp Ile Thr Val Glu Trp Gln
225                 230                 235                 240

Trp Asn Gly Gln Pro Ala Glu Asn Tyr Lys Asn Thr Gln Pro Ile Met
                245                 250                 255

Asp Thr Asp Gly Ser Tyr Phe Val Tyr Ser Lys Leu Asn Val Gln Lys
            260                 265                 270

Ser Asn Trp Glu Ala Gly Asn Thr Phe Thr Cys Ser Val Leu His Glu
        275                 280                 285

Gly Leu His Asn His His Thr Glu Lys Ser Leu Ser His Ser Pro Gly
    290                 295                 300

Lys
305

<210> SEQ ID NO 9
<211> LENGTH: 307
<212> TYPE: PRT
<213> ORGANISM: Artificial Sequence
<220> FEATURE:
<223> OTHER INFORMATION: mature human MCP-1 fused to human IgG4

<400> SEQUENCE: 9

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr Gly Ser Glu Ser
65                  70                  75                  80

Lys Tyr Gly Pro Pro Cys Pro Ser Cys Pro Ala Pro Glu Phe Leu Gly
                85                  90                  95

Gly Pro Ser Val Phe Leu Phe Pro Pro Lys Pro Lys Asp Thr Leu Met
            100                 105                 110

Ile Ser Arg Thr Pro Glu Val Thr Cys Val Val Val Asp Val Ser Gln
        115                 120                 125

Glu Asp Pro Glu Val Gln Phe Asn Trp Tyr Val Asp Gly Val Glu Val
    130                 135                 140

His Asn Ala Lys Thr Lys Pro Arg Glu Glu Gln Phe Asn Ser Thr Tyr
145                 150                 155                 160

Arg Val Val Ser Val Leu Thr Val Leu His Gln Asp Trp Leu Asn Gly
                165                 170                 175
```

```
Lys Glu Tyr Lys Cys Lys Val Ser Asn Lys Gly Leu Pro Ser Ser Ile
                180                 185                 190

Glu Lys Thr Ile Ser Lys Ala Lys Gly Gln Pro Arg Glu Pro Gln Val
            195                 200                 205

Tyr Thr Leu Pro Pro Ser Gln Glu Glu Met Thr Lys Asn Gln Val Ser
210                 215                 220

Leu Thr Cys Leu Val Lys Gly Phe Tyr Pro Ser Asp Ile Ala Val Glu
225                 230                 235                 240

Trp Glu Ser Asn Gly Gln Pro Glu Asn Asn Tyr Lys Thr Thr Pro Pro
                245                 250                 255

Val Leu Asp Ser Asp Gly Ser Phe Phe Leu Tyr Ser Arg Leu Thr Val
            260                 265                 270

Asp Lys Ser Arg Trp Gln Glu Gly Asn Val Phe Ser Cys Ser Val Met
        275                 280                 285

His Glu Ala Leu His Asn His Tyr Thr Gln Lys Ser Leu Ser Leu Ser
    290                 295                 300

Leu Gly Lys
305

<210> SEQ ID NO 10
<211> LENGTH: 307
<212> TYPE: PRT
<213> ORGANISM: Artificial Sequence
<220> FEATURE:
<223> OTHER INFORMATION: mature  human MCP-1 fused to human IgG4
      monomeric variant

<400> SEQUENCE: 10

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
                20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Lys Thr Gly Ser Glu Ser
65                  70                  75                  80

Lys Tyr Gly Pro Pro Ser Pro Ser Ser Pro Ala Pro Glu Phe Leu Gly
                85                  90                  95

Gly Pro Ser Val Phe Leu Phe Pro Pro Lys Pro Lys Asp Thr Leu Met
            100                 105                 110

Ile Ser Arg Thr Pro Glu Val Thr Cys Val Val Val Asp Val Ser Gln
            115                 120                 125

Glu Asp Pro Glu Val Gln Phe Asn Trp Tyr Val Asp Gly Val Glu Val
            130                 135                 140

His Asn Ala Lys Thr Lys Pro Arg Glu Glu Gln Phe Asn Ser Thr Tyr
145                 150                 155                 160

Arg Val Val Ser Val Leu Thr Val Leu His Gln Asp Trp Leu Asn Gly
                165                 170                 175

Lys Glu Tyr Lys Cys Lys Val Ser Asn Lys Gly Leu Pro Ser Ser Ile
                180                 185                 190

Glu Lys Thr Ile Ser Lys Ala Lys Gly Gln Pro Arg Glu Pro Gln Val
            195                 200                 205

Tyr Thr Leu Pro Pro Ser Gln Glu Glu Met Thr Lys Asn Gln Val Ser
210                 215                 220
```

```
Leu Thr Cys Leu Val Lys Gly Phe Tyr Pro Ser Asp Ile Ala Val Glu
225                 230                 235                 240

Trp Glu Ser Asn Gly Gln Pro Glu Asn Asn Tyr Lys Thr Thr Pro Pro
            245                 250                 255

Val Leu Asp Ser Asp Gly Ser Phe Phe Leu Tyr Ser Arg Leu Thr Val
        260                 265                 270

Asp Lys Ser Arg Trp Gln Glu Gly Asn Val Phe Ser Cys Ser Val Met
    275                 280                 285

His Glu Ala Leu His Asn His Tyr Thr Gln Lys Ser Leu Ser Leu Ser
290                 295                 300

Leu Gly Lys
305

<210> SEQ ID NO 11
<211> LENGTH: 311
<212> TYPE: PRT
<213> ORGANISM: Artificial Sequence
<220> FEATURE:
<223> OTHER INFORMATION: mature human MCP-1 fused to human IgG1

<400> SEQUENCE: 11

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Lys Thr Gly Ser Val Glu
65                  70                  75                  80

Pro Lys Ser Cys Asp Lys Thr His Thr Cys Pro Pro Cys Pro Ala Pro
                85                  90                  95

Glu Leu Leu Gly Gly Pro Ser Val Phe Leu Phe Pro Pro Lys Pro Lys
            100                 105                 110

Asp Thr Leu Met Ile Ser Arg Thr Pro Glu Val Thr Cys Val Val Val
        115                 120                 125

Asp Val Ser His Glu Asp Pro Glu Val Lys Phe Asn Trp Tyr Val Asp
    130                 135                 140

Gly Val Glu Val His Asn Ala Lys Thr Lys Pro Arg Glu Glu Gln Tyr
145                 150                 155                 160

Asn Ser Thr Tyr Arg Val Val Ser Val Leu Thr Val Leu His Gln Asp
                165                 170                 175

Trp Leu Asn Gly Lys Glu Tyr Lys Cys Lys Val Ser Asn Lys Ala Leu
            180                 185                 190

Pro Ala Pro Ile Glu Lys Thr Ile Ser Lys Ala Lys Gly Gln Pro Arg
        195                 200                 205

Glu Pro Gln Val Tyr Thr Leu Pro Pro Ser Arg Asp Glu Leu Thr Lys
    210                 215                 220

Asn Gln Val Ser Leu Thr Cys Leu Val Lys Gly Phe Tyr Pro Ser Asp
225                 230                 235                 240

Ile Ala Val Glu Trp Glu Ser Asn Gly Gln Pro Glu Asn Asn Tyr Lys
                245                 250                 255

Thr Thr Pro Pro Val Leu Asp Ser Asp Gly Ser Phe Phe Leu Tyr Ser
            260                 265                 270
```

Lys Leu Thr Val Asp Lys Ser Arg Trp Gln Gln Gly Asn Val Phe Ser
        275                 280                 285

Cys Ser Val Met His Glu Ala Leu His Asn His Tyr Thr Gln Lys Ser
    290                 295                 300

Leu Ser Leu Ser Pro Gly Lys
305                 310

<210> SEQ ID NO 12
<211> LENGTH: 311
<212> TYPE: PRT
<213> ORGANISM: Artificial Sequence
<220> FEATURE:
<223> OTHER INFORMATION: human MCP-1 fused to human IgG1 monomeric
      variant

<400> SEQUENCE: 12

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Lys Thr Gly Ser Val Glu
65                  70                  75                  80

Pro Lys Ser Ser Asp Lys Thr His Thr Ser Pro Pro Ser Pro Ala Pro
                85                  90                  95

Glu Leu Leu Gly Gly Pro Ser Val Phe Leu Phe Pro Pro Lys Pro Lys
            100                 105                 110

Asp Thr Leu Met Ile Ser Arg Thr Pro Glu Val Thr Cys Val Val Val
        115                 120                 125

Asp Val Ser His Glu Asp Pro Glu Val Lys Phe Asn Trp Tyr Val Asp
    130                 135                 140

Gly Val Glu Val His Asn Ala Lys Thr Lys Pro Arg Glu Glu Gln Tyr
145                 150                 155                 160

Asn Ser Thr Tyr Arg Val Val Ser Val Leu Thr Val Leu His Gln Asp
                165                 170                 175

Trp Leu Asn Gly Lys Glu Tyr Lys Cys Lys Val Ser Asn Lys Ala Leu
            180                 185                 190

Pro Ala Pro Ile Glu Lys Thr Ile Ser Lys Ala Lys Gly Gln Pro Arg
        195                 200                 205

Glu Pro Gln Val Tyr Thr Leu Pro Pro Ser Arg Asp Glu Leu Thr Lys
    210                 215                 220

Asn Gln Val Ser Leu Thr Cys Leu Val Lys Gly Phe Tyr Pro Ser Asp
225                 230                 235                 240

Ile Ala Val Glu Trp Glu Ser Asn Gly Gln Pro Glu Asn Asn Tyr Lys
                245                 250                 255

Thr Thr Pro Pro Val Leu Asp Ser Asp Gly Ser Phe Phe Leu Tyr Ser
            260                 265                 270

Lys Leu Thr Val Asp Lys Ser Arg Trp Gln Gln Gly Asn Val Phe Ser
        275                 280                 285

Cys Ser Val Met His Glu Ala Leu His Asn His Tyr Thr Gln Lys Ser
    290                 295                 300

Leu Ser Leu Ser Pro Gly Lys
305                 310

<210> SEQ ID NO 13
<211> LENGTH: 300
<212> TYPE: DNA
<213> ORGANISM: Homo sapiens

<400> SEQUENCE: 13

```
atgaaagtct ctgccgccct tctgtgcctg ctgctcatag cagccacctt cattccccaa    60
gggctcgctc agccagatgc aatcaatgcc ccagtcacct gctgttataa cttcaccaat   120
aggaagatct cagtgcagag gctcgcgagc tatagaagaa tcaccagcag caagtgtccc   180
aaagaagctg tgatcttcaa gaccattgtg gccaaggaga tctgtgctga ccccaagcag   240
aagtgggttc aggattccat ggaccacctg gacaagcaaa cccaaactcc gaagacttga   300
```

<210> SEQ ID NO 14
<211> LENGTH: 684
<212> TYPE: DNA
<213> ORGANISM: Artificial Sequence
<220> FEATURE:
<223> OTHER INFORMATION: mouse heavy-chain immunoglobulin constant
      region, gamma 1 isotype, starting from the amino terminus of the
      hinge region and ending at the carboxy-terminus of the CH3 region

<400> SEQUENCE: 14

```
gtgcccaggg attgtggttg taagccttgc atatgtacag tcccagaagt atcatctgtc    60
ttcatcttcc ccccaaagcc caaggatgtg ctcaccatta ctctgactcc taaggtcacg   120
tgtgttgtgg tagacatcag caaggatgat cccgaggtcc agttcagctg gtttgtagat   180
gatgtggagt gcacacagc tcagacaaaa ccccgggagg agcagttcaa cagcactttc   240
cgttcagtca gtgaacttcc catcatgcac caggactggc tcaatggcaa ggagttcaaa   300
tgcagggtca acagtgcagc tttccctgcc ccatcgaga aaaccatctc caaaaccaaa   360
ggcagaccga aggctccaca ggtgtacacc attccacctc ccaaggagca gatggccaag   420
gataaagtca gtctgacctg catgataaca gacttcttcc ctgaagacat tactgtggag   480
tggcagtgga atgggcagcc agcggagaac tacaagaaca ctcagcccat catggacaca   540
gatggctctt acttcgtcta cagcaagctc aatgtgcaga gagcaactg ggaggcagga   600
aatactttca cctgctctgt gttacatgag ggcctgcaca ccaccatac tgagaagagc   660
ctctccccact ctcctggtaa atga                                        684
```

<210> SEQ ID NO 15
<211> LENGTH: 690
<212> TYPE: DNA
<213> ORGANISM: Artificial Sequence
<220> FEATURE:
<223> OTHER INFORMATION: human heavy-chain immunoglobulin constant
      region, gamma 4 isotype, starting from the amino terminus of the
      hinge region and ending at the carboxy-terminus of the CH3 region

<400> SEQUENCE: 15

```
gagtccaaat atggtccccc atgcccatca tgcccagcac ctgagttcct ggggggacca    60
tcagtcttcc tgttcccccc aaaacccaag gacactctca tgatctcccg gacccctgag   120
gtcacgtgcg tggtggtgga cgtgagccag gaagacccg aggtccagtt caactggtac   180
gtggatggcg tggaggtgca taatgccaag acaaagccgc gggaggagca gttcaacagc   240
acgtaccgtg tggtcagcgt cctcaccgtc ctgcaccagg actggctgaa cggcaaggag   300
tacaagtgca aggtctccaa caaaggcctc ccgtcctcca tcgagaaaac catctccaaa   360
gccaaagggc agccccgaga gccacaggtg tacaccctgc ccccatccca ggaggagatg   420
accaagaacc aggtcagcct gacctgcctg gtcaaaggct tctaccccag cgacatcgcc   480
```

```
gtggagtggg agagcaatgg gcagccggag aacaactaca agaccacgcc tcccgtgctg    540
gactccgacg gctccttctt cctctacagc aggctaaccg tggacaagag caggtggcag    600
gaggggaatg tcttctcatg ctccgtgatg catgaggctc tgcacaacca ctacacacag    660
aagagcctct ccctgtctct gggtaaatga                                     690
```

<210> SEQ ID NO 16
<211> LENGTH: 690
<212> TYPE: DNA
<213> ORGANISM: Artificial Sequence
<220> FEATURE:
<223> OTHER INFORMATION: human heavy-chain immunoglobulin constant
      region, gamma 4 isotype, monomeric variant, starting from the
      amino terminus of the hinge region and ending at the carboxy-
      terminus of the CH3 region

<400> SEQUENCE: 16

```
gagtccaaat atggtccccc atctccatca tctccagcac ctgagttcct gggggggacca    60 tcagtcttcc tgttcccccc aaaacccaag gacactctca tgatctcccg acccctgag    120 gtcacgtgcg tggtggtgga cgtgagccag gaagacccg aggtccagtt caactggtac    180
gtggatggcg tggaggtgca taatgccaag acaaagccgc gggaggagca gttcaacagc    240
acgtaccgtg tggtcagcgt cctcaccgtc ctgcaccagg actggctgaa cggcaaggag    300
tacaagtgca aggtctccaa caaaggcctc ccgtcctcca tcgagaaaac catctccaaa    360 gccaagggc agccccgaga gccacaggtg tacaccctgc cccatccca ggaggagatg     420 accaagaacc aggtcagcct gacctgcctg gtcaaaggct tctacccag cgacatcgcc    480 gtggagtggg agagcaatgg gcagccggag aacaactaca agaccacgcc tcccgtgctg    540
gactccgacg gctccttctt cctctacagc aggctaaccg tggacaagag caggtggcag    600
gaggggaatg tcttctcatg ctccgtgatg catgaggctc tgcacaacca ctacacacag    660
aagagcctct ccctgtctct gggtaaatga                                     690
```

<210> SEQ ID NO 17
<211> LENGTH: 702
<212> TYPE: DNA
<213> ORGANISM: Artificial Sequence
<220> FEATURE:
<223> OTHER INFORMATION: human heavy-chain immunoglobulin constant
      region, gamma 1 isotype, starting from the amino terminus of the
      hinge region and ending at the carboxy-terminus of the CH3 region

<400> SEQUENCE: 17

```
gttgagccca aatcttgtga caaaactcac acatgcccac cgtgcccagc acctgaactc    60 ctgggggac cgtcagtctt cctcttcccc ccaaaaccca aggacaccct catgatctcc    120
cggacccctg aggtcacatg cgtggtggtg gacgtgagcc acgaagaccc tgaggtcaag    180
ttcaactggt acgtggacgg cgtggaggtg cataatgcca agacaaagcc gcggaggag    240 cagtacaaca gcacgtaccg tgtggtcagc gtcctcaccg tcctgcacca ggactggctg    300
aatggcaagg agtacaagtg caaggtctcc aacaaagccc tcccagcccc catcgagaaa    360
accatctcca aagccaaagg gcagcccga gaaccacagg tgtacaccct gcccccatcc    420
cgggatgagc tgaccaagaa ccaggtcagc ctgacctgcc tggtcaaagg cttctatccc    480
agcgacatcg ccgtggagtg ggagagcaat gggcagccgg agaacaacta caagaccacg    540
cctcccgtgc tggactccga cggctccttc ttcctctaca gcaagctcac cgtggacaag    600
agcaggtggc agcaggggaa cgtcttctca tgctccgtga tgcatgaggc tctgcacaac    660
cactacacgc agaagagcct ctccctgtct ccgggtaaat ga                       702
```

```
<210> SEQ ID NO 18
<211> LENGTH: 702
<212> TYPE: DNA
<213> ORGANISM: Artificial Sequence
<220> FEATURE:
<223> OTHER INFORMATION: human heavy-chain immunoglobulin constant
      region, gamma 1 isotype, monomeric variant, starting from the
      amino terminus of the hinge region and ending at the carboxy-
      terminus of the CH3 region

<400> SEQUENCE: 18
gttgagccca aatcttctga caaaactcac acatctccac cgtctccagc acctgaactc      60 ctgggggac  cgtcagtctt cctcttcccc ccaaaaccca aggacaccct catgatctcc    120 cggaccctg  aggtcacatg cgtggtggtg gacgtgagcc acgaagaccc tgaggtcaag    180
ttcaactggt acgtggacgg cgtggaggtg cataatgcca agacaaagcc gcgggaggag    240
cagtacaaca gcacgtaccg tgtggtcagc gtcctcaccg tcctgcacca ggactggctg    300
aatggcaagg agtacaagtg caaggtctcc aacaaagccc tcccagcccc catcgagaaa    360
accatctcca aagccaaagg gcagccccga gaaccacagg tgtacaccct gcccccatcc    420
cgggatgagc tgaccaagaa ccaggtcagc ctgacctgcc tggtcaaagg cttctatccc    480
agcgacatcg ccgtggagtg ggagagcaat gggcagccgg agaacaacta caagaccacg    540
cctcccgtgc tggactccga cggctccttc ttcctctaca gcaagctcac cgtggacaag    600
agcaggtggc agcaggggaa cgtcttctca tgctccgtga tgcatgaggc tctgcacaac    660
cactacacgc agaagagcct ctccctgtct ccgggtaaat ga                       702

<210> SEQ ID NO 19
<211> LENGTH: 987
<212> TYPE: DNA
<213> ORGANISM: Artificial Sequence
<220> FEATURE:
<223> OTHER INFORMATION: human MCP-1 (including the leader peptide)
      fused to mouse IgG1

<400> SEQUENCE: 19
atgaaagtct ctgccgccct tctgtgcctg ctgctcatag cagccacctt cattccccaa      60
gggctcgctc agccagatgc aatcaatgcc ccagtcacct gctgttataa cttcaccaat    120
aggaagatct cagtgcagag gctcgcgagc tatagaagaa tcaccagcag caagtgtccc    180
aaagaagctg tgatcttcaa gaccattgtg gccaaggaga tctgtgctga ccccaagcag    240
aagtgggttc aggattccat ggaccacctg gacaagcaaa cccaaactcc gaagactgga    300
tccgtgccca gggattgtgg ttgtaagcct tgcatatgta cagtcccaga agtatcatct    360
gtcttcatct ccccccaaa  gcccaaggat gtgctcacca ttactctgac tcctaaggtc    420
acgtgtgttg tggtagacat cagcaaggat gatcccgagg tccagttcag ctggtttgta    480
gatgatgtgg aggtgcacac agctcagaca aaacccggg  aggagcagtt caacagcact    540
ttccgttcag tcagtgaact tcccatcatg caccaggact ggctcaatgg caaggagttc    600
aaatgcaggg tcaacagtgc agctttccct gcccccatcg agaaaaccat ctccaaaacc    660
aaaggcagac cgaaggctcc acaggtgtac accattccac ctcccaagga gcagatggcc    720
aaggataaag tcagtctgac ctgcatgata acagacttct tccctgaaga cattactgtg    780
gagtggcagt ggaatgggca gccagcggag aactacaaga cactcagcc  catcatggac    840 acagatggct cttacttcgt ctacagcaag ctcaatgtgc agaagagcaa ctgggaggca    900
ggaaatactt tcacctgctc tgtgttacat gagggcctgc acaaccacca tactgagaag    960
agcctctccc actctcctgg taaatga                                        987
```

```
<210> SEQ ID NO 20
<211> LENGTH: 993
<212> TYPE: DNA
<213> ORGANISM: Artificial Sequence
<220> FEATURE:
<223> OTHER INFORMATION: human MCP-1 (including the leader peptide)
      fused to human IgG4

<400> SEQUENCE: 20
atgaaagtct ctgccgccct tctgtgcctg ctgctcatag cagccacctt cattccccaa      60
gggctcgctc agccagatgc aatcaatgcc ccagtcacct gctgttataa cttcaccaat     120
aggaagatct cagtgcagag gctcgcgagc tatagaagaa tcaccagcag caagtgtccc     180
aaagaagctg tgatcttcaa gaccattgtg gccaaggaga tctgtgctga ccccaagcag     240
aagtgggttc aggattccat ggaccaccty gacaagcaaa cccaaactcc gaagactgga     300
tccgagtcca aatatggtcc cccatgccca tcatgcccag cacctgagtt cctgggggga     360
ccatcagtct tcctgttccc cccaaaaccc aaggacactc tcatgatctc ccggacccct     420
gaggtcacgt gcgtggtggt ggacgtgagc caggaagacc ccgaggtcca gttcaactgg     480
tacgtggatg gcgtggaggt gcataatgcc aagacaaagc cgcgggagga gcagttcaac     540
agcacgtacc gtgtggtcag cgtcctcacc gtcctgcacc aggactggct gaacggcaag     600
gagtacaagt gcaaggtctc caacaaaggc ctcccgtcct ccatcgagaa aaccatctcc     660
aaagccaaag ggcagccccg agagccacag gtgtacaccc tgcccccatc ccaggaggag     720
atgaccaaga accaggtcag cctgacctgc ctggtcaaag gcttctaccc cagcgacatc     780
gccgtggagt gggagagcaa tgggcagccg gagaacaact acaagaccac gcctcccgtg     840
ctggactccg acggctcctt cttcctctac agcaggctaa ccgtggacaa gagcaggtgg     900
caggagggga atgtcttctc atgctccgtg atgcatgagg ctctgcacaa ccactacaca     960
cagaagagcc tctccctgtc tctgggtaaa tga                                  993

<210> SEQ ID NO 21
<211> LENGTH: 993
<212> TYPE: DNA
<213> ORGANISM: Artificial Sequence
<220> FEATURE:
<223> OTHER INFORMATION: human MCP-1 (including the leader sequence)
      fused to human IgG4 monomeric variant

<400> SEQUENCE: 21
atgaaagtct ctgccgccct tctgtgcctg ctgctcatag cagccacctt cattccccaa      60
gggctcgctc agccagatgc aatcaatgcc ccagtcacct gctgttataa cttcaccaat     120
aggaagatct cagtgcagag gctcgcgagc tatagaagaa tcaccagcag caagtgtccc     180
aaagaagctg tgatcttcaa gaccattgtg gccaaggaga tctgtgctga ccccaagcag     240
aagtgggttc aggattccat ggaccaccty gacaagcaaa cccaaactcc gaagactgga     300
tccgagtcca aatatggtcc cccatctcca tcatctccag cacctgagtt cctgggggga     360
ccatcagtct tcctgttccc cccaaaaccc aaggacactc tcatgatctc ccggacccct     420
gaggtcacgt gcgtggtggt ggacgtgagc caggaagacc ccgaggtcca gttcaactgg     480
tacgtggatg gcgtggaggt gcataatgcc aagacaaagc cgcgggagga gcagttcaac     540
agcacgtacc gtgtggtcag cgtcctcacc gtcctgcacc aggactggct gaacggcaag     600
gagtacaagt gcaaggtctc caacaaaggc ctcccgtcct ccatcgagaa aaccatctcc     660
aaagccaaag ggcagccccg agagccacag gtgtacaccc tgcccccatc ccaggaggag     720
atgaccaaga accaggtcag cctgacctgc ctggtcaaag gcttctaccc cagcgacatc     780
```

```
gccgtggagt gggagagcaa tgggcagccg gagaacaact acaagaccac gcctcccgtg      840
ctggactccg acggctcctt cttcctctac agcaggctaa ccgtggacaa gagcaggtgg      900
caggagggga atgtcttctc atgctccgtg atgcatgagg ctctgcacaa ccactacaca      960
cagaagagcc tctccctgtc tctgggtaaa tga                                   993
```

<210> SEQ ID NO 22
<211> LENGTH: 1005
<212> TYPE: DNA
<213> ORGANISM: Artificial Sequence
<220> FEATURE:
<223> OTHER INFORMATION: human MCP-1 (including the leader sequence)
      fused to human IgG1

<400> SEQUENCE: 22

```
atgaaagtct ctgccgccct tctgtgcctg ctgctcatag cagccacctt cattccccaa       60
gggctcgctc agccagatgc aatcaatgcc ccagtcacct gctgttataa cttcaccaat      120
aggaagatct cagtgcagag gctcgcgagc tatagaagaa tcaccagcag caagtgtccc      180
aaagaagctg tgatcttcaa gaccattgtg gccaaggaga tctgtgctga ccccaagcag      240
aagtgggttc aggattccat ggaccacctg acaagcaaa cccaaactcc gaagactgga       300
tccgttgagc ccaaatcttg tgacaaaact cacacatgcc caccgtgccc agcacctgaa      360
ctcctggggg gaccgtcagt cttcctcttc cccccaaaac ccaaggacac cctcatgatc      420
tcccggaccc ctgaggtcac atgcgtggtg gtggacgtga gccacgaaga ccctgaggtc      480
aagttcaact ggtacgtgga cggcgtggag gtgcataatg ccaagacaaa gccgcgggag      540
gagcagtaca acagcacgta ccgtgtggtc agcgtcctca ccgtcctgca ccaggactgg      600
ctgaatggca aggagtacaa gtgcaaggtc tccaacaaag ccctcccagc ccccatcgag      660
aaaaccatct ccaaagccaa agggcagccc cgagaaccac aggtgtacac cctgccccca      720
tcccgggatg agctgaccaa gaaccaggtc agcctgacct gcctggtcaa aggcttctat      780
cccagcgaca tcgccgtgga gtgggagagc aatgggcagc cggagaacaa ctacaagacc      840
acgcctcccg tgctggactc cgacggctcc ttcttcctct acagcaagct caccgtggac      900
aagagcaggt ggcagcaggg gaacgtcttc tcatgctccg tgatgcatga ggctctgcac      960
aaccactaca cgcagaagag cctctccctg tctccgggta atga                      1005
```

<210> SEQ ID NO 23
<211> LENGTH: 1005
<212> TYPE: DNA
<213> ORGANISM: Artificial Sequence
<220> FEATURE:
<223> OTHER INFORMATION: human MCP-1 (including the leader sequence)
      fused to human IgG1 monomeric variant

<400> SEQUENCE: 23

```
atgaaagtct ctgccgccct tctgtgcctg ctgctcatag cagccacctt cattccccaa       60
gggctcgctc agccagatgc aatcaatgcc ccagtcacct gctgttataa cttcaccaat      120
aggaagatct cagtgcagag gctcgcgagc tatagaagaa tcaccagcag caagtgtccc      180
aaagaagctg tgatcttcaa gaccattgtg gccaaggaga tctgtgctga ccccaagcag      240
aagtgggttc aggattccat ggaccacctg acaagcaaa cccaaactcc gaagactgga       300
tccgttgagc ccaaatcttg tgacaaaact cacacatctc caccgtctcc agcacctgaa      360
ctcctggggg gaccgtcagt cttcctcttc cccccaaaac ccaaggacac cctcatgatc      420
tcccggaccc ctgaggtcac atgcgtggtg gtggacgtga gccacgaaga ccctgaggtc      480
```

```
aagttcaact ggtacgtgga cggcgtggag gtgcataatg ccaagacaaa gccgcgggag      540
gagcagtaca acagcacgta ccgtgtggtc agcgtcctca ccgtcctgca ccaggactgg      600
ctgaatggca aggagtacaa gtgcaaggtc tccaacaaag ccctcccagc ccccatcgag      660
aaaaccatct ccaaagccaa agggcagccc cgagaaccac aggtgtacac cctgccccca      720
tcccgggatg agctgaccaa gaaccaggtc agcctgacct gcctggtcaa aggcttctat      780
cccagcgaca tcgccgtgga gtgggagagc aatgggcagc cggagaacaa ctacaagacc      840
acgcctcccg tgctggactc cgacggctcc ttcttcctct acagcaagct caccgtggac      900
aagagcaggt ggcagcaggg gaacgtcttc tcatgctccg tgatgcatga ggctctgcac      960
aaccactaca cgcagaagag cctctccctg tctccgggta aatga                    1005

<210> SEQ ID NO 24
<211> LENGTH: 6393
<212> TYPE: DNA
<213> ORGANISM: Artificial Sequence
<220> FEATURE:
<223> OTHER INFORMATION: plasmid pcDNA3.1(+) hMCP1 mIgG

<400> SEQUENCE: 24
gacggatcgg gagatctccc gatcccctat ggtgcactct cagtacaatc tgctctgatg       60
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggag tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctagc      900
gtttaaactt aagcttacga tcagtcgaat tcgccgccac catgaaagtc tctgccgccc      960
ttctgtgcct gctgctcata gcagccacct tcattcccca agggctcgct cagccagatg     1020
caatcaatgc cccagtcacc tgctgtttata acttcaccaa taggaagatc tcagtgcaga     1080
ggctcgcgag ctatagaaga atcaccagca gcaagtgtcc caaagaagct gtgatcttca     1140
agaccattgt ggccaaggag atctgtgctg accccaagca agagtgggtt caggattcca     1200
tggaccacct ggacaagcaa acccaaactc cgaagactgg atccgtgccc agggattgtg     1260
gttgtaagcc ttgcatatgt acagtcccag aagtatcatc tgtcttcatc ttcccccaa     1320 agcccaagga tgtgctcacc attactctga ctcctaaggt cacgtgtgtt gtggtagaca     1380
tcagcaagga tgatcccgag gtccagttca gctggtttgt agatgatgtg gaggtgcaca     1440
cagctcagac aaaaccccgg gaggagcagt tcaacagcac tttccgttca gtcagtgaac     1500
ttcccatcat gcaccaggac tggctcaatg gcaaggagtt caaatgcagg gtcaacagtg     1560
```

```
cagcttccc  tgccccatc  gagaaaacca  tctccaaaac  caaaggcaga  ccgaaggctc   1620
cacaggtgta  caccattcca  cctcccaagg  agcagatggc  caaggataaa  gtcagtctga   1680
cctgcatgat  aacagacttc  ttccctgaag  acattactgt  ggagtggcag  tggaatgggc   1740
agccagcgga  gaactacaag  aacactcagc  ccatcatgga  cacagatggc  tcttacttcg   1800
tctacagcaa  gctcaatgtg  cagaagagca  actgggaggc  aggaaatact  ttcacctgct   1860
ctgtgttaca  tgagggcctg  cacaaccacc  atactgagaa  gagcctctcc  cactctcctg   1920
gtaaatgact  agtcatagtt  tagcggccgc  tcgagtctag  agggcccgtt  taaacccgct   1980
gatcagcctc  gactgtgcct  tctagttgcc  agccatctgt  tgtttgcccc  tcccccgtgc   2040
cttccttgac  cctggaaggt  gccactccca  ctgtcctttc  ctaataaaat  gaggaaattg   2100
catcgcattg  tctgagtagg  tgtcattcta  ttctgggggg  tggggtgggg  caggacagca   2160
agggggagga  ttgggaagac  aatagcaggc  atgctgggga  tgcggtgggc  tctatggctt   2220
ctgaggcgga  agaaccagc  tggggctcta  ggggtatcc  ccacgcgccc  tgtagcggcg   2280
cattaagcgc  ggcgggtgtg  gtggttacgc  gcagcgtgac  cgctacactt  gccagcgccc   2340
tagcgcccgc  tcctttcgct  ttcttccctt  cctttctcgc  cacgttcgcc  ggctttcccc   2400
gtcaagctct  aaatcggggg  ctccctttag  ggttccgatt  tagtgcttta  cggcacctcg   2460
accccaaaaa  acttgattag  ggtgatggtt  cacgtagtgg  gccatcgccc  tgatagacgg   2520
tttttcgccc  tttgacgttg  gagtccacgt  tctttaatag  tggactcttg  ttccaaactg   2580
gaacaacact  caaccctatc  tcggtctatt  cttttgattt  ataagggatt  ttgccgattt   2640
cggcctattg  gttaaaaaat  gagctgattt  aacaaaaatt  taacgcgaat  taattctgtg   2700
gaatgtgtgt  cagttagggt  gtggaaagtc  cccaggctcc  ccagcaggca  gaagtatgca   2760
aagcatgcat  ctcaattagt  cagcaaccag  gtgtggaaag  tccccaggct  ccccagcagg   2820
cagaagtatg  caaagcatgc  atctcaatta  gtcagcaacc  atagtcccgc  ccctaactcc   2880
gcccatcccg  cccctaactc  cgcccagttc  cgcccattct  ccgccccatg  gctgactaat   2940 ttttttttatt  tatgcagagg  ccgaggccgc  ctctgcctct  gagctattcc  agaagtagtg   3000
aggaggcttt  tttggaggcc  taggcttttg  caaaaagctc  ccgggagctt  gtatatccat   3060
tttcggatct  gatcaagaga  caggatgagg  atcgtttcgc  atgattgaac  aagatggatt   3120
gcacgcaggt  tctccggccg  cttgggtgga  gaggctattc  ggctatgact  gggcacaaca   3180
gacaatcggc  tgctctgatg  ccgccgtgtt  ccggctgtca  gcgcagggc  gcccggttct   3240 ttttgtcaag  accgacctgt  ccggtgccct  gaatgaactg  caggacgagg  cagcgcggct   3300
atcgtggctg  gccacgacgg  gcgttccttg  cgcagctgtg  ctcgacgttg  tcactgaagc   3360
gggaagggac  tggctgctat  tgggcgaagt  gccggggcag  gatctcctgt  catctcacct   3420
tgctcctgcc  gagaaagtat  ccatcatggc  tgatgcaatg  cggcggctgc  atacgcttga   3480
tccggctacc  tgcccattcg  accaccaagc  gaaacatcgc  atcgagcgag  cacgtactcg   3540
gatggaagcc  ggtcttgtcg  atcaggatga  tctggacgaa  gagcatcagg  ggctcgcgcc   3600
agccgaactg  ttcgccaggc  tcaaggcgcg  catgcccgac  ggcgaggatc  tcgtcgtgac   3660
ccatggcgat  gcctgcttgc  cgaatatcat  ggtggaaaat  ggccgctttt  ctggattcat   3720
cgactgtggc  cggctgggtg  tggcggaccg  ctatcaggac  atagcgttgg  ctacccgtga   3780
tattgctgaa  gagcttggcg  gcgaatgggc  tgaccgcttc  ctcgtgcttt  acggtatcgc   3840
cgctcccgat  tcgcagcgca  tcgccttcta  tcgccttctt  gacgagttct  tctgagcggg   3900
actctggggt  tcgaaatgac  cgaccaagcg  acgcccaacc  tgccatcacg  agatttcgat   3960
```

```
tccaccgccg ccttctatga aaggttgggc ttcggaatcg ttttccggga cgccggctgg      4020
atgatcctcc agcgcgggga tctcatgctg gagttcttcg cccaccccaa cttgtttatt      4080
gcagcttata atggttacaa ataaagcaat agcatcacaa atttcacaaa taaagcattt      4140
ttttcactgc attctagttg tggtttgtcc aaactcatca atgtatctta tcatgtctgt      4200
ataccgtcga cctctagcta gagcttggcg taatcatggt catagctgtt tcctgtgtga      4260
aattgttatc cgctcacaat tccacacaac atacgagccg gaagcataaa gtgtaaagcc      4320
tggggtgcct aatgagtgag ctaactcaca ttaattgcgt tgcgctcact gcccgctttc      4380
cagtcgggaa acctgtcgtg ccagctgcat taatgaatcg gccaacgcgc ggggagaggc      4440
ggtttgcgta ttgggcgctc ttccgcttcc tcgctcactg actcgctgcg ctcggtcgtt      4500
cggctgcggc gagcggtatc agctcactca aaggcggtaa tacggttatc cacagaatca      4560
ggggataacg caggaaagaa catgtgagca aaaggccagc aaaaggccag gaaccgtaaa      4620
aaggccgcgt tgctggcgtt tttccatagg ctccgccccc ctgacgagca tcacaaaaat      4680
cgacgctcaa gtcagaggtg gcgaaacccg acaggactat aaagatacca ggcgtttccc      4740
cctggaagct ccctcgtgcg ctctcctgtt ccgaccctgc cgcttaccgg atacctgtcc      4800
gcctttctcc cttcgggaag cgtggcgctt tctcatagct cacgctgtag gtatctcagt      4860
tcggtgtagg tcgttcgctc caagctgggc tgtgtgcacg aacccccgt tcagcccgac       4920 cgctgcgcct tatccggtaa ctatcgtctt gagtccaacc cggtaagaca cgacttatcg      4980
ccactggcag cagccactgg taacaggatt agcagagcga ggtatgtagg cggtgctaca      5040
gagttcttga agtggtggcc taactacggc tacactagaa gaacagtatt tggtatctgc      5100
gctctgctga agccagttac cttcggaaaa agagttggta gctcttgatc cggcaaacaa      5160
accaccgctg gtagcggttt ttttgtttgc aagcagcaga ttacgcgcag aaaaaaagga      5220
tctcaagaag atcctttgat cttttctacg gggtctgacg ctcagtggaa cgaaaactca      5280
cgttaaggga ttttggtcat gagattatca aaaaggatct tcacctagat ccttttaaat      5340
taaaaatgaa gttttaaatc aatctaaagt atatatgagt aaacttggtc tgacagttac      5400
caatgcttaa tcagtgaggc acctatctca gcgatctgtc tatttcgttc atccatagtt      5460
gcctgactcc ccgtcgtgta gataactacg atacgggagg gcttaccatc tggccccagt      5520
gctgcaatga taccgcgaga cccacgctca ccggctccag atttatcagc aataaaccag      5580
ccagccggaa gggccgagcg cagaagtggt cctgcaactt tatccgcctc catccagtct      5640
attaattgtt gccgggaagc tagagtaagt agttcgccag ttaatagttt gcgcaacgtt      5700
gttgccattg ctacaggcat cgtggtgtca cgctcgtcgt ttggtatggc ttcattcagc      5760
tccggttccc aacgatcaag gcgagttaca tgatccccca tgttgtgcaa aaaagcggtt      5820
agctccttcg gtcctccgat cgttgtcaga agtaagttgg ccgcagtgtt atcactcatg      5880
gttatggcag cactgcataa ttctcttact gtcatgccat ccgtaagatg cttttctgtg      5940
actggtgagt actcaaccaa gtcattctga gaatagtgta tgcggcgacc gagttgctct      6000
tgcccggcgt caatacggga taataccgcg ccacatagca gaactttaaa agtgctcatc      6060
attggaaaac gttcttcggg gcgaaaactc tcaaggatct taccgctgtt gagatccagt      6120
tcgatgtaac ccactcgtgc acccaactga tcttcagcat cttttacttt caccagcgtt      6180
tctgggtgag caaaaacagg aaggcaaaat gccgcaaaaa agggaataag ggcgacacgg      6240
aaatgttgaa tactcatact cttcctttt caatattatt gaagcattta tcagggttat      6300
```

```
tgtctcatga gcggatacat atttgaatgt atttagaaaa ataaacaaat aggggttccg      6360
cgcacatttc cccgaaaagt gccacctgac gtc                                   6393

<210> SEQ ID NO 25
<211> LENGTH: 6399
<212> TYPE: DNA
<213> ORGANISM: Artificial Sequence
<220> FEATURE:
<223> OTHER INFORMATION: Plasmid pcDNA3.1(+) hMCP1 hIgG4

<400> SEQUENCE: 25
gacggatcgg gagatctccc gatccctat ggtgcactct cagtacaatc tgctctgatg       60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg     780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttacga tcagtcgaat tcgccgccac catgaaagtc tctgccgccc    960
ttctgtgcct gctgctcata gcagccacct tcattcccca agggctcgct cagccagatg    1020
caatcaatgc cccagtcacc tgctgttata acttcaccaa taggaagatc tcagtgcaga    1080
ggctcgcgag ctatagaaga atcaccagca gcaagtgtcc caaagaagct gtgatcttca    1140
agaccattgt ggccaaggag atctgtgctg accccaagca gaagtgggtt caggattcca    1200
tggaccacct ggacaagcaa acccaaactc cgaagactgg atccgagtcc aaatatggtc    1260
ccccatgccc atcatgccca gcacctgagt tcctgggggg accatcagtc ttcctgttcc    1320
ccccaaaacc caaggacact ctcatgatct cccggacccc tgaggtcacg tgcgtggtgg    1380
tggacgtgag ccaggaagac cccgaggtcc agttcaactg gtacgtggat ggcgtggagg    1440
tgcataatgc caagacaaag ccgcgggagg agcagttcaa cagcacgtac cgtgtggtca    1500
gcgtcctcac cgtcctgcac caggactggc tgaacggcaa ggagtacaag tgcaaggtct    1560
ccaacaaagg cctcccgtcc tccatcgaga aaaccatctc caaagccaaa gggcagcccc    1620
gagagccaca ggtgtacacc ctgcccccat cccaggagga gatgaccaag aaccaggtca    1680
gcctgacctg cctggtcaaa ggcttctacc ccagcgacat cgccgtggag tgggagagca    1740
atgggcagcc ggagaacaac tacaagacca cgcctcccgt gctggactcc gacggctcct    1800
tcttcctcta cagcaggcta accgtggaca agagcaggtg gcaggagggg aatgtcttct    1860
catgctccgt gatgcatgag gctctgcaca accactacac acagaagagc ctctccctgt    1920
ctctgggtaa atgactagtc atagtttagc ggccgctcga gtctagaggg cccgtttaaa    1980
```

-continued

```
cccgctgatc agcctcgact gtgccttcta gttgccagcc atctgttgtt tgcccctccc    2040
ccgtgccttc cttgaccctg gaaggtgcca ctcccactgt cctttcctaa taaaatgagg    2100
aaattgcatc gcattgtctg agtaggtgtc attctattct gggggtgggg gtggggcagg    2160
acagcaaggg ggaggattgg gaagacaata gcaggcatgc tggggatgcg gtgggctcta    2220
tggcttctga ggcggaaaga accagctggg gctctagggg gtatccccac gcgccctgta    2280
gcggcgcatt aagcgcggcg ggtgtggtgg ttacgcgcag cgtgaccgct acacttgcca    2340
gcgccctagc gcccgctcct ttcgctttct tcccttcctt tctcgccacg ttcgccggct    2400
ttccccgtca gctctaaat cggggctcc ctttagggtt ccgatttagt gctttacggc    2460
acctcgaccc caaaaaactt gattagggtg atggttcacg tagtgggcca tcgccctgat    2520
agacggtttt tcgccctttg acgttggagt ccacgttctt aatagtgga ctcttgttcc    2580 aaactggaac aacactcaac cctatctcgg tctattcttt tgatttataa gggattttgc    2640
cgatttcggc ctattggtta aaaatgagc tgatttaaca aaaatttaac gcgaattaat    2700
tctgtggaat gtgtgtcagt tagggtgtgg aaagtcccca ggctcccag caggcagaag    2760 tatgcaaagc atgcatctca attagtcagc aaccaggtgt ggaaagtccc caggctcccc    2820
agcaggcaga agtatgcaaa gcatgcatct caattagtca gcaaccatag tcccgcccct    2880
aactccgccc atcccgcccc taactccgcc cagttccgcc cattctccgc cccatggctg    2940
actaattttt tttatttatg cagaggccga ggccgcctct gcctctgagc tattccagaa    3000
gtagtgagga ggcttttttg gaggcctagg cttttgcaaa aagctcccgg gagcttgtat    3060
atccattttc ggatctgatc aagagacagg atgaggatcg tttcgcatga ttgaacaaga    3120
tggattgcac gcaggttctc cggccgcttg ggtggagagg ctattcggct atgactgggc    3180
acaacagaca atcggctgct ctgatgccgc cgtgttccgg ctgtcagcgc aggggcgccc    3240
ggttcttttt gtcaagaccg acctgtccgg tgccctgaat gaactgcagg acgaggcagc    3300
gcggctatcg tggctggcca cgacgggcgt tccttgcgca gctgtgctcg acgttgtcac    3360
tgaagcggga agggactggc tgctattggg cgaagtgccg gggcaggatc tcctgtcatc    3420
tcaccttgct cctgccgaga aagtatccat catggctgat gcaatgcggc ggctgcatac    3480
gcttgatccg gctacctgcc cattcgacca ccaagcgaaa catcgcatcg agcgagcacg    3540
tactcggatg aagccggtc ttgtcgatca ggatgatctg gacgaagagc atcaggggct    3600
cgcgccagcc gaactgttcg ccaggctcaa ggcgcgcatg cccgacggcg aggatctcgt    3660
cgtgacccat ggcgatgcct gcttgccgaa tatcatggtg aaaatggcc gcttttctgg    3720 attcatcgac tgtggccggc tgggtgtggc ggaccgctat caggacatag cgttggctac    3780
ccgtgatatt gctgaagagc ttggcggcga atgggctgac cgcttcctcg tgctttacgg    3840
tatcgccgct cccgattcgc agcgcatcgc cttctatcgc cttcttgacg agttcttctg    3900
agcgggactc tggggttcga aatgaccgac caagcgacgc ccaacctgcc atcacgagat    3960
ttcgattcca ccgccgcctt ctatgaaagg ttgggcttcg aatcgttttt ccgggacgcc    4020
ggctggatga tcctccagcg cggggatctc atgctggagt tcttcgccca ccccaacttg    4080
tttattgcag cttataatgg ttacaaataa agcaatagca tcacaaattt cacaaataaa    4140
gcattttttt cactgcattc tagttgtggt ttgtccaaac tcatcaatgt atcttatcat    4200
gtctgtatac cgtcgacctc tagctagagc ttggcgtaat catggtcata gctgtttcct    4260
gtgtgaaatt gttatccgct cacaattcca cacaacatac gagccggaag cataaagtgt    4320
```

```
aaagcctggg gtgcctaatg agtgagctaa ctcacattaa ttgcgttgcg ctcactgccc    4380
gctttccagt cgggaaacct gtcgtgccag ctgcattaat gaatcggcca acgcgcgggg    4440
agaggcggtt tgcgtattgg gcgctcttcc gcttcctcgc tcactgactc gctgcgctcg    4500
gtcgttcggc tgcggcgagc ggtatcagct cactcaaagg cggtaatacg gttatccaca    4560
gaatcagggg ataacgcagg aaagaacatg tgagcaaaag gccagcaaaa ggccaggaac    4620
cgtaaaaagg ccgcgttgct ggcgtttttc cataggctcc gcccccctga cgagcatcac    4680
aaaaatcgac gctcaagtca gaggtggcga aacccgacag gactataaag ataccaggcg    4740
tttccccctg gaagctccct cgtgcgctct cctgttccga ccctgccgct taccggatac    4800
ctgtccgcct ttctcccttc gggaagcgtg gcgctttctc atagctcacg ctgtaggtat    4860
ctcagttcgg tgtaggtcgt tcgctccaag ctgggctgtg tgcacgaacc ccccgttcag    4920
cccgaccgct gcgccttatc cggtaactat cgtcttgagt ccaacccggt aagacacgac    4980
ttatcgccac tggcagcagc cactggtaac aggattagca gagcgaggta tgtaggcggt    5040
gctacagagt tcttgaagtg gtggcctaac tacggctaca ctagaagaac agtatttggt    5100
atctgcgctc tgctgaagcc agttaccttc ggaaaaagag ttggtagctc ttgatccggc    5160
aaacaaacca ccgctggtag cggttttttt gtttgcaagc agcagattac gcgcagaaaa    5220
aaaggatctc aagaagatcc tttgatcttt tctacggggt ctgacgctca gtggaacgaa    5280
aactcacgtt aagggatttt ggtcatgaga ttatcaaaaa ggatcttcac ctagatcctt    5340
ttaaattaaa aatgaagttt taaatcaatc taaagtatat atgagtaaac ttggtctgac    5400
agttaccaat gcttaatcag tgaggcacct atctcagcga tctgtctatt tcgttcatcc    5460
atagttgcct gactccccgt cgtgtagata actacgatac gggagggctt accatctggc    5520
cccagtgctg caatgatacc gcgagaccca cgctcaccgg ctccagattt atcagcaata    5580
aaccagccag ccggaagggc cgagcgcaga agtggtcctg caactttatc cgcctccatc    5640
cagtctatta attgttgccg ggaagctaga gtaagtagtt cgccagttaa tagtttgcgc    5700
aacgttgttg ccattgctac aggcatcgtg gtgtcacgct cgtcgtttgg tatggcttca    5760
ttcagctccg gttcccaacg atcaaggcga gttacatgat cccccatgtt gtgcaaaaaa    5820
gcggttagct ccttcggtcc tccgatcgtt gtcagaagta agttggccgc agtgttatca    5880
ctcatggtta tggcagcact gcataattct cttactgtca tgccatccgt aagatgcttt    5940
tctgtgactg gtgagtactc aaccaagtca ttctgagaat agtgtatgcg gcgaccgagt    6000
tgctcttgcc cggcgtcaat acgggataat accgcgccac atagcagaac tttaaaagtg    6060
ctcatcattg gaaaacgttc ttcggggcga aaactctcaa ggatcttacc gctgttgaga    6120
tccagttcga tgtaacccac tcgtgcaccc aactgatctt cagcatcttt tactttcacc    6180
agcgtttctg ggtgagcaaa aacaggaagg caaaatgccg caaaaaaggg aataagggcg    6240
acacggaaat gttgaatact catactcttc ctttttcaat attattgaag catttatcag    6300
ggttattgtc tcatgagcgg atacatattt gaatgtattt agaaaaataa acaaataggg    6360
gttccgcgca catttccccg aaaagtgcca cctgacgtc                           6399
```

<210> SEQ ID NO 26
<211> LENGTH: 6399
<212> TYPE: DNA
<213> ORGANISM: Artificial Sequence
<220> FEATURE:
<223> OTHER INFORMATION: Plasmid pcDNA3.1(+) hMCP1 hIgG4 monomeric variant -continued

```
<400> SEQUENCE: 26
gacggatcgg gagatctccc gatccctat ggtgcactct cagtacaatc tgctctgatg        60
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggag tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctagc      900
gtttaaactt aagcttacga tcagtcgaat tcgccgccac catgaaagtc tctgccgccc      960
ttctgtgcct gctgctcata gcagccacct tcattcccca agggctcgct cagccagatg     1020
caatcaatgc cccagtcacc tgctgttata acttcaccaa taggaagatc tcagtgcaga     1080
ggctcgcgag ctatagaaga atcaccagca gcaagtgtcc caagaagct gtgatcttca      1140 agaccattgt ggccaaggag atctgtgctg accccaagca gaagtgggtt caggattcca     1200
tggaccacct ggacaagcaa acccaaactc cgaagactgg atccgagtcc aaatatggtc     1260
ccccatctcc atcatctcca gcacctgagt tcctggggg accatcagtc ttcctgttcc      1320
ccccaaaacc caaggacact ctcatgatct cccggacccc tgaggtcacg tgcgtggtgg     1380
tggacgtgag ccaggaagac cccgaggtcc agttcaactg gtacgtggat ggcgtggagg     1440
tgcataatgc caagacaaag ccgcgggagg agcagttcaa cagcacgtac cgtgtggtca     1500
gcgtcctcac cgtcctgcac caggactggc tgaacggcaa ggagtacaag tgcaaggtct     1560
ccaacaaagg cctcccgtcc tccatcgaga aaaccatctc caaagccaaa gggcagcccc     1620
gagagccaca ggtgtacacc ctgccccat cccaggagga gatgaccaag aaccaggtca      1680
gcctgacctg cctggtcaaa ggcttctacc ccagcgacat cgccgtggag tgggagagca     1740
atgggcagcc ggagaacaac tacaagacca cgcctcccgt gctggactcc gacggctcct     1800
tcttcctcta cagcaggcta accgtggaca agagcaggtg gcaggagggg aatgtcttct     1860
catgctccgt gatgcatgag gctctgcaca accactacac acagaagagc ctctccctgt     1920
ctctgggtaa atgactagtc atagtttagc ggccgctcga gtctagaggg cccgtttaaa     1980
cccgctgatc agcctcgact gtgccttcta gttgccagcc atctgttgtt tgcccctccc     2040
ccgtgccttc cttgaccctg gaaggtgcca ctcccactgt cctttcctaa taaaatgagg     2100
aaattgcatc gcattgtctg agtaggtgtc attctattct ggggggtggg gtggggcagg     2160
acagcaaggg ggaggattgg gaagacaata gcaggcatgc tggggatgcg gtgggctcta     2220
tggcttctga ggcggaaaga accagctggg gctctagggg gtatcccac gcgccctgta      2280 gcggcgcatt aagcgcggcg ggtgtggtgg ttacgcgcag cgtgaccgct acacttgcca     2340
```

```
gcgccctagc gcccgctcct ttcgctttct tcccttcctt tctcgccacg ttcgccggct   2400
ttccccgtca agctctaaat cggggggctcc ctttagggtt ccgatttagt gctttacggc   2460
acctcgaccc caaaaaactt gattagggtg atggttcacg tagtgggcca tcgccctgat   2520
agacggtttt tcgcccttg acgttggagt ccacgttctt taatagtgga ctcttgttcc   2580
aaactggaac aacactcaac cctatctcgg tctattcttt tgatttataa gggattttgc   2640
cgatttcggc ctattggtta aaaatgagc tgatttaaca aaaatttaac gcgaattaat   2700
tctgtggaat gtgtgtcagt tagggtgtgg aaagtcccca ggctcccag caggcagaag   2760 tatgcaaagc atgcatctca attagtcagc aaccaggtgt ggaaagtccc caggctcccc   2820
agcaggcaga agtatgcaaa gcatgcatct caattagtca gcaaccatag tcccgcccct   2880
aactccgccc atcccgcccc taactccgcc cagttccgcc cattctccgc cccatggctg   2940
actaattttt tttatttatg cagaggccga ggccgcctct gcctctgagc tattccagaa   3000
gtagtgagga ggcttttttg gaggcctagg cttttgcaaa aagctcccgg gagcttgtat   3060
atccattttc ggatctgatc aagagacagg atgaggatcg tttcgcatga ttgaacaaga   3120
tggattgcac gcaggttctc cggccgcttg ggtggagagg ctattcggct atgactgggc   3180
acaacagaca atcggctgct ctgatgccgc cgtgttccgg ctgtcagcgc aggggcgccc   3240
ggttcttttt gtcaagaccg acctgtccgg tgccctgaat gaactgcagg acgaggcagc   3300
gcggctatcg tggctggcca cgacgggcgt tccttgcgca gctgtgctcg acgttgtcac   3360
tgaagcggga agggactggc tgctattggg cgaagtgccg gggcaggatc tcctgtcatc   3420
tcaccttgct cctgccgaga agtatccat catggctgat gcaatgcggc ggctgcatac   3480
gcttgatccg gctacctgcc cattcgacca ccaagcgaaa catcgcatcg agcgagcacg   3540
tactcggatg aagccggtc ttgtcgatca ggatgatctg gacgaagagc atcagggct   3600 cgcgccagcc gaactgttcg ccaggctcaa ggcgcgcatg cccgacggcg aggatctcgt   3660
cgtgacccat ggcgatgcct gcttgccgaa tatcatggtg aaaatggcc gcttttctgg   3720 attcatcgac tgtggccggc tgggtgtggc ggaccgctat caggacatag cgttggctac   3780
ccgtgatatt gctgaagagc ttggcggcga atgggctgac cgcttcctcg tgctttacgg   3840
tatcgccgct cccgattcgc agcgcatcgc cttctatcgc cttcttgacg agttcttctg   3900
agcgggactc tggggttcga aatgaccgac caagcgacgc ccaacctgcc atcacgagat   3960
ttcgattcca ccgccgcctt ctatgaaagg ttgggcttcg gaatcgtttt ccgggacgcc   4020
ggctggatga tcctccagcg cggggatctc atgctggagt tcttcgccca ccccaacttg   4080
tttattgcag cttataatgg ttacaaataa agcaatagca tcacaaattt cacaaataaa   4140 gcatttttt cactgcattc tagttgtggt ttgtccaaac tcatcaatgt atcttatcat   4200
gtctgtatac cgtcgacctc tagctagagc ttggcgtaat catggtcata gctgtttcct   4260
gtgtgaaatt gttatccgct cacaattcca cacaacatac gagccggaag cataaagtgt   4320
aaagcctggg gtgcctaatg agtgagctaa ctcacattaa ttgcgttgcg ctcactgccc   4380
gctttccagt cgggaaacct gtcgtgccag ctgcattaat gaatcggcca acgcgcgggg   4440
agaggcggtt tgcgtattgg gcgctcttcc gcttcctcgc tcactgactc gctgcgctcg   4500
gtcgttcggc tgcggcgagc ggtatcagct cactcaaagg cggtaatacg gttatccaca   4560
gaatcagggg ataacgcagg aaagaacatg tgagcaaaag gccagcaaaa ggccaggaac   4620
cgtaaaaagg ccgcgttgct ggcgtttttc cataggctcc gcccccctga cgagcatcac   4680
aaaaatcgac gctcaagtca gaggtggcga aacccgacag gactataaag ataccaggcg   4740
```

-continued

```
tttcccctg gaagctccct cgtgcgctct cctgttccga ccctgccgct taccggatac    4800
ctgtccgcct ttctcccttc gggaagcgtg gcgctttctc atagctcacg ctgtaggtat    4860
ctcagttcgg tgtaggtcgt tcgctccaag ctgggctgtg tgcacgaacc cccgttcag     4920 cccgaccgct gcgccttatc cggtaactat cgtcttgagt ccaacccggt aagacacgac    4980
ttatcgccac tggcagcagc cactggtaac aggattagca gagcgaggta tgtaggcggt    5040
gctacagagt tcttgaagtg gtggcctaac tacggctaca ctagaagaac agtatttggt    5100
atctgcgctc tgctgaagcc agttaccttc ggaaaaagag ttggtagctc ttgatccggc    5160
aaacaaacca ccgctggtag cggttttttt gtttgcaagc agcagattac gcgcagaaaa    5220
aaaggatctc aagaagatcc tttgatcttt tctacggggt ctgacgctca gtggaacgaa    5280
aactcacgtt aagggatttt ggtcatgaga ttatcaaaaa ggatcttcac ctagatcctt    5340
ttaaattaaa aatgaagttt taaatcaatc taaagtatat atgagtaaac ttggtctgac    5400
agttaccaat gcttaatcag tgaggcacct atctcagcga tctgtctatt tcgttcatcc    5460
atagttgcct gactccccgt cgtgtagata actacgatac gggagggctt accatctggc    5520
cccagtgctg caatgatacc gcgagaccca cgctcaccgg ctccagattt atcagcaata    5580
aaccagccag ccggaagggc cgagcgcaga agtggtcctg caactttatc cgcctccatc    5640
cagtctatta attgttgccg ggaagctaga gtaagtagtt cgccagttaa tagttttgcgc   5700 aacgttgttg ccattgctac aggcatcgtg gtgtcacgct cgtcgtttgg tatggcttca    5760
ttcagctccg gttcccaacg atcaaggcga gttacatgat cccccatgtt gtgcaaaaaa    5820
gcggttagct ccttcggtcc tccgatcgtt gtcagaagta agttggccgc agtgttatca    5880
ctcatggtta tggcagcact gcataattct cttactgtca tgccatccgt aagatgcttt    5940
tctgtgactg gtgagtactc aaccaagtca ttctgagaat agtgtatgcg gcgaccgagt    6000
tgctcttgcc cggcgtcaat acgggataat accgcgccac atagcagaac tttaaaagtg    6060
ctcatcattg gaaaacgttc ttcggggcga aaactctcaa ggatcttacc gctgttgaga    6120
tccagttcga tgtaacccac tcgtgcaccc aactgatctt cagcatcttt tactttcacc    6180
agcgtttctg ggtgagcaaa aacaggaagg caaaatgccg caaaaaaggg aataagggcg    6240
acacggaaat gttgaatact catactcttc ctttttcaat attattgaag catttatcag    6300
ggttattgtc tcatgagcgg atacatattt gaatgtattt agaaaaataa acaaataggg    6360
gttccgcgca catttccccg aaaagtgcca cctgacgtc                           6399
```

<210> SEQ ID NO 27
<211> LENGTH: 6411
<212> TYPE: DNA
<213> ORGANISM: Artificial Sequence
<220> FEATURE:
<223> OTHER INFORMATION: Plasmid pcDNA3.1(+) hMCP1 hIgG1

<400> SEQUENCE: 27

```
gacggatcgg gagatctccc gatccccat  ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
```

-continued

```
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttacga tcagtcgaat tcgccgccac catgaaagtc tctgccgccc    960
ttctgtgcct gctgctcata gcagccacct tcattcccca agggctcgct cagccagatg   1020
caatcaatgc cccagtcacc tgctgttata acttcaccaa taggaagatc tcagtgcaga   1080
ggctcgcgag ctatagaaga atcaccagca gcaagtgtcc caagaagct gtgatcttca    1140
agaccattgt ggccaaggag atctgtgctg accccaagca gaagtgggtt caggattcca   1200
tggaccacct ggacaagcaa acccaaactc cgaagactgg atccgttgag cccaaatctt   1260
gtgacaaaac tcacacatgc ccaccgtgcc cagcacctga actcctgggg ggaccgtcag   1320
tcttcctctt ccccccaaaa cccaaggaca cctcatgat ctcccggacc cctgaggtca    1380
catgcgtggt ggtggacgtg agccacgaag accctgaggt caagttcaac tggtacgtgg   1440
acggcgtgga ggtgcataat gccaagacaa agccgcggga ggagcagtac aacagcacgt   1500
accgtgtggt cagcgtcctc accgtcctgc accaggactg gctgaatggc aaggagtaca   1560
agtgcaaggt ctccaacaaa gccctcccag cccccatcga aaaaccatc tccaaagcca    1620
aagggcagcc ccgagaacca caggtgtaca ccctgccccc atcccgggat gagctgacca   1680
agaaccaggt cagcctgacc tgcctggtca aaggcttcta tcccagcgac atcgccgtgg   1740
agtgggagag caatgggcag ccggagaaca actacaagac cacgcctccc gtgctggact   1800
ccgacggctc cttcttcctc tacagcaagc tcaccgtgga caagagcagg tggcagcagg   1860
ggaacgtctt ctcatgctcc gtgatgcatg aggctctgca caaccactac acgcagaaga   1920
gcctctccct gtctccgggt aaatgactag tcatagttta gcggccgctc gagtctagag   1980
ggcccgttta aacccgctga tcagcctcga ctgtgccttc tagttgccag ccatctgttg   2040
tttgcccctc ccccgtgcct tccttgaccc tggaaggtgc cactcccact gtcctttcct   2100
aataaaatga ggaaattgca tcgcattgtc tgagtaggtg tcattctatt ctggggggtg   2160
gggtggggca ggacagcaag ggggaggatt gggaagacaa tagcaggcat gctggggatg   2220
cggtgggctc tatggcttct gaggcggaaa gaaccagctg gggctctagg gggtatcccc   2280
acgcgccctg tagcggcgca ttaagcgcgg cgggtgtggt ggttacgcgc agcgtgaccg   2340
ctacacttgc cagcgcccta gcgcccgctc ctttcgcttt cttcccttcc tttctcgcca   2400
cgttcgccgg ctttccccgt caagctctaa atcgggggct ccctttaggg ttccgattta   2460
gtgctttacg gcacctcgac cccaaaaaac ttgattaggg tgatggttca cgtagtgggc   2520
catcgccctg atagacggtt tttcgccctt tgacgttgga gtccacgttc tttaatagtg   2580
gactcttgtt ccaaactgga acaacactca accctatctc ggtctattct tttgatttat   2640
aagggatttt gccgatttcg gcctattggt taaaaaatga gctgatttaa caaaaattta   2700
acgcgaatta attctgtgga atgtgtgtca gttagggtgt ggaaagtccc caggctcccc   2760
agcaggcaga agtatgcaaa gcatgcatct caattagtca gcaaccaggt gtggaaagtc   2820
```

-continued

```
cccaggctcc ccagcaggca gaagtatgca aagcatgcat ctcaattagt cagcaaccat      2880
agtcccgccc ctaactccgc ccatcccgcc cctaactccg cccagttccg cccattctcc      2940
gccccatggc tgactaattt ttttattta tgcagaggcc gaggccgcct ctgcctctga       3000
gctattccag aagtagtgag gaggcttttt tggaggccta ggcttttgca aaaagctccc      3060
gggagcttgt atatccattt tcggatctga tcaagagaca ggatgaggat cgtttcgcat      3120
gattgaacaa gatggattgc acgcaggttc tccggccgct tgggtggaga ggctattcgg      3180
ctatgactgg gcacaacaga caatcggctg ctctgatgcc gccgtgttcc ggctgtcagc      3240
gcaggggcgc ccggttcttt ttgtcaagac cgaccgtgtcc ggtgccctga atgaactgca     3300
ggacgaggca gcgcggctat cgtggctggc cacgacgggc gttccttgcg cagctgtgct     3360
cgacgttgtc actgaagcgg gaagggactg gctgctattg ggcgaagtgc cggggcagga     3420
tctcctgtca tctcaccttg ctcctgccga gaaagtatcc atcatggctg atgcaatgcg     3480
gcggctgcat acgcttgatc cggctacctg cccattcgac caccaagcga acatcgcat     3540 cgagcgagca cgtactcgga tggaagccgg tcttgtcgat caggatgatc tggacgaaga     3600
gcatcagggg ctcgcgccag ccgaactgtt cgccaggctc aaggcgcgca tgcccgacgg     3660
cgaggatctc gtcgtgaccc atggcgatgc ctgcttgccg aatatcatgg tggaaaatgg     3720
ccgcttttct ggattcatcg actgtggccg gctgggtgtg gcggaccgct atcaggacat     3780
agcgttggct acccgtgata ttgctgaaga gcttggcggc gaatgggctg accgcttcct     3840
cgtgctttac ggtatcgccg ctcccgattc gcagcgcatc gccttctatc gccttcttga    3900
cgagttcttc tgagcgggac tctggggttc gaaatgaccg accaagcgac gcccaacctg    3960
ccatcacgag atttcgattc caccgccgcc ttctatgaaa ggttgggctt cggaatcgtt    4020
ttccgggacg ccggctggat gatcctccag cgcgggatc tcatgctgga gttcttcgcc    4080 cacccccaact tgtttattgc agcttataat ggttacaaat aaagcaatag catcacaaat    4140
ttcacaaata aagcatttttt ttcactgcat tctagttgtg gtttgtccaa actcatcaat    4200
gtatcttatc atgtctgtat accgtcgacc tctagctaga gcttggcgta atcatggtca    4260
tagctgtttc ctgtgtgaaa ttgttatccg ctcacaattc cacacaacat acgagccgga    4320
agcataaagt gtaaagcctg gggtgcctaa tgagtgagct aactcacatt aattgcgttg    4380
cgctcactgc ccgcttttcca gtcgggaaac ctgtcgtgcc agctgcatta atgaatcggc    4440
caacgcgcgg ggagaggcgg tttgcgtatt gggcgctctt ccgcttcctc gctcactgac    4500
tcgctgcgct cggtcgttcg gctgcggcga gcggtatcag ctcactcaaa ggcggtaata    4560
cggttatcca cagaatcagg ggataacgca ggaaagaaca tgtgagcaaa aggccagcaa    4620
aaggccagga accgtaaaaa ggccgcgttg ctggcgtttt tccataggct ccgcccccct    4680
gacgagcatc acaaaaatcg acgctcaagt cagaggtggc gaaacccgac aggactataa    4740
agataccagg cgtttccccc tggaagctcc ctcgtgcgct ctcctgttcc gaccctgccg    4800
cttaccggat acctgtccgc ctttctccct tcgggaagcg tggcgctttc tcatagctca    4860
cgctgtaggt atctcagttc ggtgtaggtc gttcgctcca agctgggctg tgtgcacgaa    4920
ccccccgttc agcccgaccg ctgcgcctta tccggtaact atcgtcttga gtccaacccg    4980
gtaagacacg acttatcgcc actggcagca gccactggta acaggattag cagagcgagg    5040
tatgtaggcg gtgctacaga gttcttgaag tggtggccta actacggcta cactagaaga    5100
acagtatttg gtatctgcgc tctgctgaag ccagttacct tcggaaaaag agttggtagc    5160
tcttgatccg gcaaacaaac caccgctggt agcggttttt tgtttgcaa gcagcagatt    5220
```

-continued

| | |
|---|---|
| acgcgcagaa aaaaaggatc tcaagaagat cctttgatct tttctacggg gtctgacgct | 5280 |
| cagtggaacg aaaactcacg ttaagggatt ttggtcatga gattatcaaa aaggatcttc | 5340 |
| acctagatcc ttttaaatta aaaatgaagt tttaaatcaa tctaaagtat atatgagtaa | 5400 |
| acttggtctg acagttacca atgcttaatc agtgaggcac ctatctcagc gatctgtcta | 5460 |
| tttcgttcat ccatagttgc ctgactcccc gtcgtgtaga taactacgat acgggagggc | 5520 |
| ttaccatctg gccccagtgc tgcaatgata ccgcgagacc cacgctcacc ggctccagat | 5580 |
| ttatcagcaa taaaccagcc agccggaagg gccgagcgca gaagtggtcc tgcaacttta | 5640 |
| tccgcctcca tccagtctat taattgttgc cgggaagcta gagtaagtag ttcgccagtt | 5700 |
| aatagtttgc gcaacgttgt tgccattgct acaggcatcg tggtgtcacg ctcgtcgttt | 5760 |
| ggtatggctt cattcagctc cggttcccaa cgatcaaggc gagttacatg atcccccatg | 5820 |
| ttgtgcaaaa aagcggttag ctccttcggt cctccgatcg ttgtcagaag taagttggcc | 5880 |
| gcagtgttat cactcatggt tatggcagca ctgcataatt ctcttactgt catgccatcc | 5940 |
| gtaagatgct tttctgtgac tggtgagtac tcaaccaagt cattctgaga atagtgtatg | 6000 |
| cggcgaccga gttgctcttg cccggcgtca atacgggata ataccgcgcc acatagcaga | 6060 |
| actttaaaag tgctcatcat tggaaaacgt tcttcggggc gaaaactctc aaggatctta | 6120 |
| ccgctgttga gatccagttc gatgtaaccc actcgtgcac ccaactgatc ttcagcatct | 6180 |
| tttactttca ccagcgtttc tgggtgagca aaaacaggaa ggcaaaatgc cgcaaaaaag | 6240 |
| ggaataaggg cgacacggaa atgttgaata ctcatactct ccttttttca atattattga | 6300 |
| agcatttatc agggttattg tctcatgagc ggatacatat ttgaatgtat ttagaaaaat | 6360 |
| aaacaaatag gggttccgcg cacatttccc cgaaaagtgc cacctgacgt c | 6411 |

<210> SEQ ID NO 28
<211> LENGTH: 6411
<212> TYPE: DNA
<213> ORGANISM: Artificial Sequence
<220> FEATURE:
<223> OTHER INFORMATION: Plasmid pcDNA3.1(+) hMCP1 hIgG1 monomeric variant

<400> SEQUENCE: 28

| | |
|---|---|
| gacggatcgg gagatctccc gatcccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |

```
gtttaaactt aagcttacga tcagtcgaat tcgccgccac catgaaagtc tctgccgccc    960
ttctgtgcct gctgctcata gcagccacct tcattcccca agggctcgct cagccagatg   1020
caatcaatgc cccagtcacc tgctgttata acttcaccaa taggaagatc tcagtgcaga   1080
ggctcgcgag ctatagaaga atcaccagca gcaagtgtcc caaagaagct gtgatcttca   1140
agaccattgt ggccaaggag atctgtgctg accccaagca gaagtgggtt caggattcca   1200
tggaccacct ggacaagcaa acccaaactc cgaagactgg atccgttgag cccaaatctt   1260
ctgacaaaac tcacacatct ccaccgtctc cagcacctga actcctgggg ggaccgtcag   1320
tcttcctctt ccccccaaaa cccaaggaca ccctcatgat ctcccggacc cctgaggtca   1380
catgcgtggt ggtggacgtg agccacgaag accctgaggt caagttcaac tggtacgtgg   1440
acggcgtgga ggtgcataat gccaagacaa agccgcggga ggagcagtac aacagcacgt   1500
accgtgtggt cagcgtcctc accgtcctgc accaggactg gctgaatggc aaggagtaca   1560
agtgcaaggt ctccaacaaa gccctcccag ccccatcga gaaaaccatc tccaaagcca   1620
aagggcagcc ccgagaacca caggtgtaca ccctgccccc atcccgggat gagctgacca   1680
agaaccaggt cagcctgacc tgcctggtca aaggcttcta tcccagcgac atcgccgtgg   1740
agtgggagag caatgggcag ccggagaaca actacaagac cacgcctccc gtgctggact   1800
ccgacggctc cttcttcctc tacagcaagc tcaccgtgga caagagcagg tggcagcagg   1860
ggaacgtctt ctcatgctcc gtgatgcatg aggctctgca caaccactac acgcagaaga   1920
gcctctccct gtctccgggt aaatgactag tcatagttta gcggccgctc gagtctagag   1980
ggcccgttta aacccgctga tcagcctcga ctgtgccttc tagttgccag ccatctgttg   2040 tttgccctc cccccgtgcct tccttgaccc tggaaggtgc cactcccact gtcctttcct   2100
aataaaatga ggaaattgca tcgcattgtc tgagtaggtg tcattctatt ctggggggtg   2160
gggtggggca ggacagcaag ggggaggatt ggaagacaa tagcaggcat gctgggatg   2220 cggtgggctc tatggcttct gaggcggaaa gaaccagctg gggctctagg gggtatcccc   2280
acgcgccctg tagcggcgca ttaagcgcgg cgggtgtggt ggttacgcgc agcgtgaccg   2340
ctacacttgc cagcgcccta gcgcccgctc ctttcgcttt cttcccttcc tttctcgcca   2400
cgttcgccgg ctttccccgt caagctctaa atcggggggct cccttttaggg ttccgattta   2460 gtgctttacg gcacctcgac cccaaaaaac ttgattaggg tgatggttca cgtagtgggc   2520
catcgccctg atagacggtt tttcgccctt tgacgttgga gtccacgttc tttaatagtg   2580
gactcttgtt ccaaactgga acaacactca accctatctc ggtctattct tttgatttat   2640
aagggatttt gccgatttcg gcctattggt taaaaaatga gctgatttaa caaaaattta   2700
acgcgaatta attctgtgga atgtgtgtca gttaggtgtg gaaagtccc caggctcccc   2760 agcaggcaga agtatgcaaa gcatgcatct caattagtca gcaaccaggt gtggaaagtc   2820
cccaggctcc ccagcaggca gaagtatgca aagcatgcat ctcaattagt cagcaaccat   2880
agtcccgccc ctaactccgc ccatcccgcc cctaactccg cccagttccg cccattctcc   2940
gccccatggc tgactaattt tttttattta tgcagaggcc gaggccgcct ctgcctctga   3000
gctattccag aagtagtgag gaggcttttt tggaggccta ggcttttgca aaaagctccc   3060
gggagcttgt atatccattt tcggatctga tcaagagaca ggatgaggat cgtttcgcat   3120
gattgaacaa gatggattgc acgcaggttc tccggccgct tgggtggaga ggctattcgg   3180
ctatgactgg gcacaacaga caatcggctg ctctgatgcc gccgtgttcc ggctgtcagc   3240
gcaggggcgc ccggttcttt ttgtcaagac cgacctgtcc ggtgccctga atgaactgca   3300
```

-continued

| | |
|---|---|
| ggacgaggca gcgcggctat cgtggctggc cacgacgggc gttccttgcg cagctgtgct | 3360 |
| cgacgttgtc actgaagcgg aagggactg gctgctattg ggcgaagtgc cggggcagga | 3420 |
| tctcctgtca tctcaccttg ctcctgccga gaaagtatcc atcatggctg atgcaatgcg | 3480 |
| gcggctgcat acgcttgatc cggctacctg cccattcgac caccaagcga acatcgcat | 3540 |
| cgagcgagca cgtactcgga tggaagccgg tcttgtcgat caggatgatc tggacgaaga | 3600 |
| gcatcagggg ctcgcgccag ccgaactgtt cgccaggctc aaggcgcgca tgcccgacgg | 3660 |
| cgaggatctc gtcgtgaccc atggcgatgc ctgcttgccg aatatcatgg tggaaaatgg | 3720 |
| ccgcttttct ggattcatcg actgtggccg gctgggtgtg gcggaccgct atcaggacat | 3780 |
| agcgttggct acccgtgata ttgctgaaga gcttggcggc gaatgggctg accgcttcct | 3840 |
| cgtgctttac ggtatcgccg ctcccgattc gcagcgcatc gccttctatc gccttcttga | 3900 |
| cgagttcttc tgagcgggac tctggggttc gaaatgaccg accaagcgac gcccaacctg | 3960 |
| ccatcacgag atttcgattc caccgccgcc ttctatgaaa ggttgggctt cggaatcgtt | 4020 |
| ttccgggacg ccggctggat gatcctccag cgcggggatc tcatgctgga gttcttcgcc | 4080 |
| caccccaact tgtttattgc agcttataat ggttacaaat aaagcaatag catcacaaat | 4140 |
| ttcacaaata aagcattttt tcactgcat tctagttgtg gtttgtccaa actcatcaat | 4200 |
| gtatcttatc atgtctgtat accgtcgacc tctagctaga gcttggcgta atcatggtca | 4260 |
| tagctgtttc ctgtgtgaaa ttgttatccg ctcacaattc cacacaacat acgagccgga | 4320 |
| agcataaagt gtaaagcctg gggtgcctaa tgagtgagct aactcacatt aattgcgttg | 4380 |
| cgctcactgc ccgctttcca gtcgggaaac ctgtcgtgcc agctgcatta tgaatcggc | 4440 |
| caacgcgcgg ggagaggcgg tttgcgtatt gggcgctctt ccgcttcctc gctcactgac | 4500 |
| tcgctgcgct cggtcgttcg gctgcggcga gcggtatcag ctcactcaaa ggcggtaata | 4560 |
| cggttatcca cagaatcagg ggataacgca ggaaagaaca tgtgagcaaa aggccagcaa | 4620 |
| aaggccagga accgtaaaaa ggccgcgttg ctggcgtttt tccataggct ccgcccccct | 4680 |
| gacgagcatc acaaaaatcg acgctcaagt cagaggtggc gaaacccgac aggactataa | 4740 |
| agataccagg cgtttccccc tggaagctcc ctcgtgcgct ctcctgttcc gaccctgccg | 4800 |
| cttaccggat acctgtccgc ctttctccct tcgggaagcg tggcgctttc tcatagctca | 4860 |
| cgctgtaggt atctcagttc ggtgtaggtc gttcgctcca agctgggctg tgtgcacgaa | 4920 |
| ccccccgttc agcccgaccg ctgcgcctta tccggtaact atcgtcttga gtccaacccg | 4980 |
| gtaagacacg acttatcgcc actggcagca gccactggta acaggattag cagagcgagg | 5040 |
| tatgtaggcg gtgctacaga gttcttgaag tggtggccta actacggcta cactagaaga | 5100 |
| acagtatttg gtatctgcgc tctgctgaag ccagttacct tcggaaaaag agttggtagc | 5160 |
| tcttgatccg gcaaacaaac caccgctggt agcggttttt tgtttgcaa gcagcagatt | 5220 |
| acgcgcagaa aaaaggatc tcaagaagat cctttgatct tttctacggg gtctgacgct | 5280 |
| cagtggaacg aaaactcacg ttaagggatt ttggtcatga gattatcaaa aaggatcttc | 5340 |
| acctagatcc ttttaaatta aaatgaagt tttaaatcaa tctaaagtat atatgagtaa | 5400 |
| acttggtctg acagttacca atgcttaatc agtgaggcac ctatctcagc gatctgtcta | 5460 |
| tttcgttcat ccatagttgc ctgactcccc gtcgtgtaga taactacgat acgggagggc | 5520 |
| ttaccatctg gccccagtgc tgcaatgata ccgcgagacc cacgctcacc ggctccagat | 5580 |
| ttatcagcaa taaccagcc agccggaagg gccgagcgca gaagtggtcc tgcaacttta | 5640 |
| tccgcctcca tccagtctat taattgttgc cgggaagcta gagtaagtag ttcgccagtt | 5700 |

-continued

```
aatagtttgc gcaacgttgt tgccattgct acaggcatcg tggtgtcacg ctcgtcgttt      5760
ggtatggctt cattcagctc cggttcccaa cgatcaaggc gagttacatg atcccccatg      5820
ttgtgcaaaa aagcggttag ctccttcggt cctccgatcg ttgtcagaag taagttggcc      5880
gcagtgttat cactcatggt tatggcagca ctgcataatt ctcttactgt catgccatcc      5940
gtaagatgct tttctgtgac tggtgagtac tcaaccaagt cattctgaga atagtgtatg      6000
cggcgaccga gttgctcttg cccggcgtca atacgggata ataccgcgcc acatagcaga      6060
actttaaaag tgctcatcat tggaaaacgt tcttcggggc gaaaactctc aaggatctta      6120
ccgctgttga gatccagttc gatgtaaccc actcgtgcac ccaactgatc ttcagcatct      6180
tttactttca ccagcgtttc tgggtgagca aaaacaggaa ggcaaaatgc cgcaaaaaag      6240
ggaataaggg cgacacggaa atgttgaata ctcatactct tcctttttca atattattga      6300
agcatttatc agggttattg tctcatgagc ggatacatat ttgaatgtat ttagaaaaat      6360
aaacaaatag gggttccgcg cacatttccc cgaaaagtgc cacctgacgt c              6411
```

<210> SEQ ID NO 29
<211> LENGTH: 13
<212> TYPE: PRT
<213> ORGANISM: Artificial Sequence
<220> FEATURE:
<223> OTHER INFORMATION: PLP139-151 peptide

<400> SEQUENCE: 29

```
His Cys Leu Gly Lys Trp Leu Gly His Pro Asp Lys Phe
1               5                   10
```

<210> SEQ ID NO 30
<211> LENGTH: 148
<212> TYPE: PRT
<213> ORGANISM: Mus sp.

<400> SEQUENCE: 30

```
Met Gln Val Pro Val Met Leu Leu Gly Leu Leu Phe Thr Val Ala Gly
1               5                   10                  15

Trp Ser Ile His Val Leu Ala Gln Pro Asp Ala Val Asn Ala Pro Leu
                20                  25                  30

Thr Cys Cys Tyr Ser Phe Thr Ser Lys Met Ile Pro Met Ser Arg Leu
            35                  40                  45

Glu Ser Tyr Lys Arg Ile Thr Ser Ser Arg Cys Pro Lys Glu Ala Val
        50                  55                  60

Val Phe Val Thr Lys Leu Lys Arg Glu Val Cys Ala Asp Pro Lys Lys
65                  70                  75                  80

Glu Trp Val Gln Thr Tyr Ile Lys Asn Leu Asp Arg Asn Gln Met Arg
                85                  90                  95

Ser Glu Pro Thr Thr Leu Phe Lys Thr Ala Ser Ala Leu Arg Ser Ser
                100                 105                 110

Ala Pro Leu Asn Val Lys Leu Thr Arg Lys Ser Glu Ala Asn Ala Ser
            115                 120                 125

Thr Thr Phe Ser Thr Thr Thr Ser Ser Thr Ser Val Gly Val Thr Ser
        130                 135                 140

Val Thr Val Asn
145
```

METHOD FOR TREATING ATHEROSCLEROSIS BY ADMINISTERING HUMAN MCP1 FUSIONS

The present application is a continuation of U.S. patent application Ser. No. 12/621,228; filed Nov. 18, 2009; which is a divisional application of U.S. patent application Ser. No. 11/502,064; filed Aug. 10, 2006; which claims the benefit of U.S. provisional patent application No. 60/707,731, filed Aug. 12, 2005, each of which are herein incorporated by reference in their entireties.

FIELD OF THE INVENTION

The present invention relates to fusion proteins that are useful for, inter alia, treatment or prevention of inflammatory conditions; along with method for treating such conditions using the fusion proteins.

BACKGROUND OF THE INVENTION

Monocyte chemotactic protein-1 (MCP1, also known as HC11, MCAF, CCL2, SCYA2, GDCF-2, SMC-CF, HSMCR30, MGC9434, GDCF-2 and HC11) is a highly selective, high-affinity chemokine ligand for chemokine receptor CCR2. It is secreted locally by inflammatory tissues to attract CCR2-bearing cells such as monocytes and memory T cells. Upon binding to CCR2, MCP1 induces calcium flux and cell migration toward the gradient of MCP1.

There is substantial biological and genetic evidence for the critical involvement of MCP1 and CCR2 in inflammatory diseases including arthritis, atherosclerosis, multiple sclerosis, and fibrosis. Mice deficient in either MCP1 or CCR2 were protected from developing experimental autoimmune encephalomyelitis (EAE) (Huang et al., 2001, J. Exp. Med. 193:713; Izikson et al., 2000, J. Exp. Med. 192:1075; Mahad and Ransohoff, 2003, Semi. Immunol. 15:23). CCR2-deficient mice were also protected from collagen-induced arthritis (Quinones et al., 2004, J. Olin. Invest. 113:856). Furthermore, CCR2-knockout mice were resistant to the development of atherosclerotic plaques (Charo and Taubman, 2004, Circ. Res. 95:858).

There exists a need in the art for anti-inflammatory agents that target CCR2-mediated inflammation.

SUMMARY OF THE INVENTION

The invention disclosed herein stems from the surprising discovery that the targeting of a chemokine receptor by desensitizing the receptor with the systemic administration of a chemokine ligand, leads to the prevention of the receptor-bearing cells from trafficking to inflammatory sites and from exposure to activation signals such as interferon-gamma. In the exemplary examples discussed herein, CCR2 was used as the chemokine receptor and MCP1 as the chemokine ligand. To extend the serum half-life of the MCP1 chemokine an immunoglobulin-fusion protein was designed by tagging the MCP1 with the immunoglobulin constant region (from the hinge to the CH3 regions).

The present invention addresses the need for anti-inflammatory therapies and other needs by providing, in an embodiment of the invention, a chemokine ligand, such as MCP1, SDF1 or MIP1β or a fragment thereof (e.g., mature polypeptide thereof), fused to an agent that extends the in vivo half-life of the protein, for example, an immunoglobulin or a fragment thereof or PEG.

The present invention provides an isolated polypeptide comprising (1) one or more chemokine polypeptides fused to one or more half-life extending moieties; or (2) two or more fused chemokine polypeptides. In an embodiment of the invention, the MCP1 is a member selected from the group consisting of human MCP1 and mouse MCP1. In an embodiment of the invention, the moiety is polyethylene glycol (PEG) or an immunoglobulin. In an embodiment of the invention, the polypeptide comprises one or more mature MCP1 polypeptides (e.g., human or mouse) fused to one or more immunoglobulins (e.g., any of SEQ ID NOs: 8-12). In an embodiment of the invention, the MCP1 is a member selected from the group consisting of human MCP1 and mouse MCP1. In an embodiment of the invention, the immunoglobulin is a member selected from the group consisting of γ1 and γ4 from the hinge to the CH3 region. In an embodiment of the invention, the polypeptide is a member selected from the group consisting of: mature human MCP1 fused to mouse IgG1; mature human MCP1 fused to human IgG4; mature human MCP1 fused to human IgG4 monomeric variant; mature human MCP1 fused to human IgG1; and mature human MCP1 fused to human IgG1 monomeric variant. In an embodiment of the invention, the MCP1 comprises an amino acid sequence selected from the group consisting of SEQ ID NOs: 2. In an embodiment of the invention, the immunoglobulin comprises an amino acid sequence set forth in SEQ ID NOs: 3-7. In an embodiment of the invention, the MCP1 is fused to the immunoglobulin by a peptide linker (e.g., GS). The scope of the present invention includes a pharmaceutical composition comprising any of the polypeptides and a pharmaceutically acceptable carrier. Also within the scope of the present invention is any of the polypeptides herein in association with one or more further therapeutic agents or a pharmaceutical composition thereof; for example, wherein the further therapeutic agent is a member selected from the group consisting of aspirin, diclofenac, diflunisal, etodolac, fenoprofen, floctafenine, flurbiprofen, ibuprofen, indomethacin, ketoprofen, ketorolac, meclofenamate, mefenamic acid, meloxicam, nabumetone, naproxen, oxaprozin, phenylbutazone, piroxicam, salsalate, sulindac, tenoxicam, tiaprofenic acid, tolmetin, betamethasone benzoate, betamethasone valerate, clobetasol propionate, desoximetasone, fluocinolone acetonide, flurandrenolide, a topical steroid, alclometasone dipropionate, aloe vera, amcinonide, amcinonide, anthralin, betamethasone dipropionate, betamethasone valerate, calcipotriene, clobetasol propionate, coal tar, Dead Sea salts, desonide, desonide; betamethasone valerate, desoximetasone, diflorasone diacetate, epsom salts, fluocinolone acetonide, fluocinonide, flurandrenolide, fluticasone propionate, halcinonide, halobetasol propionate, hydrocortisone valerate, hydrocortisone, mometasone furoate, oilated oatmeal, petroleum jelly, prednicarbate, salicylic acid, tazarotene, triamcinolone acetonide, a mixture of hydrocortisone, dexamethasone, methylprednisolone and prednisolone, alefacept, etanercept, cyclosporine, methotrexate, acitretin, isotretinoin, hydroxyurea, mycophenolate mofetil, sulfasalazine, 6-Thioguanine, anakinra, injectable gold, penicillamine, azathioprine, chloroquine, hydroxychloroquine, sulfasalazine, oral gold, auranofin, gold sodium thiomalate, aurothioglucose, mesalamine, sulfasalazine, budesonide, metronidazole, ciprofloxacin, azathioprine, 6-mercaptopurine or dietary supplementation of calcium, folate, vitamin B12, celecoxib, rofecoxib, valdecoxib, lumiracoxib, etoricoxib, efalizumab, adalimumab, infliximab and ABX-IL8.

The present invention provides an isolated polynucleotide encoding any of the polypeptides herein—e.g., encoding a member selected from the group consisting of human unprocessed MCP1 fused to mouse IgG1; human unprocessed MCP1 fused to human IgG4; human unprocessed MCP1 fused to human IgG4 monomeric variant; human unprocessed MCP1 fused to human IgG1; and human unprocessed MCP1 fused to human IgG1 monomeric variant. In an embodiment of the invention, the MCP1 is encoded by a nucleotide sequence set forth in SEQ ID NO: 13. In an embodiment of the invention, the immunoglobulin is encoded by a nucleotide sequence selected from the group consisting of SEQ ID NOs: 14-18. In an embodiment of the invention, the nucleotide sequence is selected from the group consisting of SEQ ID NOs: 19-23. The present invention also includes an isolated vector (e.g., as shown in FIG. 1 and/or comprising the nucleotide sequence of SEQ ID NO: 24) comprising the polynucleotide (e.g., pcDNA3.1(+)hMCP1 mIgG) as well as a host cell comprising the vector.

The present invention also provides a method for making an MCP1-Ig polypeptide comprising transforming a host cell with an expression vector (e.g., pcDNA3.1(+)hMCP1 mIgG) comprising a polynucleotide encoding said polypeptide under conditions suitable for said expression and, optionally, isolating the polypeptide from the host cell. In an embodiment of the invention, the polynucleotide encodes a polypeptide comprising an amino acid sequence selected from the group consisting of SEQ ID NOs: 8-12. Any polypeptide made by the method is also within the scope of the present invention.

The present invention provides a method for treating a disorder treatable by decreasing expression or activity of a chemokine ligand (e.g., MCP1, SDF1 or MIP1β) or chemokine receptor or by decreasing the migration of chemokine receptor bearing cells into inflammatory tissues, in a subject, comprising desensitizing chemokine receptor bearing cells, in the subject, to chemokine ligand. In an embodiment of the invention, the disorder is a member selected from the group consisting of an inflammatory medical disorder, parasitic infection, bacterial infection, viral infection, cancer, a cardiovascular disorder and a circulatory disorder. In an embodiment of the invention, the chemokine receptor bearing cells are desensitized to the chemokine ligand by systemic administration of chemokine ligand polypeptide or a chemokine ligand polypeptide fused to a half-life extending moiety (e.g., immunoglobulin or fragment thereof). In an embodiment of the invention, the MCP1 comprises an amino acid sequence set forth in SEQ ID NO: 2. In an embodiment of the invention, the Ig comprises an amino acid sequence selected from the group consisting of SEQ ID NOs: 3-7. In an embodiment of the invention, the polypeptide is MCP1-Ig comprising an amino acid sequence selected from the group consisting of SEQ ID NOs: 8-12.

The present invention provides a method for treating or preventing an inflammatory medical disorder in a subject comprising administering, to the subject, MCP1-Ig or a pharmaceutical composition thereof optionally in association with a further therapeutic agent or procedure. In an embodiment of the invention, the disorder is a member selected from the group consisting of appendicitis, peptic ulcer, gastric ulcer and duodenal ulcer, peritonitis, pancreatitis, inflammatory bowel disease, colitis, ulcerative colitis, pseudomembranous colitis, acute colitis, ischemic colitis, diverticulitis, epiglottitis, achalasia, cholangitis, cholecystitis, coeliac disease, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, and urethritis, bronchitis, emphysema, rhinitis, cystic fibrosis, pneumonitis, adult respiratory distress syndrome, pneumoultramicroscopicsilicovolcanoconiosis, alvealitis, bronchiolitis, pharyngitis, pleurisy, sinusitis, dermatitis, atopic dermatitis, dermatomyositis, sunburn, urticaria warts, wheals, stenosis, restenosis, vasulitis, angiitis, endocarditis, arteritis, atherosclerosis, thrombophlebitis, pericarditis, myocarditis, myocardial ischemia, periarteritis nodosa, rheumatic fever, meningitis, encephalitis, multiple sclerosis, neuritis, neuralgia, uveitis, arthritides and arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection and graft-versus-host disease. In an embodiment of the present invention, the MCP1 comprises an amino acid sequence is set forth in SEQ ID NO: 2. In an embodiment of the present invention, the Ig comprises amino acid sequence selected from the group consisting of SEQ ID NOs: 3-7. In an embodiment of the present invention, the MCP1-Ig comprises an amino acid sequence selected from the group consisting of SEQ ID NOs: 8-12. In an embodiment of the present invention, the subject is a human. In an embodiment of the present invention, the further therapeutic agent or procedure is a member selected from the group consisting of aspirin, diclofenac, diflunisal, etodolac, fenoprofen, floctafenine, flurbiprofen, ibuprofen, indomethacin, ketoprofen, ketorolac, meclofenamate, mefenamic acid, meloxicam, nabumetone, naproxen, oxaprozin, phenylbutazone, piroxicam, salsalate, sulindac, tenoxicam, tiaprofenic acid, tolmetin, betamethasone benzoate, betamethasone valerate, clobetasol propionate, desoximetasone, fluocinolone acetonide, flurandrenolide, a topical steroid, alclometasone dipropionate, aloe vera, amcinonide, amcinonide, anthralin, betamethasone dipropionate, betamethasone valerate, calcipotriene, clobetasol propionate, coal tar, Dead Sea salts, desonide, desonide; betamethasone valerate, desoximetasone, diflorasone diacetate, epsom salts, fluocinolone acetonide, fluocinonide, flurandrenolide, fluticasone propionate, halcinonide, halobetasol propionate, hydrocortisone valerate, hydrocortisone, mometasone furoate, oilated oatmeal, petroleum jelly, prednicarbate, salicylic acid, tazarotene, triamcinolone acetonide, a mixture of hydrocortisone, dexamethasone, methylprednisolone and prednisolone, alefacept, etanercept, cyclosporine, methotrexate, acitretin, isotretinoin, hydroxyurea, mycophenolate mofetil, sulfasalazine, 6-Thioguanine, anakinra, injectable gold, penicillamine, azathioprine, chloroquine, hydroxychloroquine, sulfasalazine, oral gold, auranofin, gold sodium thiomalate, aurothioglucose, mesalamine, sulfasalazine, budesonide, metronidazole, ciprofloxacin, azathioprine, 6-mercaptopurine or dietary supplementation of calcium, folate, vitamin B12, celecoxib, rofecoxib, valdecoxib, lumiracoxib, etoricoxib, efalizumab, adalimumab, infliximab, ABX-IL8 and phototherapy.

The present invention provides a method for increasing the in vivo half-life of MCP1 in the body of a subject comprising fusing MCP1 to an immunoglobulin or a fragment thereof. In an embodiment of the present invention, the MCP1 comprises an amino acid sequence is set forth in SEQ ID NO: 2. In an embodiment of the present invention, the immunoglobulin comprises an amino acid sequence selected from the group consisting of SEQ ID NOs: 3-7.

BRIEF DESCRIPTION OF THE FIGURES

FIG. 1. Map of plasmid pcDNA3.1(+)hMCP1 mIgG.

DETAILED DESCRIPTION OF THE INVENTION

The present invention provides a polypeptide comprising MCP1 fused to any half-life extending moiety that extends or prolongs the in vivo half-life of MCP1 in the body (e.g., in the plasma) of a subject.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al., (eds.), *Current Protocols in Molecular Biology*, John Wiley & Sons, Inc. (1994).

A "polynucleotide", "nucleic acid" or "nucleic acid molecule" includes the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in single stranded form, double-stranded form or otherwise.

A "polynucleotide sequence", "nucleic acid sequence" or "nucleotide sequence" is a series of nucleotide bases (also called "nucleotides") in a nucleic acid, such as DNA or RNA, and means any chain of two or more nucleotides.

A "coding sequence" or a sequence "encoding" an expression product, such as a RNA, polypeptide, protein, or enzyme, is a nucleotide sequence that, when expressed, results in production of the product.

The term "gene" means a DNA sequence that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

A "protein sequence", "peptide sequence" or "polypeptide sequence" or "amino acid sequence" includes a series of two or more amino acids in a protein, peptide or polypeptide.

The terms "isolated polynucleotide" or "isolated polypeptide" include a polynucleotide (e.g., RNA or DNA molecule, or a mixed polymer) or a polypeptide, respectively, which are partially or fully separated from other components that are normally found in cells or in recombinant DNA expression systems. These components include, but are not limited to, cell membranes, cell walls, ribosomes, polymerases, serum components and extraneous genomic sequences.

An isolated polynucleotide or polypeptide will, preferably, be an essentially homogeneous composition of molecules but may contain some heterogeneity.

"Amplification" of DNA as used herein includes the use of polymerase chain reaction (PCR) to increase the concentration of a particular DNA sequence within a mixture of DNA sequences. For a description of PCR see Saiki, et al., Science (1988) 239:487.

The term "host cell" includes any cell of any organism that is selected, modified, transfected, transformed, grown, or used or manipulated in any way, for the production of a substance by the cell, for example the expression or replication, by the cell, of a gene, a DNA or RNA sequence or a protein. Host cells include bacterial cells (e.g., *E. coli*), Chinese hamster ovary (CHO) cells, HEK293 cells, myeloma cells including but not limited to SP2/0, NS1, and NS0, murine macrophage J774 cells or any other macrophage cell line and human intestinal epithelial Caco2 cells.

The nucleotide sequence of a polynucleotide may be determined by any method known in the art (e.g., chemical sequencing or enzymatic sequencing). "Chemical sequencing" of DNA includes methods such as that of Maxam and Gilbert (1977) (Proc. Natl. Acad. Sci. USA 74:560), in which DNA is randomly cleaved using individual base-specific reactions. "Enzymatic sequencing" of DNA includes methods such as that of Sanger (Sanger, et al., (1977) Proc. Natl. Acad. Sci. USA 74:5463).

The polynucleotides herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a polynucleotide of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the β-lactamase promoter (Villa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

A coding sequence is "under the control of", "functionally associated with" or "operably associated with" transcriptional and translational control sequences in a cell when the sequences direct RNA polymerase mediated transcription of the coding sequence into RNA, preferably mRNA, which then may be RNA spliced (if it contains introns) and, optionally, translated into a protein encoded by the coding sequence.

The terms "express" and "expression" mean allowing or causing the information in a gene, RNA or DNA sequence to become manifest; for example, producing a protein by activating the cellular functions involved in transcription and translation of a corresponding gene. A DNA sequence is expressed in or by a cell to form an "expression product" such as an RNA (e.g., mRNA) or a protein. The expression product itself may also be said to be "expressed" by the cell.

The term "transformation" means the introduction of polynucleotide into a cell. The introduced gene or sequence may be called a "clone". A host cell that receives the introduced DNA or RNA has been "transformed" and is a "transformant" or a "clone." The DNA or RNA introduced to a host cell can come from any source, including cells of the same genus or species as the host cell, or from cells of a different genus or species.

The term "vector" includes a vehicle (e.g., a plasmid) by which a DNA or RNA sequence can be introduced into a host cell, so as to transform the host and, optionally, promote expression and/or replication of the introduced sequence.

Vectors that can be used in this invention include plasmids, viruses, bacteriophage, integratable DNA fragments, and other vehicles that may facilitate introduction of the polynucleotide into the host. Plasmids are the most commonly used form of vector but all other forms of vectors which serve a similar function and which are, or become, known in the art are suitable for use herein. See, e.g., Pouwels, et al., *Cloning Vectors: A Laboratory Manual,* 1985 and Supplements, Elsevier, N.Y., and Rodriguez et al. (eds.), *Vectors: A Survey of Molecular Cloning Vectors and Their Uses,* 1988, Buttersworth, Boston, Mass.

The present invention comprises a method for producing MCP1 (e.g., a mature MCP1 polypeptide), an MCP1 multimer or a fusion thereof (e.g., fused to an in vivo half-life extending moiety (e.g., Ig)) (e.g., in an expression system). In an embodiment of the invention, the MCP1 or multimer or fusion thereof is inserted into an expression vector which is introduced into a suitable host cell. The protein is then allowed to express in the host cell. The protein may then be isolated from the host cell and purified further. Any polypeptide produced by such a method is also within the scope of the present invention.

The term "expression system" means a host cell and compatible vector which, under suitable conditions, can express a protein or nucleic acid which is carried by the vector and introduced to the host cell. Common expression systems include *E. coli* host cells or mammalian host cells (e.g., CHO cells, HEK293 cells, and myeloma cells) and plasmid vectors, insect host cells and Baculovirus vectors, and mammalian host cells and vectors.

Expression of nucleic acids encoding MCP1 or multimer or fusion thereof of this invention can be carried out by conventional methods in either prokaryotic or eukaryotic cells. Although *E. coli* host cells are employed most frequently in prokaryotic systems, many other bacteria, such as various strains of *Pseudomonas* and *Bacillus*, are known in the art and can be used as well. Suitable host cells for expressing nucleic acids encoding the polypeptides include prokaryotes and higher eukaryotes. Prokaryotes include both gram-negative and gram-positive organisms, e.g., *E. coli* and *B. subtilis*. Higher eukaryotes include established tissue culture cell lines from animal cells (e.g., CHO cells), both of non-mammalian origin, e.g., insect cells, and birds, and of mammalian origin, e.g., human, primates, and rodents.

Prokaryotic host-vector systems include a wide variety of vectors for many different species. A representative vector for amplifying DNA is pBR322 or any of many of its derivatives (e.g., pUC18 or 19). Vectors that can be used to express the MCP1 polypeptides include, but are not limited to, those containing the lac promoter (pUC-series); trp promoter (pBR322-trp); Ipp promoter (the pIN-series); lambda-pP or pR promoters (pOTS); or hybrid promoters such as ptac (pDR540). See Brosius et al., "Expression Vectors Employing Lambda-, trp-, lac-, and Ipp-derived Promoters", in Rodriguez and Denhardt (eds.) *Vectors: A Survey of Molecular Cloning Vectors and Their Uses,* 1988, Buttersworth, Boston, pp. 205-236. Many polypeptides can be expressed, at high levels, in an *E. coli*/T7 expression system as disclosed in U.S. Pat. Nos. 4,952,496, 5,693,489 and 5,869,320 and in Davanloo, P., et al., (1984) Proc. Natl. Acad. Sci. USA 81: 2035-2039; Studier, F. W., et al., (1986) J. Mol. Biol. 189: 113-130; Rosenberg, A. H., et al., (1987) Gene 56: 125-135; and Dunn, J. J., et al., (1988) Gene 68: 259.

The T7 expression system comprises pET plasmids which contain an expression cassette in which the gene of interest (e.g., MCP1 or multimer or fusion thereof) is inserted behind an extremely strong promoter from the *E. coli* bacteriophage T7 (Studier et al., J. Mol. Biol. 189(1):113-30 (1986)). In the absence of the T7 polymerase, this promoter is shut off. For expression to occur, the pET plasmids are transformed into bacteria strains that typically contain a single copy of the T7 polymerase on the chromosome in a lambda lysogen (the most commonly used lysogen is known as DE3). The T7 polymerase is under the control of the Lac-UV5 lac promoter. When cells are grown in media without lactose, the lac repressor (lacI) binds to the lac operator and prevents transcription from the lac promoter. When lactose is the sole carbon source, or when the lactose analog isopropyl-beta-D-thiogalactopyranoside (IPTG) is added to the media, lactose (or IPTG) binds to the repressor and induces its dissociation from the operator, permitting transcription from the promoter. Addition of glucose to the culture media contributes to repression of the T7 RNA polymerase via the mechanism of catabolite repression.

Higher eukaryotic tissue culture cells may also be used for the recombinant production of the MCP1 or multimer or fusion thereof of the invention. Higher eukaryotic tissue culture cell line can be used, including insect baculovirus expression systems and mammalian cells. Transformation or transfection and propagation of such cells have become a routine procedure. Examples of useful cell lines include HeLa cells, Chinese hamster ovary (CHO) cell lines, HEK 293 cells, myeloma cells, J774 cells, Caco2 cells, baby rat kidney (BRK) cell lines, insect cell lines, bird cell lines, and monkey (COS) cell lines. Typically, expression vectors for such cell lines include an origin of replication, a promoter, a translation initiation site, RNA splice sites (if genomic DNA is used), a polyadenylation site, and a transcription termination site. These vectors also, usually, contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Examples of expression vectors include pCR®3.1, pcDNA1, pCD (Okayama, et al., (1985) Mol. Cell. Biol. 5:1136), pMC1neo Poly-A (Thomas, et al., (1987) Cell 51:503), pREP8, pSVSPORT and derivatives thereof, and baculovirus vectors such as pAC373 or pAC610.

In an embodiment of the invention, the MCP1-Ig can be purified by protein A or protein G chromatography. Protein A and protein G bind preferentially to immunoglobulins. Furthermore, the polypeptide can be purified by standard methods, including, but not limited to, salt or alcohol precipitation, affinity chromatography, preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in "Guide to Protein Purification", Methods in Enzymology, Vol. 182, M. Deutscher, Ed., 1990, Academic Press, New York, N.Y. Where a polypeptide is being isolated from a cellular or tissue source, it is preferable to include one or more inhibitors of proteolytic enzymes in the assay system, such as phenylmethanesulfonyl fluoride (PMSF), Pefabloc SC, pepstatin, leupeptin, chymostatin and EDTA.

Modifications (e.g., post-translational modifications) that occur in a polypeptide often will be a function of how it is made. For polypeptides made by expressing a cloned gene in a host, for instance, the nature and extent of the modifications, in large part, will be determined by the host cell's post-translational modification capacity and the modification signals present in the polypeptide amino acid sequence. For instance, as is well known, glycosylation often does not occur in bacterial hosts such as *E. coli*. Accordingly, when glycosylation of MCP1 or the multimer or fusion thereof is desired, the polypeptide can be expressed in a glycosylating host, generally a eukaryotic cell. Insect cells often carry out post-translational glycosylations which are similar to those of mammalian cells. For this reason, insect cell expression systems have been developed to express, efficiently, mammalian proteins having native patterns of glycosylation. An insect cell, which may be used in this invention, is any cell derived from an organism of the class Insecta; for example, where the insect is *Spodoptera fruigiperda* (Sf9 or Sf21) or *Trichoplusia ni* (High 5). Examples of insect expression systems that can be used with the present invention, for example to produce MCP1 or a multimer or fusion thereof, include Bac-To-Bac (Invitrogen Corporation, Carlsbad, Calif.) or Gateway (Invitrogen Corporation, Carlsbad, Calif.). If desired, deglycosylation enzymes can be used to remove carbohydrates attached during production in eukaryotic expression systems.

Pegylation or addition of polyethylene glycol (PEG) to a polypeptide such as MCP1 or a fusion or multimer thereof can be accomplished using conventional and well known methods in the art (see e.g., U.S. Pat. No. 5,691,154; U.S. Pat. No. 5,686,071; U.S. Pat. No. 5,639,633; U.S. Pat. No. 5,492,821; U.S. Pat. No. 5,447,722; U.S. Pat. No. 5,091,176).

The present invention contemplates any superficial or slight modification to the amino acid or nucleotide sequences which correspond to the MCP1 or a multimer or fusion thereof of the invention. In particular, the present invention contemplates sequence conservative variants of the polynucleotides which encode the polypeptides of the invention. "Sequence-conservative variants" of a polynucleotide sequence are those in which a change of one or more nucleotides in a given codon results in no alteration in the amino acid encoded at that position. Function-conservative variants of the polypeptides of the invention are also contemplated by the present invention. "Function-conservative variants" are those in which one or more amino acid residues in a protein or enzyme have been changed without altering the overall conformation and function of the polypeptide, including, but, by no means, limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, proline, tyrosine, phenylalanine, tryptophan and methionine; acidic amino acids which may be interchangeable include aspartic acid and glutamic acid and basic amino acids which may be interchangeable include histidine, lysine and arginine.

The present invention includes polynucleotides encoding an MCP1 (e.g., a mature MCP1 polypeptide), an MCP1 multimer or a fusion thereof (e.g., fused to an in vivo half-life extending moiety (e.g., Ig)) (e.g., any of SEQ ID NOs: 1, 2, 8-12) as well as nucleic acids which hybridize to the polynucleotides. Preferably, the nucleic acids hybridize under low stringency conditions, more preferably under moderate stringency conditions and most preferably under high stringency conditions. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., supra). The conditions of temperature and ionic strength determine the "stringency" of the hybridization. Typical low stringency hybridization conditions are 55° C., 5×SSC, 0.1% SDS, 0.25% milk, and no formamide at 42° C.; or 30% formamide, 5×SSC, 0.5% SDS at 42° C. Typical, moderate stringency hybridization conditions are similar to the low stringency conditions except the hybridization is carried out in 40% formamide, with 5× or 6×SSC at 42° C. High stringency hybridization conditions are similar to low stringency conditions except the hybridization conditions are carried out in 50% formamide, 5× or 6×SSC and, optionally, at a higher temperature (e.g., higher than 42° C.: 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, i.e., oligonucleotides, the position of mismatches becomes more important, and the length of the oligonucleotide determines its specificity (see Sambrook, et al., supra).

Also included in the present invention are polynucleotides comprising nucleotide sequences and polypeptides comprising amino acid sequences which are at least about 70% identical, preferably at least about 80% identical, more preferably at least about 90% identical and most preferably at least about 95% identical (e.g., 95%, 96%, 97%, 98%, 99%, 100%) to the reference MCP1 (e.g., a mature MCP1 polypeptide), MCP1 multimer or fusion thereof (e.g., fused to an in vivo half-life extending moiety (e.g., Ig)) nucleotide sequence of any of SEQ ID NOs: 13 and 19-23 and amino acid sequence of any of SEQ ID NOs: 1, 2, and 8-12 when the comparison is performed by a BLAST algorithm wherein the parameters of the algorithm are selected to give the largest match between the respective sequences over the entire length of the respective reference sequences.

Polypeptides comprising amino acid sequences which are at least about 70% similar, preferably at least about 80% similar, more preferably at least about 90% similar and most preferably at least about 95% similar (e.g., 95%, 96%, 97%, 98%, 99%, 100%) to the reference MCP1 (e.g., a mature MCP1 polypeptide), MCP1 multimer or fusion thereof (e.g., fused to an in vivo half-life extending moiety (e.g., Ig)) of any of SEQ ID NOs: 1, 2 and 8-12, when the comparison is performed with a BLAST algorithm wherein the parameters of the algorithm are selected to give the largest match between the respective sequences over the entire length of the respective reference sequences, are also included in the present invention.

Sequence identity refers to exact matches between the nucleotides or amino acids of two sequences which are being compared. Sequence similarity refers to both exact matches between the amino acids of two polypeptides which are being compared in addition to matches between nonidentical, biochemically related amino acids. Biochemically related amino acids which share similar properties and may be interchangeable are discussed above.

The following references regarding the BLAST algorithm are herein incorporated by reference: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M., et al., (1994) Comput. Appl. Biosci. 10:67-70; ALIGNMENT SCORING SYSTEMS: Dayhoff, M. O., et al., "A model of evolutionary change in proteins." in *Atlas of Protein Sequence and Structure*, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in *Atlas of Protein Sequence and Structure*, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, New York.

Chemokine Ligands and Fusions Thereof

The present invention comprises any fusion polypeptide comprising one or more of any chemokine such as MCP1 polypeptide, fused, optionally by a linker peptide (e.g., GS), to one or more "half-life extending moieties". The invention further comprises any chemokine ligand multimer comprising two or more chemokine polypeptides, or fragments thereof fused into a single continuous polypeptide chain.

In an embodiment of the invention, the chemokine polypeptide is MCP1, SDF1 (including SDF1α or SDF1β; see Genbank accession no. P48061) or MIP1β (see Genbank accession no. NP_002975.1; AAA36656.1; AAA36752.1; AAA51576.1; AAA57256.1; AAB00790.1; AAX07292.1; CAA34291.1; CAA37722.2; CAA37723.1; or CAG46916.1). In an embodiment of the invention, the chemokine polypeptide is any member of the CCL or CXCL class of chemokine, for example, any of CCL1, 2, 3, 4, 5, 6, 7, 8, 9/10, 11, 12, 13, 14, 15, 16, 17, 18, 19, 20, 21, 22, 23, 24, 25, 26, 27 or 28; or any of CXCL 1, 2, 3, 4, 5, 6, 7, 8, 9, 10, 11, 12, 13, 14, 15 or 16. For example, in an embodiment of the invention, the chemokine is any member selected from the group consisting of I309, MIP1α, MIP1β, RANTES, C10, MCP2, MCP3, CCF18, eotaxin1, MCP4, MCP5, HCC1, HCC2, NCC4, TARC, PARK, ELC, LARC, SLC, MDC, MPIF1, eotaxin2, TECK, eotaxin3, ALP, CTACK. For example, in an embodiment of the invention, the chemokine is any member selected from the group consisting of CCL23, CCL28, GROα, GROβ GROγ, PF4, ENA78, GCP2, PBP, β-TG, CTAP-III, NAP-2, IL-8, MIG, IP10, I-TAC, SDF1, BLC, BRAK, lungine, lymphotactin or fractalkine. The present invention comprises fusions comprising more than 1 chemokine fused to a half-life extending moiety (e.g., MCP1-SDF1-Ig).

A "half-life extending moiety" is any moiety, for example, a polypeptide, small molecule or polymer, that, when appended to polypeptide, extends the in vivo half-life of that polypeptide in the body of a subject (e.g., in the plasma of the subject). For example, a half-life extending moiety is, in an embodiment of the invention, polyethylene glycol (PEG), monomethoxy PEG (mPEG) or an immunoglobulin (Ig). In an embodiment of the invention, PEG is a 5, 10, 12, 20, 30, 40 or 50 kDa moiety or larger or comprises about 12000 ethylene glycol units (PEG12000).

The term "Ig" or "immunoglobulin" includes any immunoglobulin from any species, for example from human or from mouse as well as any fragment or variant or mutant thereof. The term includes any heavy chain IgG, for example, IgG1, IgG2, IgG3 or IgG4; IgA, for example, IgA1 or IgA2; IgM, IgD and IgE. In an embodiment of the invention, "Ig" or "immunoglobulin" refers to a polypeptide derived from any of the foregoing from the hinge to the CH3 of the heavy chain. In an embodiment of the invention, "Ig" is a "monomeric variant" or "monomer" of immunoglobulin. A monomeric variant of an immunoglobulin does not dimerize with another immunoglobulin (see e.g., SEQ ID NOs: 5 and 7). A monomeric variant of any immunoglobulin can be constructed by mutation of one or more residues (e.g., cysteine residues) involved in immunoglobulin dimerization. For example, the cysteine residues can be mutated to a serine.

The present invention also provides MCP1 multimers (e.g., (mature or unprocessed MCP1)$_n$ wherein n=2, 3, 4, 5, 6, 7, 8, 9 or 10 or more). An MCP1 multimer comprises one or more MCP1 polypeptides or mature polypeptides thereof fused to one or more other MCP1 polypeptides or mature polypeptides thereof.

The term "MCP1" includes any MCP1 gene or protein from any organism (e.g., from any mammal for example human, *Pan troglodytes; Canis familiaris* (see e.g., accession no. P52203); *Gallus gallus; Bos Taurus* (see e.g., accession no. P28291); *Rattus norvegicus* (see e.g., accession no. XP_213425); or *Mus musculus*) or any homologue or fragment thereof (e.g., mature MCP1). MCP1 is described by several synonyms including CCL2, HC11, MCAF, MCP1, MCP1, SCYA2, GDCF-2, SMC-CF, HSMCR30, MGC9434, GDCF-2 and HC11. A mature MCP1 polypeptide lacks the leader sequence that is present in the unprocessed or immature MCP1 polypeptide. The leader sequence can be easily identified by a practitioner of ordinary skill in the art. In an embodiment of the present invention, the MCP1 leader sequence is amino acids 1-23 of SEQ ID NO: 1.

The term "MCP1-Ig" includes any polypeptide comprising one or more MCP1 polypeptides (e.g., human or mouse) or fragments thereof fused, in any way and in any orientation, to one or more immunoglobulin polypeptides or fragments thereof (e.g., human IgG4 or IgG1 or a fragment thereof including only the hinge to CH3 region).

In an embodiment of the invention, an unprocessed polypeptide sequence of human MCP1 comprises the following amino acid sequence:

(SEQ ID NO: 1)
MKVSAALLCLLLIAATFIPQGLAQPDAINAPVTCCYNFTNRKISVQRLAS

YRRITSSKCPKEAVIFKTIVAKEICADPKQKWVQDSMDHLDKQTQTPKT.

In an embodiment of the invention, a mature polypeptide sequence of human MCP1 comprises the following amino acid sequence:

(SEQ ID NO: 2)
QPDAINAPVTCCYNFTNRKISVQRLASYRRITSSKCPKEAVIFKTIVAK

EICADPKQKWVQDSMDHLDKQTQTPKT.

In an embodiment of the invention, mature MCP1 is amino acids 30-99 of SEQ ID NO: 1. In an embodiment of the invention, mature MCP1 comprises the amino acids sequence of SEQ ID NO: 2 wherein a pyroglutamic acid is added to the N-terminus and in another embodiment of the invention, the mature MCP1 comprises the amino acid sequence of SEQ ID NO: 2 wherein the N-terminal glutamine (Q) is replaced with pyroglutamic acid.

In an embodiment of the invention, mouse MCP1 comprises the amino acid sequence disclosed under UniProtKB/Swiss-Prot accession no. P10148 or under accession no. NP_035463 or IPI00108087.1. Embodiments of the invention also include mature, processed versions of these polypeptides (e.g., wherein signal peptide amino acids 1-23 are removed). In an embodiment of the invention, the mouse MCP1 comprises the amino acid sequence:

(SEQ ID NO: 30)
mqvpvmllgl lftvagwsih vlaqpdavna pltccysfts kmipmsrles ykritssrcp keavvfvtkl krevcadpkk ewvqtyiknl drnqmrsept tlfktasalr ssaplnvklt rkseanastt fstttsstsv gvtsvtvn In an embodiment of the invention, a mature polypeptide sequence of mouse immunoglobulin heavy chain constant region (hinge to CH3 only), isotype γ1 comprises the amino acid sequence:

(SEQ ID NO: 3)
VPRDCGCKPCICTVPEVSSVFIFPPKPKDVLTITLTPKVTCVVVDISKDD

PEVQFSWFVDDVEVHTAQTKPREEQFNSTFRSVSELPIMHQDWLNGK

EFKCRVNSAAFPAPIEKTISKTKGRPKAPQVYTIPPPKEQMAKDKVSLT

CMITDFFPEDITVEWQWNGQPAENYKNTQPIMDTDGSYFVYSKLNVQK

SNWEAGNTFTCSVLHEGLHNHHTEKSLSHSPGK

In an embodiment of the invention, a mature polypeptide sequence of human immunoglobulin heavy chain constant region (hinge to CH3 only), isotype γ4 comprises the amino acid sequence:

(SEQ ID NO: 4)
ESKYGPPCPSCPAPEFLGGPSVFLFPPKPKDTLMISRTPEVTCVVVDV

SQEDPEVQFNWYVDGVEVHNAKTKPREEQFNSTYRVVSVLTVLHQDW

LNGKEYKCKVSNKGLPSSIEKTISKAKGQPREPQVYTLPPSQEEMTKNQ

VSLTCLVKGFYPSDIAVEWESNGQPENNYKTTPPVLDSDGSFFLYSRLT

VDKSRWQEGNVFSCSVMHEALHNHYTQKSLSLSLGK

In an embodiment of the invention, a mature polypeptide sequence of human immunoglobulin heavy chain constant region (hinge to CH3 only), isotype γ4 monomeric variant (C to S mutations in the hinge underscored) comprises the amino acid sequence:

(SEQ ID NO: 5)
ESKYGPP<u>S</u>PS<u>S</u>PAPEFLGGPSVFLFPPKPKDTLMISRTPEVTCVVVDV

SQEDPEVQFNWYVDGVEVHNAKTKPREEQFNSTYRVVSVLTVLHQDW

LNGKEYKCKVSNKGLPSSIEKTISKAKGQPREPQVYTLPPSQEEMTKNQ

VSLTCLVKGFYPSDIAVEWESNGQPENNYKTTPPVLDSDGSFFLYSRLT

VDKSRWQEGNVFSCSVMHEALHNHYTQKSLSLSLGK

In an embodiment of the invention, a mature polypeptide sequence of human immunoglobulin heavy chain constant region (hinge to CH3 only), isotype γ1 comprises the amino acid sequence:

(SEQ ID NO: 6)
VEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPGK

In an embodiment of the invention, a mature polypeptide sequence of human immunoglobulin heavy chain constant region (hinge to CH3 only), isotype γ1 monomeric variant (C to S mutations in the hinge underscored)

(SEQ ID NO: 7)
VEPKS<u>S</u>DKTHT<u>S</u>PP<u>S</u>PAPELLGGPSVFLFPPKPKDTLMISRTPEVTCVV

VDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELTK

NQVSLTCLVKGFYPSDIAVEWESNGQPENNYKTTPPVLDSDGSFFLYSK

LTVDKSRWQQGNVFSCSVMHEALHNHYTQKSLSLSPGK

In an embodiment of the invention, a polypeptide sequence of mature human MCP1 fused to mouse IgG1 (linker underscored) comprises the amino acid sequence:

(SEQ ID NO: 8)
QPDAINAPVTCCYNFTNRKISVQRLASYRRITSSKCPKEAVIFKTIVAKE

ICADPKQKWVQDSMDHLDKQTQTPKT<u>GS</u>VPRDCGCKPCICTVPEVSS

VFIFPPKPKDVLTITLTPKVTCVVVDISKDDPEVQFSWFVDDVEVHTAQ

TKPREEQFNSTFRSVSELPIMHQDWLNGKEFKCRVNSAAFPAPIEKTIS

```
                                                   -continued
KTKGRPKAPQVYTIPPPKEQMAKDKVSLTCMITDFFPEDITVEWQWNGQ

PAENYKNTQPIMDTDGSYFVYSKLNVQKSNWEAGNTFTCSVLHEGLHNH

HTEKSLSHSPGK
```

In an embodiment of the invention, a polypeptide sequence of mature human MCP1 fused to human IgG4 (linker underscored) comprises the amino acid sequence:

```
                                             (SEQ ID NO: 9)
QPDAINAPVTCCYNFTNRKISVQRLASYRRITSSKCPKEAVIFKTIVAKE

ICADPKQKWVQDSMDHLDKQTQTPKTGSESKYGPPCPSCPAPEFLGGP

SVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEKT

ISKAKGQPREPQVYTLPPSQEEMTKNQVSLTCLVKGFYPSDIAVEWESN

GQPENNYKTTPPVLDSDGSFFLYSRLTVDKSRWQEGNVFSCSVMHEAL

HNHYTQKSLSLSLGK
```

In an embodiment of the invention, a polypeptide sequence of mature human MCP1 fused to human IgG4 monomeric variant (linker underscored) comprises the amino acid sequence:

```
                                            (SEQ ID NO: 10)
QPDAINAPVTCCYNFTNRKISVQRLASYRRITSSKCPKEAVIFKTIVAKE

ICADPKQKWVQDSMDHLDKQTQTPKTGSESKYGPPSPSSPAPEFLG

GPSVFLFPPKPKDTLMISRTPEVTCVVVDVSQEDPEVQFNWYVDGV

EVHNAKTKPREEQFNSTYRVVSVLTVLHQDWLNGKEYKCKVSNKGL

PSSIEKTISKAKGQPREPQVYTLPPSQEEMTKNQVSLTCLVKGFYPSD

IAVEWESNGQPENNYKTTPPVLDSDGSFFLYSRLTVDKSRWQEGNV

FSCSVMHEALHNHYTQKSLSLSLGK
```

In an embodiment of the invention, a polypeptide sequence of mature human MCP1 fused to human IgG1 (linker underscored) comprises the amino acid sequence:

```
                                            (SEQ ID NO: 11)
QPDAINAPVTCCYNFTNRKISVQRLASYRRITSSKCPKEAVIFKTIVAKE

ICADPKQKWVQDSMDHLDKQTQTPKTGSVEPKSCDKTHTCPPCPA

PELLGGPSVFLFPPKPKDTLMISRTPEVTCVVVDVSHEDPEVKFNW

YVDGVEVHNAKTKPREEQYNSTYRVVSVLTVLHQDWLNGKEYKCKV

SNKALPAPIEKTISKAKGQPREPQVYTLPPSRDELTKNQVSLTCLVKG

FYPSDIAVEWESNGQPENNYKTTPPVLDSDGSFFLYSKLTVDKSRW

QQGNVFSCSVMHEALHNHYTQKSLSLSPGK
```

In an embodiment of the invention, a polypeptide sequence of human MCP1 fused to human IgG1 monomeric variant (linker underscored) comprises the amino acid sequence:

```
                                            (SEQ ID NO: 12)
QPDAINAPVTCCYNFTNRKISVQRLASYRRITSSKCPKEAVIFKTIVAKE

ICADPKQKWVQDSMDHLDKQTQTPKTGSVEPKSSDKTHTSPPSPA

PELLGGPSVFLFPPKPKDTLMISRTPEVTCVVVDVSHEDPEVKFNW

YVDGVEVHNAKTKPREEQYNSTYRVVSVLTVLHQDWLNGKEYKCK

VSNKALPAPIEKTISKAKGQPREPQVYTLPPSRDELTKNQVSLTCLV

KGFYPSDIAVEWESNGQPENNYKTTPPVLDSDGSFFLYSKLTVDKS

RWQQGNVFSCSVMHEALHNHYTQKSLSLSPGK
```

In an embodiment of the invention, a DNA sequence of human MCP1 coding region comprises the nucleotide sequence (the initiation and the stop codons in underscored; codon of the first amino acid of the mature polypeptide in bold font):

```
                                            (SEQ ID NO: 13)
atgaaagtctctgccgcccttctgtgcctgctgctcatagcagccacctt cattccccaagggctcgctcagccagatgcaatcaatgcccagtc acctgctgttataacttcaccaataggaagatctcagtgcagaggctc gcgagctatagaagaatcaccagcagcaagtgtcccaagaagc tgtgatcttcaagaccattgtggccaaggagatctgtgctgacccaa gcagaagtgggttcaggattccatggaccacctggacaagcaaac ccaaactccgaagacttga
```

In an embodiment of the invention, a DNA sequence of mouse heavy-chain immunoglobulin constant region, γ1 isotype, starting from the amino terminus of the hinge region and ending at the carboxy-terminus of the CH3 region (stop codon in underscored) comprises the nucleotide sequence:

```
                                            (SEQ ID NO: 14)
gtgcccagggattgtggttgtaagccttgcatatgtacagtcccagaag tatcatctgtcttcatcttccccccaaagcccaaggatgtgctcaccatt actctgactcctaaggtcacgtgtgttgtggtagacatcagcaaggat gatcccgaggtccagttcagctggtttgtagatgatgtggaggtgcac acagctcagacaaaacccgggaggagcagttcaacagcactttc cgttcagtcagtgaacttcccatcatgcaccaggactggctcaatggc aaggagttcaaatgcagggtcaacagtgcagctttccctgcccccat cgagaaaaccatctccaaaaccaaaggcagaccgaaggctcca caggtgtacaccattccacctcccaaggagcagatggccaaggat aaagtcagtctgacctgcatgataacagacttcttccctgaagacatt actgtggagtggcagtggaatgggcagccagcggagaactacaa gaacactcagcccatcatggacacagatggctcttacttcgtctaca gcaagctcaatgtgcagaagagcaactgggaggcaggaaatac tttcacctgctctgtgttacatgagggcctgcacaaccaccatactga gaagagcctctcccactctcctggtaaatga
```

In an embodiment of the invention, a DNA sequence of human heavy-chain immunoglobulin constant region, γ4 isotype, starting from the amino terminus of the hinge region and ending at the carboxy-terminus of the CH3 region (stop codon underscored) comprises the nucleotide sequence:

(SEQ ID NO: 15)
gagtccaaatatggtcccccatgcccatcatgcccagcacctgag ttcctgggggggaccatcagtcttcctgttcccccaaaacccaagg acactctcatgatctcccggacccctgaggtcacgtgcgtggtggt ggacgtgagccaggaagaccccgaggtccagttcaactggtac gtggatggcgtggaggtgcataatgccaagacaaagccgcgg gaggagcagttcaacagcacgtaccgtgtggtcagcgtcctcacc gtcctgcaccaggactggctgaacggcaaggagtacaagtgca aggtctccaacaaaggcctcccgtcctccatcgagaaaaccatc tccaaagccaaagggcagccccgagagccacaggtgtacacc ctgcccccatcccaggaggagatgaccaagaaccaggtcagcc -continued tgacctgcctggtcaaaggcttctacccagcgacatcgccgtgga gtgggagagcaatgggcagccggagaacaactacaagaccac gcctcccgtgctggactccgacggctccttcttcctctacagcaggct aaccgtggacaagagcaggtggcaggaggggaatgtcttctcat gctccgtgatgcatgaggctctgcacaaccactacacacagaag agcctctccctgtctctgggtaaa<u>tga</u>

In an embodiment of the invention, a DNA sequence of human heavy-chain immunoglobulin constant region, γ4 isotype, monomeric variant, starting from the amino terminus of the hinge region and ending at the carboxy-terminus of the CH3 region (Cys to Ser changes marked underscored; stop codon in bold font) comprises the nucleotide sequence:

(SEQ ID NO: 16)
gagtccaaatatggtccccca<u>tct</u>ccatca<u>tct</u>ccagcacctgagttcctgggggacca tcagtcttcctgttcccccaaaacccaaggacactctcatgatctcccggacccctgag gtcacgtgcgtggtggtggacgtgagccaggaagaccccgaggtccagttcaactggtac gtggatggcgtggaggtgcataatgccaagacaaagccgcgggaggagcagttcaacagc acgtaccgtgtggtcagcgtcctcaccgtcctgcaccaggactggctgaacggcaaggag tacaagtgcaaggtctccaacaaaggcctcccgtcctccatcgagaaaaccatctccaaa gccaaagggcagccccgagagccacaggtgtacaccctgcccccatcccaggaggagatg accaagaaccaggtcagcctgacctgcctggtcaaaggcttctacccagcgacatcgcc gtggagtgggagagcaatgggcagccggagaacaactacaagaccacgcctcccgtgctg gactccgacggctccttcttcctctacagcaggctaaccgtggacaagagcaggtggcag gaggggaatgtcttctcatgctccgtgatgcatgaggctctgcacaaccactacacacag aagagcctctccctgtctctgggtaaatga

The codon coding for serine, in any immunoglobulin monomeric variant set forth herein wherein one or more cysteines have been mutated, can be any codon that encodes the serine amino acid; for example, AGT, AGC, TCT, TCC, TCA or TCG.

In an embodiment of the invention, a DNA sequence of human heavy-chain immunoglobulin constant region, γ1 isotype, starting from the amino terminus of the hinge region and ending at the carboxy-terminus of the CH3 region (stop codon underscored) comprises the nucleotide sequence:

(SEQ ID NO: 17)
gttgagcccaaatcttgtgacaaaactcacacatgcccaccgtgcccagcacctgaactc ctgggggaccgtcagtcttcctcttcccccaaaacccaaggacaccctcatgatctcc cggacccctgaggtcacatgcgtggtggtggacgtgagccacgaagaccctgaggtcaag ttcaactggtacgtggacggcgtggaggtgcataatgccaagacaaagccgcgggaggag cagtacaacagcacgtaccgtgtggtcagcgtcctcaccgtcctgcaccaggactggctg aatggcaaggagtacaagtgcaaggtctccaacaaagccctcccagcccccatcgagaaa accatctccaaagccaaagggcagccccgagaaccacaggtgtacaccctgcccccatcc cgggatgagctgaccaagaaccaggtcagcctgacctgcctggtcaaaggcttctatccc agcgacatcgccgtggagtgggagagcaatgggcagccggagaacaactacaagaccacg -continued

```
cctcccgtgctggactccgacggctccttcttcctctacagcaagctcaccgtggacaag agcaggtggcagcaggggaacgtcttctcatgctccgtgatgcatgaggctctgcacaac cactacacgcagaagagcctctccctgtctccgggtaaatga
```

In an embodiment of the invention, a DNA sequence of human heavy-chain immunoglobulin constant region, γ1 isotype, monomeric variant, starting from the amino terminus of the hinge region and ending at the carboxy-terminus of the CH3 region (Cys to Ser changes underscored; stop codon in bold font) comprises the nucleotide sequence:

```
                                                (SEQ ID NO: 18)
gttgagcccaaatcttctgacaaaactcacacatctccaccgtctccagcacctgaactc ctgggggaccgtcagtcttcctcttccccccaaaacccaaggacaccctcatgatctcc cggacccctgaggtcacatgcgtggtggtggacgtgagccacgaagaccctgaggtcaag ttcaactggtacgtggacggcgtggaggtgcataatgccaagacaaagccgcgggaggag cagtacaacagcacgtaccgtgtggtcagcgtcctcaccgtcctgcaccaggactggctg aatggcaaggagtacaagtgcaaggtctccaacaaagccctcccagcccccatcgagaaa accatctccaaagccaaagggcagccccgagaaccacaggtgtacaccctgcccccatcc cgggatgagctgaccaagaaccaggtcagcctgacctgcctggtcaaaggcttctatccc agcgacatcgccgtggagtgggagagcaatgggcagccggagaacaactacaagaccacg cctcccgtgctggactccgacggctccttcttcctctacagcaagctcaccgtggacaag agcaggtggcagcaggggaacgtcttctcatgctccgtgatgcatgaggctctgcacaac cactacacgcagaagagcctctccctgtctccgggtaaatga
```

In an embodiment of the invention, a cDNA of human MCP1 (including the leader peptide) fused to mouse IgG1 comprises the nucleotide sequence:

```
                                                (SEQ ID NO: 19)
atgaaagtctctgccgcccttctgtgcctgctgctcatagcagccaccttcattccccaa gggctcgctcagccagatgcaatcaatgccccagtcacctgctgttataacttcaccaat aggaagatctcagtgcagaggctcgcgagctatagaagaatcaccagcagcaagtgtccc aaagaagctgtgatcttcaagaccattgtggccaaggagatctgtgctgaccccaagcag aagtgggttcaggattccatggaccacctggacaagcaaacccaaactccgaagactgga tccgtgcccagggattgtggttgtaagccttgcatatgtacagtcccagaagtatcatct gtcttcatcttccccccaaagcccaaggatgtgctcaccattactctgactcctaaggtc acgtgtgttgtggtagacatcagcaaggatgatcccgaggtccagttcagctggtttgta gatgatgtggaggtgcacacagctcagacaaaacccggggaggagcagttcaacagcact ttccgttcagtcagtgaacttcccatcatgcaccaggactggctcaatggcaaggagttc aaatgcagggtcaacagtgcagctttccctgcccccatcgagaaaaccatctccaaaacc aaaggcagaccgaaggctccacaggtgtacaccattccacctcccaaggagcagatggcc aaggataaagtcagtctgacctgcatgataacagacttattccctgaagacattactgtg gagtggcagtggaatgggcagccagcggagaactacaagaacactcagcccatcatggac acagatggctcttacttcgtctacagcaagctcaatgtgcagaagagcaactgggaggca ggaaatactttcacctgctctgtgttacatgagggcctgcacaaccaccatactgagaag agcctctcccactctcctggtaaatga
```

In an embodiment of the invention cDNA of human MCP1 (including the leader peptide) fused to human IgG4 comprises the nucleotide sequence:

(SEQ ID NO: 20)
```
atgaaagtctctgccgcccttctgtgcctgctgctcatagcagccaccttcattccccaa
gggctcgctcagccagatgcaatcaatgccccagtcacctgctgttataacttcaccaat
aggaagatctcagtgcagaggctcgcgagctatagaagaatcaccagcagcaagtgtccc
aaagaagctgtgatcttcaagaccattgtggccaaggagatctgtgctgaccccaagcag
aagtgggttcaggattccatggaccacctggacaagcaaacccaaactccgaagactgga
tccgagtccaaatatggtcccccatgcccatcatgcccagcacctgagttcctggggga
ccatcagtcttcctgttccccccaaaacccaaggacactctcatgatctcccggacccct
gaggtcacgtgcgtggtggtggacgtgagccaggaagaccccgaggtccagttcaactgg
tacgtggatggcgtggaggtgcataatgccaagacaaagccgcgggaggagcagttcaac
agcacgtaccgtgtggtcagcgtcctcaccgtcctgcaccaggactggctgaacggcaag
gagtacaagtgcaaggtctccaacaaaggcctcccgtcctccatcgagaaaaccatctcc
aaagccaaagggcagccccgagagccacaggtgtacaccctgcccccatcccaggaggag
atgaccaagaaccaggtcagcctgacctgcctggtcaaaggcttctaccccagcgacatc
gccgtggagtgggagagcaatgggcagccggagaacaactacaagaccacgcctcccgtg
ctggactccgacggctccttcttcctctacagcaggctaaccgtggacaagagcaggtgg
caggaggggaatgtcttctcatgctccgtgatgcatgaggctctgcacaaccactacaca
cagaagagcctctccctgtctctgggtaaatga
```

In an embodiment of the invention, a cDNA of human MCP1 (including the leader sequence) fused to human IgG4 monomeric variant comprises the nucleotide sequence:

(SEQ ID NO: 21)
```
atgaaagtctctgccgcccttctgtgcctgctgctcatagcagccaccttcattccccaa
gggctcgctcagccagatgcaatcaatgccccagtcacctgctgttataacttcaccaat
aggaagatctcagtgcagaggctcgcgagctatagaagaatcaccagcagcaagtgtccc
aaagaagctgtgatcttcaagaccattgtggccaaggagatctgtgctgaccccaagcag
aagtgggttcaggattccatggaccacctggacaagcaaacccaaactccgaagactgga
tccgagtccaaatatggtcccccatctccatcatctccagcacctgagttcctggggga
ccatcagtcttcctgttccccccaaaacccaaggacactctcatgatctcccggacccct
gaggtcacgtgcgtggtggtggacgtgagccaggaagaccccgaggtccagttcaactgg
tacgtggatggcgtggaggtgcataatgccaagacaaagccgcgggaggagcagttcaac
agcacgtaccgtgtggtcagcgtcctcaccgtcctgcaccaggactggctgaacggcaag
gagtacaagtgcaaggtctccaacaaaggcctcccgtcctccatcgagaaaaccatctcc
aaagccaaagggcagccccgagagccacaggtgtacaccctgcccccatcccaggaggag
atgaccaagaaccaggtcagcctgacctgcctggtcaaaggcttctaccccagcgacatc
gccgtggagtgggagagcaatgggcagccggagaacaactacaagaccacgcctcccgtg
ctggactccgacggctccttcttcctctacagcaggctaaccgtggacaagagcaggtgg
caggaggggaatgtcttctcatgctccgtgatgcatgaggctctgcacaaccactacaca
cagaagagcctctccctgtctctgggtaaatga
```

In an embodiment of the invention, a cDNA of human MCP1 (including the leader sequence) fused to human IgG1 comprises the nucleotide sequence:

(SEQ ID NO: 22)
atgaaagtctctgccgcccttctgtgcctgctgctcatagcagccaccttcattccccaa gggctcgctcagccagatgcaatcaatgccccagtcacctgctgttataacttcaccaat aggaagatctcagtgcagaggctcgcgagctatagaagaatcaccagcagcaagtgtccc aaagaagctgtgatcttcaagaccattgtggccaaggagatctgtgctgaccccaagcag aagtgggttcaggattccatggaccacctggacaagcaaacccaaactccgaagactgga tccgttgagcccaaatcttgtgacaaaactcacacatgcccaccgtgcccagcacctgaa ctcctggggggaccgtcagtcttcctcttccccccaaaacccaaggacaccctcatgatc tcccgacccctgaggtcacatgcgtggtggtggacgtgagccacgaagaccctgaggtc aagttcaactggtacgtggacggcgtggaggtgcataatgccaagacaaagccgcgggag gagcagtacaacagcacgtaccgtgtggtcagcgtcctcaccgtcctgcaccaggactgg ctgaatggcaaggagtacaagtgcaaggtctccaacaaagccctcccagcccccatcgag aaaaccatctccaaagccaaagggcagccccgagaaccacaggtgtacaccctgcccca tcccgggatgagctgaccaagaaccaggtcagcctgacctgcctggtcaaaggcttctat cccagcgacatcgccgtggagtgggagagcaatgggcagccggagaacaactacaagacc acgcctcccgtgctggactccgacggctccttcttcctctacagcaagctcaccgtggac aagagcaggtggcagcaggggaacgtcttctcatgctccgtgatgcatgaggctctgcac aaccactacacgcagaagagcctctccctgtctccgggtaaatga In an embodiment of the invention, a cDNA of human MCP1 (including the leader sequence) fused to human IgG1 monomeric variant comprises the nucleotide sequence:

(SEQ ID NO: 23)
atgaaagtctctgccgcccttctgtgcctgctgctcatagcagccaccttcattccccaa gggctcgctcagccagatgcaatcaatgccccagtcacctgctgttataacttcaccaat aggaagatctcagtgcagaggctcgcgagctatagaagaatcaccagcagcaagtgtccc aaagaagctgtgatcttcaagaccattgtggccaaggagatctgtgctgaccccaagcag aagtgggttcaggattccatggaccacctggacaagcaaacccaaactccgaagactgga tccgttgagcccaaatcttctgacaaaactcacacatctccaccgtctccagcacctgaa ctcctggggggaccgtcagtcttcctcttccccccaaaacccaaggacaccctcatgatc tcccggacccctgaggtcacatgcgtggtggtggacgtgagccacgaagaccctgaggtc aagttcaactggtacgtggacggcgtggaggtgcataatgccaagacaaagccgcgggag gagcagtacaacagcacgtaccgtgtggtcagcgtcctcaccgtcctgcaccaggactgg ctgaatggcaaggagtacaagtgcaaggtctccaacaaagccctcccagcccccatcgag aaaaccatctccaaagccaaagggcagccccgagaaccacaggtgtacaccctgcccca tcccgggatgagctgaccaagaaccaggtcagcctgacctgcctggtcaaaggcttctat cccagcgacatcgccgtggagtgggagagcaatgggcagccggagaacaactacaagacc acgcctcccgtgctggactccgacggctccttcttcctctacagcaagctcaccgtggac aagagcaggtggcagcaggggaacgtcttctcatgctccgtgatgcatgaggctctgcac aaccactacacgcagaagagcctctccctgtctccgggtaaatga In an embodiment of the invention, a sequence of an expression plasmid encoding a fusion proteins comprising mature human MCP1 and mouse IgG, plasmid pcDNA3.1(+) hMCP1 mIgG (the initiation and the stop codons underscored, the codons for the linker of MCP1 and mIg in bold font), comprises the nucleotide sequence:

(SEQ ID NO: 24)

```
gacggatcgggagatctcccgatcccctatggtgcactctcagtacaatctgctctgatg ccgcatagttaagccagtatctgctccctgcttgtgtgttggaggtcgctgagtagtgcg cgagcaaaatttaagctacaacaaggcaaggcttgaccgacaattgcatgaagaatctgc ttagggttaggcgttttgcgctgcttcgcgatgtacgggccagatatacgcgttgacatt gattattgactagttattaatagtaatcaattacggggtcattagttcatagcccatata tggagttccgcgttacataacttacggtaaatggcccgcctggctgaccgcccaacgacc cccgcccattgacgtcaataatgacgtatgttcccatagtaacgccaatagggactttcc attgacgtcaatgggtggagtatttacggtaaactgcccacttggcagtacatcaagtgt atcatatgccaagtacgccccctattgacgtcaatgacggtaaatgcccgcctggcatt atgcccagtacatgaccttatgggactttcctacttggcagtacatctacgtattagtca tcgctattaccatggtgatgcggttttggcagtacatcaatgggcgtggatagcggtttg actcacggggatttccaagtctccacccccattgacgtcaatgggagtttgttttggcacc aaaatcaacgggactttccaaaatgtcgtaacaactccgccccattgacgcaaatgggcg gtaggcgtgtacggtgggaggtctatataagcagagctctctggctaactagagaaccca ctgcttactggcttatcgaaattaatacgactcactatagggagacccaagctggctagc gtttaaacttaagcttacgatcagtcgaattcgccgccaccatgaaagtctctgccgccc ttctgtgcctgctgctcatagcagccaccttcattccccaagggctcgctcagccagatg caatcaatgccccagtcacctgctgttataacttcaccaataggaagatctcagtgcaga ggctcgcgagctatagaagaatcaccagcagcaagtgtcccaaagaagctgtgatcttca agaccattgtggccaaggagatctgtgctgaccccaagcagaagtgggttcaggattcca tggaccacctggacaagcaaacccaaactccgaagactggatccgtgcccagggattgtg gttgtaagccttgcatatgtacagtcccagaagtatcatctgtcttcatcttccccccaa agcccaaggatgtgctcaccattactctgactcctaaggtcacgtgtgttgtggtagaca tcagcaaggatgatcccgaggtccagttcagctggtttgtagatgatgtggaggtgcaca cagctcagacaaaaccccgggaggagcagttcaacagcactttccgttcagtcagtgaac ttcccatcatgcaccaggactggctcaatggcaaggagttcaaatgcagggtcaacagtg cagctttccctgccccatcgagaaaaccatctccaaaaccaaaggcagaccgaaggctc cacaggtgtacaccattccacctcccaaggagcagatggccaaggataaagtcagtctga cctgcatgataacagacttcttccctgaagacattactgtggagtggcagtggaatgggc agccagcggagaactacaagaacactcagcccatcatggacacagatggctcttacttcg tctacagcaagctcaatgtgcagaagagcaactgggaggcaggaaatactttcacctgct ctgtgttacatgagggcctgcacaaccaccatactgagaagagcctctcccactctcctg gtaaatgactagtcatagtttagcggccgctcgagtctagagggcccgtttaaaccgct gatcagcctcgactgtgccttctagttgccagccatctgttgtttgcccctcccccgtgc cttccttgaccctggaaggtgccactcccactgtcctttcctaataaaatgaggaaattg catcgcattgtctgagtaggtgtcattctattctggggggtggggtggggcaggacagca agggggaggattgggaagacaatagcaggcatgctggggatgcggtgggctctatggctt ctgaggcggaaagaaccagctggggctctagggggtatccccacgcgccctgtagcggcg
```

-continued

```
cattaagcgcggcgggtgtggtggttacgcgcagcgtgaccgctacacttgccagcgccc tagcgcccgctcctttcgctttattcccttcctttctcgccacgttcgccggctttcccc gtcaagctctaaatcgggggctccctttagggttccgatttagtgctttacggcacctcg accccaaaaaacttgattagggtgatggttcacgtagtgggccatcgccctgatagacgg tttttcgcccttttgacgttggagtccacgttctttaatagtggactcttgttccaaactg gaacaacactcaaccctatctcggtctattcttttgatttataagggattttgccgattt cggcctattggttaaaaaatgagctgatttaacaaaaatttaacgcgaattaattctgtg gaatgtgtgtcagttagggtgtggaaagtccccaggctccccagcaggcagaagtatgca aagcatgcatctcaattagtcagcaaccaggtgtggaaagtccccaggctccccagcagg cagaagtatgcaaagcatgcatctcaattagtcagcaaccatagtcccgcccctaactcc gcccatcccgcccctaactccgcccagttccgcccattctccgcccatggctgactaat tttttttatttatgcagaggccgaggccgcctctgcctctgagctattccagaagtagtg aggaggcttttttggaggcctaggcttttgcaaaaagctcccgggagcttgtatatccat tttcggatctgatcaagagacaggatgaggatcgtttcgcatgattgaacaagatggatt gcacgcaggttctccggccgcttgggtggagaggctattcggctatgactgggcacaaca gacaatcggctgctctgatgccgccgtgttccggctgtcagcgcaggggcgcccggttct ttttgtcaagaccgacctgtccggtgccctgaatgaactgcaggacgaggcagcgcggct atcgtggctggccacgacgggcgttccttgcgcagctgtgctcgacgttgtcactgaagc gggaagggactggctgctattgggcgaagtgccggggcaggatctcctgtcatctcacct tgctcctgccgagaaagtatccatcatggctgatgcaatgcggcggctgcatacgcttga tccggctacctgcccattcgaccaccaagcgaaacatcgcatcgagcgagcacgtactcg gatggaagccggtcttgtcgatcaggatgatctggacgaagagcatcaggggctcgcgcc agccgaactgttcgccaggctcaaggcgcgcatgcccgacggcgaggatctcgtcgtgac ccatggcgatgcctgcttgccgaatatcatggtggaaaatggccgcttttctggattcat cgactgtggccggctgggtgtggcggaccgctatcaggacatagcgttggctacccgtga tattgctgaagagcttggcggcgaatgggctgaccgcttcctcgtgctttacggtatcgc cgctcccgattcgcagcgcatcgccttctatcgccttcttgacgagttcttctgagcggg actctggggttcgaaatgaccgaccaagcgacgcccaacctgccatcacgagatttcgat tccaccgccgccttctatgaaaggttgggcttcggaatcgttttccgggacgccggctgg atgatcctccagcgcggggatctcatgctggagttcttcgcccacccccaacttgtttatt gcagcttataatggttacaaataaagcaatagcatcacaaatttcacaaataaagcattt ttttcactgcattctagttgtggtttgtccaaactcatcaatgtatcttatcatgtctgt ataccgtcgacctctagctagagcttggcgtaatcatggtcatagctgtttcctgtgtga aattgttatccgctcacaattccacacaacatacgagccggaagcataaagtgtaaagcc tggggtgcctaatgagtgagctaactcacattaattgcgttgcgctcactgcccgctttc cagtcgggaaacctgtcgtgccagctgcattaatgaatcggccaacgcgcgggagaggc ggtttgcgtattgggcgctcttccgcttcctcgctcactgactcgctgcgctcggtcgtt cggctgcggcgagcggtatcagctcactcaaaggcggtaatacggttatccacagaatca ggggataacgcaggaaagaacatgtgagcaaaaggccagcaaaaggccaggaaccgtaaa aaggccgcgttgctggcgttttttccataggctccgcccccctgacgagcatcacaaaaat
```

-continued
```
cgacgctcaagtcagaggtggcgaaacccgacaggactataaagataccaggcgtttccc cctggaagctccctcgtgcgctctcctgttccgaccctgccgcttaccggatacctgtcc gcctttctcccttcgggaagcgtggcgcttcctcatagctcacgctgtaggtatctcagt tcggtgtaggtcgttcgctccaagctgggctgtgtgcacgaaccccccgttcagcccgac cgctgcgccttatccggtaactatcgtcttgagtccaacccggtaagacacgacttatcg ccactggcagcagccactggtaacaggattagcagagcgaggtatgtaggcggtgctaca gagttcttgaagtggtggcctaactacggctacactagaagaacagtatttggtatctgc gctctgctgaagccagttaccttcggaaaaagagttggtagctcttgatccggcaaacaa accaccgctggtagcggttttttttgtttgcaagcagcagattacgcgcagaaaaaaagga tctcaagaagatcctttgatcttttctacggggtctgacgctcagtggaacgaaaactca cgttaagggatttttggtcatgagattatcaaaaaggatcttcacctagatccttttaaat taaaaatgaagttttaaatcaatctaaagtatatatgagtaaacttggtctgacagttac caatgcttaatcagtgaggcacctatctcagcgatctgtctatttcgttcatccatagtt gcctgactccccgtcgtgtagataactacgatacgggagggcttaccatctggcccagt gctgcaatgataccgcgagacccacgctcaccggctccagatttatcagcaataaaccag ccagccggaagggccgagcgcagaagtggtcctgcaactttatccgcctccatccagtct attaattgttgccgggaagctagagtaagtagttcgccagttaatagtttgcgcaacgtt gttgccattgctacaggcatcgtggtgtcacgctcgtcgtttggtatggcttcattcagc tccggttcccaacgatcaaggcgagttacatgatcccccatgttgtgcaaaaaagcggtt agctccttcggtcctccgatcgttgtcagaagtaagttggccgcagtgttatcactcatg gttatggcagcactgcataattctcttactgtcatgccatccgtaagatgcttttctgtg actggtgagtactcaaccaagtcattctgagaatagtgtatgcggcgaccgagttgctct tgcccggcgtcaatacgggataataccgcgccacatagcagaactttaaaagtgctcatc attggaaaacgttcttcggggcgaaaactctcaaggatcttaccgctgttgagatccagt tcgatgtaacccactcgtgcacccaactgatcttcagcatcttttactttcaccagcgtt tctgggtgagcaaaaacaggaaggcaaaatgccgcaaaaaagggaataagggcgacacgg aaatgttgaatactcatactcttcctttttcaatattattgaagcatttatcagggttat tgtctcatgagcggatacatatttgaatgtatttagaaaaataaacaatagggttccg cgcacatttccccgaaaagtgccacctgacgtc
```

The fusions of the invention comprise one or more MCP1s and one or more half-life extending moieties (e.g., immunoglobulins) in any order, repeated any number of times. If the fusion comprises multiple MCP1s, the MCP1s may be the same or different. For example, a fusion of the invention comprises, in an embodiment, human MCP1-mouse MCP1-Ig. Multiple immunoglobulin polypeptides may also be included in a fusion of the invention. For example, in an embodiment, the fusion comprises human MCP1-human MCP1-IgG1-IgG1; human MCP1-human MCP1-IgG1-IgG4; or human MCP1-Ig-mouse MCP1-Ig-Ig-human MCP1. Any of these embodiments are included under the term "MCP1-Ig". The present invention also includes e.g., (human MCP1)$_2$-PEG or mouse MCP1-human MCP1-PEG Fusions comprising MCP1 at the amino-terminus are within the scope of the present invention along with fusions with MCP1 at the carboxy-terminus; the term MCP1-Ig refers to both of these types of fusions. For example, the present invention comprises any of the following MCP1-Ig fusions: human MCP1-Ig, Ig-human MCP1, mouse MCP1-Ig, Ig-mouse MCP1; PEG-human MCP1 or human MCP1-PEG.

In an embodiment of the invention, an MCP1-Ig fusion of the invention comprises a linker (e.g., a peptide linker) linking the MCP1 with the Ig. In an embodiment of the invention, the linker comprises 1, 2, 3, 4, 5, 6, 7, 8, 9 or 10 amino acids.

In addition to pcDNA3.1(+) hMCP1 mIgG, the following plasmids form part of the present invention. Plasmid pcDNA3.1(+) hMCP1 hIgG4 (the initiation and the stop codons in underscored text, the codons for the linker of MCP-1 and mIg in bold text):

(SEQ ID NO: 25)

gacggatcgggagatctcccgatccctatggtgcactctcagtacaatctgctctgatg
ccgcatagttaagccagtatctgctccctgcttgtgtgttggaggtcgctgagtagtgcg
cgagcaaaatttaagctacaacaaggcaaggcttgaccgacaattgcatgaagaatctgc
ttagggttaggcgttttgcgctgcttcgcgatgtacgggccagatatacgcgttgacatt
gattattgactagttattaatagtaatcaattacggggtcattagttcatagcccatata
tggagttccgcgttacataacttacggtaaatggcccgcctggctgaccgcccaacgacc
cccgcccattgacgtcaataatgacgtatgttcccatagtaacgccaatagggactttcc
attgacgtcaatgggtggagtatttacggtaaactgcccacttggcagtacatcaagtgt
atcatatgccaagtacgccccctattgacgtcaatgacggtaaatggcccgcctggcatt
atgcccagtacatgaccttatgggactttcctacttggcagtacatctacgtattagtca
tcgctattaccatggtgatgcggttttggcagtacatcaatgggcgtggatagcggtttg
actcacggggatttccaagtctccaccccattgacgtcaatgggagtttgttttggcacc
aaaatcaacgggactttccaaaatgtcgtaacaactccgccccattgacgcaaatgggcg
gtaggcgtgtacggtgggaggtctatataagcagagctctctggctaactagagaaccca
ctgcttactggcttatcgaaattaatacgactcactatagggagacccaagctggctagc
gtttaaacttaagcttacgatcagtcgaattcgccgccacc<u>atg</u>aaagtctctgccgccc
ttctgtgcctgctgctcatagcagccaccttcattccccaagggctcgctcagccagatg
caatcaatgccccagtcacctgctgttataacttcaccaataggaagatctcagtgcaga
ggctcgcgagctatagaagaatcaccagcagcaagtgtcccaaagaagctgtgatcttca
agaccattgtggccaaggagatctgtgctgacccaagcagaagtgggttcaggattcca
tggaccacctggacaagcaaacccaaactccgaagactggatccgagtccaaatatggtc
ccccatgcccatcatgcccagcacctgagttcctggggggaccatcagtcttcctgttcc
ccccaaaacccaaggacactctcatgatctcccggacccctgaggtcacgtgcgtggtgg
tggacgtgagccaggaagaccccgaggtccagttcaactggtacgtggatggcgtggagg
tgcataatgccaagacaaagccgcgggaggagcagttcaacagcacgtaccgtgtggtca
gcgtcctcaccgtcctgcaccaggactggctgaacggcaaggagtacaagtgcaaggtct
ccaacaaaggcctcccgtcctccatcgagaaaaccatctccaaagccaaagggcagcccc
gagagccacaggtgtacaccctgcccccatcccaggaggagatgaccaagaaccaggtca
gcctgacctgcctggtcaaaggcttctaccccagcgacatcgccgtggagtgggagagca
atgggcagccggagaacaactacaagaccacgcctcccgtgctggactccgacggctcct
tcttcctctacagcaggctaaccgtggacaagagcaggtggcaggaggggaatgtcttct
catgctccgtgatgcatgaggctctgcacaaccactacacacagaagagcctctccctgt
ctctgggtaaa<u>tga</u>ctagtcatagtttagcggccgctcgagtctagagggcccgtttaaa
cccgctgatcagcctcgactgtgccttctagttgccagccatctgttgtttgcccctccc
ccgtgccttccttgaccctggaaggtgccactcccactgtcctttcctaataaaatgagg
aaattgcatcgcattgtctgagtaggtgtcattctattctggggggtggggtggggcagg
acagcaaggggaggattgggaagacaatagcaggcatgctggggatgcggtgggctcta
tggcttctgaggcggaaagaaccagctggggctctagggggtatccccacgcgccctgta
gcggcgcattaagcgcggcgggtgtggtggttacgcgcagcgtgaccgctacacttgcca
gcgccctagcgcccgctcctttcgctttcttcccttcctttctcgccacgttcgccggct -continued

```
ttccccgtcaagctctaaatcgggggctccctttagggttccgatttagtgctttacggc
acctcgaccccaaaaaacttgattagggtgatggttcacgtagtgggccatcgccctgat
agacggttttcgcccctttgacgttggagtccacgttctttaatagtggactcttgttcc
aaactggaacaacactcaaccctatctcggtctattcttttgatttataagggattttgc
cgatttcggcctattggttaaaaaatgagctgatttaacaaaaatttaacgcgaattaat
tctgtggaatgtgtgtcagttagggtgtggaaagtccccaggctccccagcaggcagaag
tatgcaaagcatgcatctcaattagtcagcaaccaggtgtggaaagtccccaggctcccc
agcaggcagaagtatgcaaagcatgcatctcaattagtcagcaaccatagtcccgcccct
aactccgcccatcccgcccctaactccgcccagttccgcccattctccgcccatggctg
actaattttttttatttatgcagaggccgaggccgcctctgcctctgagctattccagaa
gtagtgaggaggcttttttggaggcctaggcttttgcaaaaagctcccgggagcttgtat
atccattttcggatctgatcaagacaggatgaggatcgtttcgcatgattgaacaaga
tggattgcacgcaggttctccggccgcttgggtggagaggctattcggctatgactgggc
acaacagacaatcggctgctctgatgccgccgtgttccggctgtcagcgcaggggcgccc
ggttcttttgtcaagaccgacctgtccggtgccctgaatgaactgcaggacgaggcagc
gcggctatcgtggctggccacgacgggcgttccttgcgcagctgtgctcgacgttgtcac
tgaagcgggaagggactggctgctattgggcgaagtgccggggcaggatctcctgtcatc
tcaccttgctcctgccgagaaagtatccatcatggctgatgcaatgcggcggctgcatac
gcttgatccggctacctgcccattcgaccaccaagcgaaacatcgcatcgagcgagcacg
tactcggatggaagccggtcttgtcgatcaggatgatctggacgaagagcatcaggggct
cgcgccagccgaactgttcgccaggctcaaggcgcgcatgcccgacggcgaggatctcgt
cgtgacccatggcgatgcctgcttgccgaatatcatggtggaaaatggccgcttttctgg
attcatcgactgtggccggctgggtgtggcggaccgctatcaggacatagcgttggctac
ccgtgatattgctgaagagcttggcggcgaatgggctgaccgcttcctcgtgctttacgg
tatcgccgctcccgattcgcagcgcatcgccttctatcgccttcttgacgagttcttctg
agcgggactctggggttcgaaatgaccgaccaagcgacgcccaacctgccatcacgagat
ttcgattccaccgccgccttctatgaaaggttgggcttcggaatcgttttccgggacgcc
ggctggatgatcctccagcgcggggatctcatgctggagttcttcgcccaccccaacttg
tttattgcagcttataatggttacaaataaagcaatagcatcacaaatttcacaaataaa
gcatttttttcactgcattctagttgtggtttgtccaaactcatcaatgtatcttatcat
gtctgtataccgtcgacctctagctagagcttggcgtaatcatggtcatagctgtttcct
gtgtgaaattgttatccgctcacaattccacacaacatacgagccggaagcataaagtgt
aaagcctggggtgcctaatgagtgagctaactcacattaattgcgttgcgctcactgccc
gctttccagtcgggaaacctgtcgtgccagctgcattaatgaatcggccaacgcgcgggg
agaggcggtttgcgtattgggcgctcttccgcttcctcgctcactgactcgctgcgctcg
gtcgttcggctgcggcgagcggtatcagctcactcaaaggcggtaatacggttatccaca
gaatcaggggataacgcaggaaagaacatgtgagcaaaaggccagcaaaaggccaggaac
cgtaaaaaggccgcgttgctggcgtttttccataggctccgcccccctgacgagcatcac
aaaaatcgacgctcaagtcagaggtggcgaaacccgacaggactataaagataccaggcg
tttccccctggaagctccctcgtgcgctctcctgttccgaccctgccgcttaccggatac
ctgtccgcctttctcccttcgggaagcgtggcgctttctcatagctcacgctgtaggtat
```

-continued

```
ctcagttcggtgtaggtcgttcgctccaagctgggctgtgtgcacgaaccccccgttcag
cccgaccgctgcgccttatccggtaactatcgtcttgagtccaacccggtaagacacgac
ttatcgccactggcagcagccactggtaacaggattagcagagcgaggtatgtaggcggt
gctacagagttcttgaagtggtggcctaactacggctacactagaagaacagtatttggt
atctgcgctctgctgaagccagttaccttcggaaaaagagttggtagctcttgatccggc
aaacaaaccaccgctggtagcggttttttttgtttgcaagcagcagattacgcgcagaaaa
aaaggatctcaagaagatcctttgatcttttctacggggtctgacgctcagtggaacgaa
aactcacgttaagggattttggtcatgagattatcaaaaaggatcttcacctagatcctt
ttaaattaaaaatgaagttttaaatcaatctaaagtatatatgagtaaacttggtctgac
agttaccaatgcttaatcagtgaggcacctatctcagcgatctgtctatttcgttcatcc
atagttgcctgactccccgtcgtgtagataactacgatacgggagggcttaccatctggc
cccagtgctgcaatgataccgcgagacccacgctcaccggctccagatttatcagcaata
aaccagccagccggaagggccgagcgcagaagtggtcctgcaactttatccgcctccatc
cagtctattaattgttgccgggaagctagagtaagtagttcgccagttaatagtttgcgc
aacgttgttgccattgctacaggcatcgtggtgtcacgctcgtcgtttggtatggcttca
ttcagctccggttcccaacgatcaaggcgagttacatgatccccatgttgtgcaaaaaa
gcggttagctccttcggtcctccgatcgttgtcagaagtaagttggccgcagtgttatca
ctcatggttatggcagcactgcataattctcttactgtcatgccatccgtaagatgcttt
tctgtgactggtgagtactcaaccaagtcattctgagaatagtgtatgcggcgaccgagt
tgctcttgcccggcgtcaatacgggataataccgcgccacatagcagaactttaaaagtg
ctcatcattggaaaacgttcttaggggcgaaaactctcaaggatcttaccgctgttgaga
tccagttcgatgtaacccactcgtgcacccaactgatcttcagcatcttttactttcacc
agcgtttctgggtgagcaaaaacaggaaggcaaaatgccgcaaaaaagggaataagggcg
acacggaaatgttgaatactcatactcttccttttcaatattattgaagcatttatcag
ggttattgtctcatgagcggatacatatttgaatgtatttagaaaaataaacaaataggg
gttccgcgcacatttccccgaaaagtgccacctgacgtc
```

Plasmid pcDNA3.1(+) hMCP1 hIgG4 monomeric variant (the initiation and the stop codons in underscored text, the codons for the linker of MCP-1 and mIg in bold text):

```
                                              (SEQ ID NO: 26)
gacggatcgggagatctcccgatcccctatggtgcactctcagtacaatctgctctgatg
ccgcatagttaagccagtatctgctccctgcttgtgtgttggaggtcgctgagtagtgcg
cgagcaaaatttaagctacaacaaggcaaggcttgaccgacaattgcatgaagaatctgc
ttagggttaggcgttttgcgctgcttcgcgatgtacgggccagatatacgcgttgacatt
gattattgactagttattaatagtaatcaattacggggtcattagttcatagcccatata
tggagttccgcgttacataacttacggtaaatggcccgcctggctgaccgcccaacgacc
cccgcccattgacgtcaataatgacgtatgttcccatagtaacgccaatagggactttcc
attgacgtcaatgggtggagtatttacggtaaactgcccacttggcagtacatcaagtgt
atcatatgccaagtacgccccctattgacgtcaatgacggtaaatggcccgcctggcatt
atgcccagtacatgaccttatgggactttcctacttggcagtacatctacgtattagtca
tcgctattaccatggtgatgcggttttggcagtacatcaatgggcgtggatagcggtttg
```

-continued

```
actcacggggatttccaagtctccaccccattgacgtcaatgggagtttgttttggcacc aaaatcaacgggactttccaaaatgtcgtaacaactccgccccattgacgcaaatgggcg gtaggcgtgtacggtgggaggtctatataagcagagctctctggctaactagagaaccca ctgcttactggcttatcgaaattaatacgactcactatagggagacccaagctggctagc gtttaaacttaagcttacgatcagtcgaattcgccgccaccatgaaagtctctgccgccc ttctgtgcctgctgctcatagcagccaccttcattccccaagggctcgctcagccagatg caatcaatgccccagtcacctgctgttataacttcaccaataggaagatctcagtgcaga ggctcgcgagctatagaagaatcaccagcagcaagtgtcccaagaagctgtgatcttca agaccattgtggccaaggagatctgtgctgaccccaagcagaagtgggttcaggattcca tggaccacctggacaagcaaacccaaactccgaagactggatccgagtccaaatatggtc ccccatctccatcatctccagcacctgagttcctgggggaccatcagtattcctgttcc ccccaaaacccaaggacactctcatgatctcccggacccctgaggtcacgtgcgtggtgg tggacgtgagccaggaagaccccgaggtccagttcaactggtacgtggatggcgtggagg tgcataatgccaagacaaagccgcgggaggagcagttcaacagcacgtaccgtgtggtca gcgtcctcaccgtcctgcaccaggactggctgaacggcaaggagtacaagtgcaaggtct ccaacaaaggcctcccgtcctccatcgagaaaaccatctccaaagccaaagggcagcccc gagagccacaggtgtacaccctgcccccatcccaggaggagatgaccaagaaccaggtca gcctgacctgcctggtcaaaggcttctaccccagcgacatcgccgtggagtgggagagca atgggcagccggagaacaactacaagaccacgcctcccgtgctggactccgacggctcct tcttcctctacagcaggctaaccgtggacaagagcaggtggcaggaggggaatgtcttct catgctccgtgatgcatgaggctctgcacaaccactacacacagaagagcctctccctgt ctctgggtaaatgactagtcatagtttagcggccgctcgagtctagagggcccgtttaaa cccgctgatcagcctcgactgtgccttctagttgccagccatctgttgtttgcccctccc ccgtgccttccttgaccctggaaggtgccactcccactgtcctttcctaataaaatgagg aaattgcatcgcattgtctgagtaggtgtcattctattctggggggtggggtggggcagg acagcaaggggaggattgggaagacaatagcaggcatgctggggatgcggtggctcta tggcttctgaggcggaaagaaccagctggggctctagggggtatccccacgcgccctgta gcggcgcattaagcgcggcgggtgtggtggttacgcgcagcgtgaccgctacacttgcca gcgccctagcgcccgctcctttcgctttcttcccttcctttctcgccacgttcgccggct ttccccgtcaagctctaaatcggggggctcccttagggttccgatttagtgctttacggc acctcgaccccaaaaaacttgattagggtgatggttcacgtagtgggccatcgccctgat agacggttttcgccctttgacgttggagtccacgttctttaatagtggactcttgttcc aaactggaacaacactcaaccctatctcggtctattcttttgatttataagggattttgc cgatttcggcctattggttaaaaaatgagctgatttaacaaaaatttaacgcgaattaat tctgtggaatgtgtgtcagttagggtgtggaaagtccccaggctccccagcaggcagaag tatgcaaagcatgcatctcaattagtcagcaaccaggtgtggaaagtccccaggctcccc agcaggcagaagtatgcaaagcatgcatctcaattagtcagcaaccatagtcccgcccct aactccgcccatcccgcccctaactccgcccagttccgcccattctccgccccatggctg actaatttttttatttatgcagaggccgaggccgcctctgcctctgagctattccagaa gtagtgaggaggcttttttggaggcctaggcttttgcaaaaagctccagggagcttgtat atccattttcggatctgatcaagagacaggatgaggatcgtttcgcatgattgaacaaga
```

-continued

```
tggattgcacgcaggttctccggccgcttgggtggagaggctattcggctatgactgggc acaacagacaatcggctgctctgatgccgccgtgttccggctgtcagcgcagggggcgccc ggttcttttgtcaagaccgacctgtccggtgccctgaatgaactgcaggacgaggcagc gcggctatcgtggctggccacgacgggcgttccttgcgcagctgtgctcgacgttgtcac tgaagcgggaagggactggctgctattgggcgaagtgccggggcaggatctcctgtcatc tcaccttgctcctgccgagaaagtatccatcatggctgatgcaatgcggcggctgcatac gcttgatccggctacctgcccattcgaccaccaagcgaaacatcgcatcgagcgagcacg tactcggatggaagccggtcttgtcgatcaggatgatctggacgaagagcatcaggggct cgcgccagccgaactgttcgccaggctcaaggcgcgcatgcccgacggcgaggatctcgt cgtgacccatggcgatgcctgcttgccgaatatcatggtggaaaatggccgcttttctgg attcatcgactgtggccggctgggtgtggcggaccgctatcaggacatagcgttggctac ccgtgatattgctgaagagcttggcggcgaatgggctgaccgcttcctcgtgctttacgg tatcgccgctcccgattcgcagcgcatcgccttctatcgccttcttgacgagttcttctg agcgggactctggggttcgaaatgaccgaccaagcgacgcccaacctgccatcacgagat ttcgattccaccgccgccttctatgaaaggttgggcttcggaatcgttttccgggacgcc ggctggatgatcctccagcgcggggatctcatgctggagttcttcgcccaccccaacttg tttattgcagcttataatggttacaaataaagcaatagcatcacaaatttcacaaataaa gcattttttcactgcattctagttgtggtttgtccaaactcatcaatgtatcttatcat gtctgtataccgtcgacctctagctagagcttggcgtaatcatggtcatagctgtttcct gtgtgaaattgttatccgctcacaattccacacaacatacgagccggaagcataaagtgt aaagcctggggtgcctaatgagtgagctaactcacattaattgcgttgcgctcactgccc gctttccagtcgggaaacctgtcgtgccagctgcattaatgaatcggccaacgcgcgggg agaggcggtttgcgtattgggcgctcttccgcttcctcgctcactgactcgctgcgctcg gtcgttcggctgcggcgagcggtatcagctcactcaaaggcggtaatacggttatccaca gaatcaggggataacgcaggaaagaacatgtgagcaaaaggccagcaaaaggccaggaac cgtaaaaaggccgcgttgctggcgtttttccataggctccgcccccctgacgagcatcac aaaaatcgacgctcaagtcagaggtggcgaaacccgacaggactataaagataccaggcg tttccccctggaagctccctcgtgcgctctcctgttccgaccctgccgcttaccggatac ctgtccgcctttctcccttcgggaagcgtggcgctttctcatagctcacgctgtaggtat ctcagttcggtgtaggtcgttcgctccaagctgggctgtgtgcacgaaccccccgttcag cccgaccgctgcgccttatccggtaactatcgtcttgagtccaacccggtaagacacgac ttatcgccactggcagcagccactggtaacaggattagcagagcgaggtatgtaggcggt gctacagagttcttgaagtggtggcctaactacggctacactagaagaacagtatttggt atctgcgctctgctgaagccagttaccttcggaaaaagagttggtagctcttgatccggc aaacaaaccaccgctggtagcggtttttttgtttgcaagcagcagattacgcgcagaaaa aaaggatctcaagaagatcctttgatcttttctacggggtctgacgctcagtggaacgaa aactcacgttaagggattttggtcatgagattatcaaaaaggatcttcacctagatcctt ttaaattaaaaatgaagttttaaatcaatctaaagtatatatgagtaaacttggtctgac agttaccaatgcttaatcagtgaggcacctatctcagcgatctgtctatttcgttcatcc atagttgcctgactccccgtcgtgtagataactacgatacgggagggcttaccatctggc cccagtgctgcaatgataccgcgagacccacgctcaccggctccagatttatcagcaata
```

-continued

```
aaccagccagccggaagggccgagcgcagaagtggtcctgcaactttatccgcctccatc cagtctattaattgttgccgggaagctagagtaagtagttcgccagttaatagtttgcgc aacgttgttgccattgctacaggcatcgtggtgtcacgctcgtcgtttggtatggcttca ttcagctccggttcccaacgatcaaggcgagttacatgatcccccatgttgtgcaaaaaa gcggttagctccttcggtcctccgatcgttgtcagaagtaagttggccgcagtgttatca ctcatggttatggcagcactgcataattctcttactgtcatgccatccgtaagatgcttt tctgtgactggtgagtactcaaccaagtcattctgagaatagtgtatgcggcgaccgagt tgctcttgcccggcgtcaatacgggataataccgcgccacatagcagaactttaaaagtg ctcatcattggaaaacgttcttcggggcgaaaactctcaaggatcttaccgctgttgaga tccagttcgatgtaacccactcgtgcacccaactgatcttcagcatcttttactttcacc agcgtttctgggtgagcaaaaacaggaaggcaaaatgccgcaaaaaagggaataagggcg acacggaaatgttgaatactcatactattccttttcaatattattgaagcatttatcag ggttattgtctcatgagcggatacatatttgaatgtatttagaaaaataaacaaataggg gttccgcgcacatttccccgaaaagtgccacctgacgtc
```

Plasmid pcDNA3.1(+) hMCP1 hIgG1 (the initiation and the stop codons in underscored text, the codons for the linker of MCP-1 and mIg in bold text):

```
                                              (SEQ ID NO: 27)
gacggatcgggagatctcccgatcccctatggtgcactctcagtacaatctgctctgatg ccgcatagttaagccagtatctgctccctgcttgtgtgttggaggtcgctgagtagtgcg cgagcaaaatttaagctacaacaaggcaaggcttgaccgacaattgcatgaagaatctgc ttagggttaggcgttttgcgctgcttcgcgatgtacgggccagatatacgcgttgacatt gattattgactagttattaatagtaatcaattacggggtcattagttcatagcccatata tggagttccgcgttacataacttacggtaaatggcccgcctggctgaccgcccaacgacc cccgcccattgacgtcaataatgacgtatgttcccatagtaacgccaatagggactttcc attgacgtcaatgggtggagtatttacggtaaactgcccacttggcagtacatcaagtgt atcatatgccaagtacgccccctattgacgtcaatgacggtaaatggcccgcctggcatt atgcccagtacatgaccttatgggactttcctacttggcagtacatctacgtattagtca tcgctattaccatggtgatgcggttttggcagtacatcaatgggcgtggatagcggtttg actcacggggatttccaagtctccaccccattgacgtcaatgggagtttgttttggcacc aaaatcaacgggactttccaaaatgtcgtaacaactccgccccattgacgcaaatgggcg gtaggcgtgtacggtgggaggtctatataagcagagctctctggctaactagagaaccca ctgcttactggcttatcgaaattaatacgactcactatagggagacccaagctggctagc gtttaaacttaagcttacgatcagtcgaattcgccgccacc<u>atg</u>aaagtctctgccgcc ttctgtgcctgctgctcatagcagccaccttcattccccaagggctcgctcagccagatg caatcaatgccccagtcacctgctgttataacttcaccaataggaagatctcagtgcaga ggctcgcgagctatagaagaatcaccagcagcaagtgtcccaaagaagctgtgatcttca agaccattgtggccaaggagatctgtgctgaccccaagcagaagtgggttcaggattcca tggaccacctggacaagcaaacccaaactccgaagactggatccgttgagcccaaatctt gtgacaaaactcacacatgcccaccgtgcccagcacctgaactcctggggggaccgtcag tcttcctcttccccccaaaacccaaggacacccctcatgatctcccggacccctgaggtca
```

-continued

```
catgcgtggtggtggacgtgagccacgaagaccctgaggtcaagttcaactggtacgtgg
acggcgtggaggtgcataatgccaagacaaagccgcgggaggagcagtacaacagcacgt
accgtgtggtcagcgtcctcaccgtcctgcaccaggactggctgaatggcaaggagtaca
agtgcaaggtctccaacaaagccctcccagccccatcgagaaaaccatctccaaagcca
aagggcagccccgagaaccacaggtgtacaccctgcccccatcccgggatgagctgacca
agaaccaggtcagcctgacctgcctggtcaaaggcttctatcccagcgacatcgccgtgg
agtgggagagcaatgggcagccggagaacaactacaagaccacgcctcccgtgctggact
ccgacggctccttcttcctctacagcaagctcaccgtggacaagagcaggtggcagcagg
ggaacgtcttctcatgctccgtgatgcatgaggctctgcacaaccactacacgcagaaga
gcctctccctgtctccgggtaaatgactagtcatagtttagcggccgctcgagtctagag
ggcccgtttaaacccgctgatcagcctcgactgtgccttctagttgccagccatctgttg
tttgcccctcccccgtgccttccttgaccctggaaggtgccactcccactgtcctttcct
aataaaatgaggaaattgcatcgcattgtctgagtaggtgtcattctattctggggggtg
gggtggggcaggacagcaaggggaggattgggaagacaatagcaggcatgctggggatg
cggtgggctctatggcttctgaggcggaaagaaccagctggggctctaggggggtatcccc
acgcgcctgtagcggcgcattaagcgcggcgggtgtggtggttacgcgcagcgtgaccg
ctacacttgccagcgccctagcgcccgctcctttcgctttcttcccttcctttctcgcca
cgttcgccggctttccccgtcaagctctaaatcgggggctcccctttagggttccgattta
gtgctttacggcacctcgaccccaaaaaacttgattagggtgatggttcacgtagtgggc
catcgccctgatagacggtttttcgccctttgacgttggagtccacgttctttaatagtg
gactcttgttccaaactggaacaacactcaaccctatctcggtctattcttttgatttat
aagggattttgccgatttcggcctattggttaaaaaatgagctgatttaacaaaaattta
acgcgaattaattctgtggaatgtgtgtcagttagggtgtggaaagtccccaggctcccc
agcaggcagaagtatgcaaagcatgcatctcaattagtcagcaaccaggtgtggaaagtc
cccaggctccccagcaggcagaagtatgcaaagcatgcatctcaattagtcagcaaccat
agtcccgcccctaactccgcccatcccgcccctaactccgcccagttccgcccattctcc
gccccatggctgactaattttttttatttatgcagaggccgaggccgcctctgcctctga
gctattccagaagtagtgaggaggcttttttggaggcctaggcttttgcaaaaagctccc
gggagcttgtatatccattttcggatctgatcaagagacaggatgaggatcgtttcgcat
gattgaacaagatggattgcacgcaggttctccggccgcttgggtggagaggctattcgg
ctatgactgggcacaacagacaatcggctgctctgatgccgccgtgttccggctgtcagc
gcaggggcgcccggttcttttgtcaagaccgacctgtccggtgccctgaatgaactgca
ggacgaggcagcgcggctatcgtggctggccacgacgggcgttccttgcgcagctgtgct
cgacgttgtcactgaagcgggaagggactggctgctattgggcgaagtgccggggcagga
tctcctgtcatctcaccttgctcctgccgagaaagtatccatcatggctgatgcaatgcg
gcggctgcatacgcttgatccggctacctgcccattcgaccaccaagcgaaacatcgcat
cgagcgagcacgtactcggatggaagccggtcttgtcgatcaggatgatctggacgaaga
gcatcaggggctcgcgccagccgaactgttcgccaggctcaaggcgcgcatgcccgacgg
cgaggatctcgtcgtgacccatggcgatgcctgattgccgaatatcatggtggaaaatgg
ccgcttttctggattcatcgactgtggccggctgggtgtggcggaccgctatcaggacat
agcgttggctacccgtgatattgctgaagagcttggcggcgaatgggctgaccgcttcct
```

-continued

```
cgtgctttacggtatcgccgctcccgattcgcagcgcatcgccttctatcgccttcttga cgagttcttctgagcgggactctggggttcgaaatgaccgaccaagcgacgcccaacctg ccatcacgagatttcgattccaccgccgccttctatgaaaggttgggcttcggaatcgtt ttccgggacgccggctggatgatcctccagcgcggggatctcatgctggagttcttcgcc cacccccaacttgtttattgcagcttataatggttacaaataaagcaatagcatcacaaat ttcacaaataaagcattttttttcactgcattctagttgtggtttgtccaaactcatcaat gtatcttatcatgtctgtataccgtcgacctctagctagagcttggcgtaatcatggtca tagctgtttcctgtgtgaaattgttatccgctcacaattccacacaacatacgagccgga agcataaagtgtaaagcctggggtgcctaatgagtgagctaactcacattaattgcgttg cgctcactgcccgctttccagtcgggaaacctgtcgtgccagctgcattaatgaatcggc caacgcgcgggagaggcggtttgcgtattgggcgctcttccgcttcctcgctcactgac tcgctgcgctcggtcgttcggctgcggcgagcggtatcagctcactcaaaggcggtaata cggttatccacagaatcaggggataacgcaggaaagaacatgtgagcaaaaggccagcaa aaggccaggaaccgtaaaaaggccgcgttgctggcgtttttccataggctccgcccccct gacgagcatcacaaaaatcgacgctcaagtcagaggtggcgaaacccgacaggactataa agataccaggcgtttccccctggaagctccctcgtgcgctctcctgttccgaccctgccg cttaccggatacctgtccgcctttctcccttcgggaagcgtggcgctttctcatagctca cgctgtaggtatctcagttcggtgtaggtcgttcgctccaagctgggctgtgtgcacgaa ccccccgttcagcccgaccgctgcgccttatccggtaactatcgtcttgagtccaacccg gtaagacacgacttatcgccactggcagcagccactggtaacaggattagcagagcgagg tatgtaggcggtgctacagagttcttgaagtggtggcctaactacggctacactagaaga acagtatttggtatctgcgctctgctgaagccagttaccttcggaaaaagagttggtagc tcttgatccggcaaacaaaccaccgctggtagcggttttttttgtttgcaagcagcagatt acgcgcagaaaaaaaggatctcaagaagatcctttgatcttttctacggggtctgacgct cagtggaacgaaaactcacgttaagggattttggtcatgagattatcaaaaaggatcttc acctagatccttttaaattaaaaatgaagttttaaatcaatctaaagtatatatgagtaa acttggtctgacagttaccaatgcttaatcagtgaggcacctatctcagcgatctgtcta tttcgttcatccatagttgcctgactccccgtcgtgtagataactacgatacgggagggc ttaccatctggccccagtgctgcaatgataccgcgagacccacgctcaccggctccagat ttatcagcaataaaccagccagccggaagggccgagcgcagaagtggtcctgcaacttta tccgcctccatccagtctattaattgttgccgggaagctagagtaagtagttcgccagtt aatagtttgcgcaacgttgttgccattgctacaggcatcgtggtgtcacgctcgtcgttt ggtatggcttcattcagctccggttcccaacgatcaaggcgagttacatgatcccccatg ttgtgcaaaaaagcggttagctccttcggtcctccgatcgttgtcagaagtaagttggcc gcagtgttatcactcatggttatggcagcactgcataattctcttactgtcatgccatcc gtaagatgcttttctgtgactggtgagtactcaaccaagtcattctgagaatagtgtatg cggcgaccgagttgctcttgcccggcgtcaatacgggataataccgcgccacatagcaga actttaaaagtgctcatcattggaaaacgttcttcggggcgaaaactctcaaggatctta ccgctgttgagatccagttcgatgtaacccactcgtgcacccaactgatcttcagcatct tttactttcaccagcgtttctgggtgagcaaaaacaggaaggcaaaatgccgcaaaaaag ggaataagggcgacacggaaatgttgaatactcatactcttcctttttcaatattattga
```

-continued agcatttatcagggttattgtctcatgagcggatacatatttgaatgtatttagaaaaat aaacaaatagggttccgcgcacatttccccgaaaagtgccacctgacgtc

5

Plasmid pcDNA3.1(+) hMCP1 hIgG1 monomeric variant (the initiation and the stop codons in underscored text, the codons for the linker of MCP-1 and mIg in bold text):

(SEQ ID NO: 28)

gacggatcgggagatctcccgatcccctatggtgcactctcagtacaatctgctctgatg ccgcatagttaagccagtatctgctccctgcttgtgtgttggaggtcgctgagtagtgcg cgagcaaaatttaagctacaacaaggcaaggcttgaccgacaattgcatgaagaatctgc ttagggttaggcgttttgcgctgcttcgcgatgtacgggccagatatacgcgttgacatt gattattgactagttattaatagtaatcaattacggggtcattagttcatagcccatata tggagttccgcgttacataacttacggtaaatggcccgcctggctgaccgcccaacgacc cccgcccattgacgtcaataatgacgtatgttcccatagtaacgccaatagggactttcc attgacgtcaatgggtggagtatttacggtaaactgcccacttggcagtacatcaagtgt atcatatgccaagtacgccccctattgacgtcaatgacggtaaatggcccgcctggcatt atgcccagtacatgaccttatgggactttcctacttggcagtacatctacgtattagtca tcgctattaccatggtgatgcggttttggcagtacatcaatgggcgtggatagcggtttg actcacggggatttccaagtctccaccccattgacgtcaatgggagtttgttttggcacc aaaatcaacgggactttccaaaatgtcgtaacaactccgccccattgacgcaaatgggcg gtaggcgtgtacggtgggaggtctatataagcagagctctctggctaactagagaaccca ctgcttactggcttatcgaaattaatacgactcactatagggagacccaagctggctagc gtttaaacttaagattacgatcagtcgaattcgccgccacc<u>atg</u>aaagtctctgccgccc ttctgtgcctgctgctcatagcagccaccttcattccccaagggctcgctcagccagatg caatcaatgccccagtcacctgctgttataacttcaccaataggaagatctcagtgcaga ggctcgcgagctatagaagaatcaccagcagcaagtgtcccaaagaagctgtgatcttca agaccattgtggccaaggagatctgtgctgaccccaagcagaagtgggttcaggattcca tggaccacctggacaagcaaacccaaactccgaagactggatccgttgagcccaaatctt ctgacaaaactcacacatctccaccgtctccagcacctgaactcctggggggaccgtcag tcttcctcttccccccaaaacccaaggacaccctcatgatctcccggacccctgaggtca catgcgtggtggtggacgtgagccacgaagaccctgaggtcaagttcaactggtacgtgg acggcgtggaggtgcataatgccaagacaaagccgcgggaggagcagtacaacagcacgt accgtgtggtcagcgtcctcaccgtcctgcaccaggactggctgaatggcaaggagtaca agtgcaaggtctccaacaaagccctcccagcccccatcgagaaaaccatctccaaagcca aagggcagccccgagaaccacaggtgtacaccctgcccccatcccgggatgagctgacca agaaccaggtcagcctgacctgcctggtcaaaggcttctatcccagcgacatcgccgtgg agtgggagagcaatgggcagccggagaacaactacaagaccacgcctcccgtgctggact ccgacggctccttcttcctctacagcaagctcaccgtggacaagagcaggtggcagcagg ggaacgtcttctcatgctccgtgatgcatgaggctctgcacaaccactacacgcagaaga gcctctccctgtctccgggtaaa<u>tga</u>ctagtcatagtttagcggccgctcgagtctagag ggcccgtttaaacccgctgatcagcctcgactgtgccttctagttgccagccatctgttg tttgcccctcccccgtgccttccttgaccctggaaggtgccactcccactgtcctttcct -continued

```
aataaaatgaggaaattgcatcgcattgtctgagtaggtgtcattctattctgggggtg
gggtggggcaggacagcaaggggggaggattgggaagacaatagcaggcatgctggggatg
cggtgggctctatggcttctgaggcggaaagaaccagctggggctctaggggtatcccc
acgcgccctgtagcggcgcattaagcgcggcgggtgtggtggttacgcgcagcgtgaccg
ctacacttgccagcgccctagcgcccgctcctttcgctttcttccttcctttctcgcca
cgttcgccggctttccccgtcaagctctaaatcgggggctccctttaggggttccgattta
gtgctttacggcacctcgaccccaaaaaacttgattagggtgatggttcacgtagtgggc
catcgccctgatagacggttttttcgccctttgacgttggagtccacgttctttaatagtg
gactcttgttccaaactggaacaacactcaaccctatctcggtctattcttttgatttat
aagggattttgccgatttcggcctattggttaaaaaatgagctgatttaacaaaaattta
acgcgaattaattctgtggaatgtgtgtcagttagggtgtggaaagtccccaggctcccc
agcaggcagaagtatgcaaagcatgcatctcaattagtcagcaaccaggtgtggaaagtc
cccaggctcccagcaggcagaagtatgcaaagcatgcatctcaattagtcagcaaccat
agtcccgcccctaactccgcccatcccgcccctaactccgcccagttccgcccattctcc
gccccatggctgactaattttttttatttatgcagaggccgaggccgcctctgcctctga
gctattccagaagtagtgaggaggcttttttggaggcctaggcttttgcaaaaagctccc
gggagcttgtatatccattttcggatctgatcaagagacaggatgaggatcgtttcgcat
gattgaacaagatggattgcacgcaggttctccggccgcttgggtggagaggctattcgg
ctatgactgggcacaacagacaatcggctgctctgatgccgccgtgttccggctgtcagc
gcaggggcgcccggttcttttttgtcaagaccgacctgtccggtgccctgaatgaactgca
ggacgaggcagcgcggctatcgtggctggccacgacgggcgttccttgcgcagctgtgct
cgacgttgtcactgaagcgggaagggactggctgctattgggcgaagtgccggggcagga
tctcctgtcatctcaccttgctcctgccgagaaagtatccatcatggctgatgcaatgcg
gcggctgcatacgcttgatccggctacctgcccattcgaccaccaagcgaaacatcgcat
cgagcgagcacgtactcggatggaagccggtcttgtcgatcaggatgatctggacgaaga
gcatcaggggctcgcgccagccgaactgttcgccaggctcaaggcgcgcatgcccgacgg
cgaggatctcgtcgtgacccatggcgatgcctgcttgccgaatatcatggtggaaaatgg
ccgcttttctggattcatcgactgtggccggctgggtgtggcggaccgctatcaggacat
agcgttggctacccgtgatattgctgaagagcttggcggcgaatgggctgaccgcttcct
cgtgctttacggtatcgccgctcccgattcgcagcgcatcgccttctatcgccttcttga
cgagttcttctgagcgggactctggggttcgaaatgaccgaccaagcgacgcccaacctg
ccatcacgagatttcgattccaccgccgccttctatgaaaggttgggcttcggaatcgtt
ttccgggacgccggctggatgatcctccagcgcggggatctcatgctggagttcttcgcc
cacccaacttgtttattgcagcttataatggttacaaataaagcaatagcatcacaaat
ttcacaaataaagcattttttcactgcattctagttgtggtttgtccaaactcatcaat
gtatcttatcatgtctgtataccgtcgacctctagctagagcttggcgtaatcatggtca
tagctgtttcctgtgtgaaattgttatccgctcacaattccacacaacatacgagccgga
agcataaagtgtaaagcctggggtgcctaatgagtgagctaactcacattaattgcgttg
cgctcactgcccgctttccagtcgggaaacctgtcgtgccagctgcattaatgaatcggc
caacgcgcgggagaggcggtttgcgtattgggcgctcttccgcttcctcgctcactgac
tcgctgcgctcggtcgttcggctgcggcgagcggtatcagctcactcaaaggcggtaata
```

-continued
```
cggttatccacagaatcaggggataacgcaggaaagaacatgtgagcaaaaggccagcaa aaggccaggaaccgtaaaaaggccgcgttgctggcgttttttccataggctccgcccccct gacgagcatcacaaaaatcgacgctcaagtcagaggtggcgaaacccgacaggactataa agataccaggcgtttccccctggaagctccctcgtgcgctctcctgttccgaccctgccg cttaccggatacctgtccgcctttctccttcgggaagcgtggcgctttctcatagctca cgctgtaggtatctcagttcggtgtaggtcgttcgctccaagctgggctgtgtgcacgaa cccccgttcagcccgaccgctgcgccttatccggtaactatcgtcttgagtccaacccg gtaagacacgacttatcgccactggcagcagccactggtaacaggattagcagagcgagg tatgtaggcggtgctacagagttcttgaagtggtggcctaactacggctacactagaaga acagtatttggtatctgcgctctgctgaagccagttaccttcggaaaaagagttggtagc tcttgatccggcaaacaaaccaccgctggtagcggttttttttgtttgcaagcagcagatt acgcgcagaaaaaaggatctcaagaagatcctttgatcttttctacggggtctgacgct cagtggaacgaaaactcacgttaagggattttggtcatgagattatcaaaaaggatcttc acctagatccttttaaattaaaaatgaagttttaaatcaatctaaagtatatatgagtaa acttggtctgacagttaccaatgcttaatcagtgaggcacctatctcagcgatctgtcta tttcgttcatccatagttgcctgactccccgtcgtgtagataactacgatacgggagggc ttaccatctggccccagtgctgcaatgataccgcgagacccacgctcaccggctccagat ttatcagcaataaaccagccagccggaagggccgagcgcagaagtggtcctgcaacttta tccgcctccatccagtctattaattgttgccgggaagctagagtaagtagttcgccagtt aatagtttgcgcaacgttgttgccattgctacaggcatcgtggtgtcacgctcgtcgttt ggtatggcttcattcagctccggttcccaacgatcaaggcgagttacatgatcccccatg ttgtgcaaaaaagcggttagctccttcggtcctccgatcgttgtcagaagtaagttggcc gcagtgttatcactcatggttatggcagcactgcataattctcttactgtcatgccatcc gtaagatgcttttctgtgactggtgagtactcaaccaagtcattctgagaatagtgtatg cggcgaccgagttgctcttgcccggcgtcaatacgggataataccgcgccacatagcaga actttaaaagtgctcatcattggaaaacgttcttcggggcgaaaactctcaaggatctta ccgctgttgagatccagttcgatgtaacccactcgtgcacccaactgatcttcagcatct tttactttcaccagcgtttctgggtgagcaaaaacaggaaggcaaaatgccgcaaaaaag ggaataagggcgacacggaaatgttgaatactcatactcttccttttttcaatattattga agcatttatcagggttattgtctcatgagcggatacatatttgaatgtatttagaaaaat aaacaaataggggttccgcgcacatttccccgaaaagtgccacctgacgtc
```

Therapeutic Compositions and Methods

The present invention includes methods for treating or preventing any medical condition or disorder or disease that is treatable by decreasing the migration of chemokine receptor-bearing cells (e.g., CCR2-bearing cells; such as monocytes, macrophages, and memory T lymphocytes) into inflammatory tissues, by decreasing endogenous chemokine (e.g., MCP1) expression or associated activity (e.g., CCR2 receptor binding), or by decreasing the expression or activity of the chemokine receptor (e.g., CCR2). In an embodiment of the invention, inflammatory disorders are treated by desensitizing chemokine receptor (e.g., CCR2) bearing cells, in a subject, to the presence of the cognate chemokine ligand (e.g., MCP1) by systemic administration of the ligand to the subject. The chemokine ligand can be administered, in an embodiment of the invention, for a prolonged period of time so as to reach the fullest levels of desensitization in the cells. For example, the present invention includes a method for treating or preventing an inflammatory disorder in a subject by administering, to the subject, a therapeutically effective amount of a chemokine or multimer or fusion thereof, e.g., MCP1, an MCP1 multimer or a fusion thereof (e.g., fused to an in vivo half-life extending moiety (e.g., PEG or Ig)) or a pharmaceutical composition thereof (e.g., comprising a pharmaceutically acceptable carrier) optionally in association with a therapeutically effective amount of a further therapeutic agent.

A pharmaceutical composition of the invention may be prepared by any methods well known in the art of pharmacy;

see, e.g., Gilman, et al., (eds.) (1990), *The Pharmacological Bases of Therapeutics,* 8th Ed., Pergamon Press; A. Gennaro (ed.), *Remington's Pharmaceutical Sciences,* 18th Edition, (1990), Mack Publishing Co., Easton, Pa.; Avis, et al., (eds.) (1993) *Pharmaceutical Dosage Forms: Parenteral Medications* Dekker, New York; Lieberman, et al., (eds.) (1990) *Pharmaceutical Dosage Forms: Tablets* Dekker, New York; and Lieberman, et al., (eds.) (1990), *Pharmaceutical Dosage Forms: Disperse Systems* Dekker, New York.

The term "inflammatory disorder" or "medical inflammatory disorder" includes, in an embodiment of the invention, psoriasis (e.g., nail psoriasis, scalp psoriasis, plaque psoriasis, pustular psoriasis, guttate psoriasis, inverse psoriasis, erythrodermic or psoriatic arthritis), ankylosing spondylitis, appendicitis, peptic ulcer, gastric ulcer and duodenal ulcer, peritonitis, pancreatitis, inflammatory bowel disease, colitis, ulcerative colitis, pseudomembranous colitis, acute colitis, ischemic colitis, diverticulitis, epiglottitis, achalasia, cholangitis, cholecystitis, coeliac disease, hepatitis, Crohn's disease (e.g., ileocolitis, ileitis, gastroduodenal Crohn's disease, jejunoileitis or Crohn's (granulomatous) colitis), enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, and urethritis, bronchitis, emphysema, rhinitis, cystic fibrosis, pneumonitis, adult respiratory distress syndrome, pneumoultramicroscopicsilicovolcanoconiosis, alvealitis, bronchiolitis, pharyngitis, pleurisy, sinusitis, dermatitis, atopic dermatitis, dermatomyositis, sunburn, urticaria warts, wheals, stenosis, restenosis, vasulitis, angiitis, endocarditis, arteritis, atherosclerosis, thrombophlebitis, pericarditis, myocarditis, myocardial ischemia, periarteritis nodosa, rheumatic fever, meningitis, encephalitis, multiple sclerosis, neuritis, neuralgia, uveitis (e.g., anterior, posterior, intermediate or diffuse), arthritides and arthralgias, osteomyelitis, fasciitis, Paget's disease, gout, periodontal disease, rheumatoid arthritis (e.g., polyarticular-course juvenile rheumatoid arthritis or psoriatic arthritis), synovitis, myasthenia gravis, thryoiditis, systemic lupus erythematosus, Goodpasture's syndrome, Behcets's syndrome, allograft rejection or graft-versus-host disease.

The present invention also includes a method for treating or preventing a parasitic, viral or bacterial infection in a subject by administering, to the subject, a therapeutically effective amount of chemokine, multimer or fusion thereof, for example, MCP1, an MCP1 multimer or a fusion thereof (e.g., fused to an in vivo half-life extending moiety (e.g., PEG or Ig)) or a pharmaceutical composition thereof (e.g., comprising a pharmaceutically acceptable carrier) optionally in association with a therapeutically effective amount of a further therapeutic agent. In an embodiment of the invention, the infection is herpes simplex virus infection (e.g., HSV1 or HSV2), human T lymphotropic virus (HTLV; e.g., type I) infection, HIV infection, HIV neuropathy, meningitis, hepatitis (A, B or C, or the like), septic arthritis, peritonitis, pneumonia, epiglottitis, *E. coli* 0157:h7, hemolytic uremic syndrome, thrombolytic thrombocytopenic purpura, malaria, dengue hemorrhagic fever, leishmaniasis, leprosy, toxic shock syndrome, streptococcal myositis, gas gangrene, mycobacterium tuberculosis, mycobacterium avium intracellulare, pneumocystis carinii pneumonia, pelvic inflammatory disease, orchitis, epidydimitis, legionella, lyme disease, influenza a, epstein-barr virus, vital-associated hemaphagocytic syndrome, vital encephalitis or aseptic meningitis.

The present invention also includes a method for treating or preventing a cancer or malignancy (e.g., breast, ovarian, stomach, endometrial, salivary gland, lung, kidney, colon, colorectal, thyroid, pancreatic, prostate or bladder cancer) in a subject by administering, to the subject, a therapeutically effective amount of chemokine, multimer or fusion thereof, for example, MCP1, an MCP1 multimer or a fusion thereof (e.g., fused to an in vivo half-life extending moiety (e.g., PEG or Ig)) or a pharmaceutical composition thereof (e.g., comprising a pharmaceutically acceptable carrier) optionally in association with a therapeutically effective amount of a further therapeutic agent.

The present invention also includes a method for treating or preventing a cardiovascular or circulatory disorder in a subject by administering, to the subject, a therapeutically effective amount of chemokine, multimer or fusion thereof, for example, MCP1, an MCP1 multimer or a fusion thereof (e.g., fused to an in vivo half-life extending moiety (e.g., PEG or Ig)) or a pharmaceutical composition thereof (e.g., comprising a pharmaceutically acceptable carrier) optionally in association with a therapeutically effective amount of a further therapeutic agent. In an embodiment of the invention, the disease or disorder is cardiac stun syndrome, myocardial infarction, congestive heart failure, stroke, ischemic stroke, hemorrhage, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneurysms, aortic dissection, inflammation of the aorta, occlusion of the abdominal aorta and its branches, peripheral vascular disorders, occlusive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome or ischemia-reperfusion injury.

A pharmaceutical composition containing chemokine, multimer or fusion thereof, for example, MCP1 or a multimer or fusion thereof (e.g., MCP1-Ig) can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like. All routes of administration are contemplated including, but not limited to, parenteral (e.g., subcutaneous, intravenous, intraperitoneal, intratumoral or intramuscular) and non-parenteral (e.g., oral, transdermal, intranasal, intraocular, sublingual, inhalation, rectal and topical).

Injectables can be prepared in conventional forms, either as liquid solutions or suspensions, solid forms suitable for solution or suspension in liquid prior to injection, or as emulsions. The injectables, solutions and emulsions can also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations are generally added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN-80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

Preparations for parenteral administration can include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

Implantation of a slow-release or sustained-release system, such that a constant level of dosage is maintained is also contemplated herein. Briefly, in this embodiment, chemokine, multimer or fusion thereof, for example, MCP1 or a fusion or multimer thereof (e.g., MCP1-Ig) is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient diffuses through the outer polymeric membrane in a release rate controlling step. The percentage of active compound contained in such parenteral compositions is highly dependent on the specific nature thereof, as well as the activity of the chemokine, multimer or fusion thereof, for example, MCP1 or fusion or multimer thereof and the needs of the subject.

The concentration of the chemokine, multimer or fusion thereof, for example, MCP1 or fusion or multimer thereof can be adjusted so that an injection provides an effective amount to produce the desired pharmacological effect. The exact dose depends, inter alia, on the age, weight and condition of the patient or animal as is known in the art.

A unit-dose parenteral preparation comprising chemokine, multimer or fusion thereof, for example, MCP1 or fusion or multimer thereof is packaged in an ampoule, a vial or a syringe with a needle. All preparations for parenteral administration must be sterile, as is known and practiced in the art. Such a preparation forms part of the present invention.

A chemokine, multimer or fusion thereof, for example, MCP1 or a fusion or multimer thereof can be formulated into a lyophilized powder, which can be reconstituted for administration as solutions, emulsions and other mixtures. The powder may also be reconstituted and formulated as a solid or gel.

The sterile, lyophilized powder is prepared by dissolving chemokine, multimer or fusion thereof, for example, MCP1 or a fusion or multimer thereof, or a pharmaceutically acceptable derivative thereof, in a suitable solvent. The solvent may contain an excipient which improves the stability or another pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial can contain a single dosage or multiple dosages of the chemokine, multimer or fusion thereof, for example, the MCP1 or fusion or multimer thereof. The lyophilized powder can be stored under appropriate conditions, such as at about 4° C. to room temperature.

Reconstitution of this lyophilized powder with water for injection provides a formulation for use in parenteral administration. For reconstitution, the lyophilized powder can be added to sterile water or another suitable carrier. The precise amount depends upon the selected compound. Such an amount can be empirically determined.

Administration by inhalation can be provided by using, e.g., an aerosol containing sorbitan trioleate or oleic acid, for example, together with trichlorofluoromethane, dichlorofluoromethane, dichlorotetrafluoroethane or any other biologically compatible propellant gas; it is also possible to use a system containing chemokine, multimer or fusion thereof, for example, MCP1 or fusion or multimer thereof, by itself or associated with an excipient, in powder form.

In an embodiment, chemokine, multimer or fusion thereof, for example, MCP1 or a fusion or multimer thereof is formulated into a solid dosage form for oral administration, in one embodiment, into a capsule or tablet. Tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The scope of the present invention includes methods comprising administration of chemokine, multimer or fusion thereof, for example, MCP1 or a fusion or multimer thereof, or a pharmaceutical composition thereof, in association with, for example, one or more further therapeutic agents as well as compositions comprising chemokine, multimer or fusion thereof, for example, MCP1 or a fusion or multimer thereof in association with a further therapeutic agent. In an embodiment, the other therapeutic agent is an agent that, when administered to a subject, treats or prevents an inflammatory condition in the subject. The administration and dosage of any such agent is typically as according to the schedule listed in the product information sheet of the approved agents, in the *Physicians' Desk Reference* 2003 (*Physicians' Desk Reference*, 57th Ed); Medical Economics Company; ISBN: 1563634457; 57th edition (November 2002), as well as therapeutic protocols well known in the art.

The term "in association with" indicates that the chemokine, multimer or fusion thereof, for example, the MCP1 or a fusion or multimer thereof and the further therapeutic agent can be formulated into a single composition for simultaneous delivery or formulated separately into two or more compositions (e.g., a kit). Furthermore, each component can be administered to a subject at a different time than when the other component is administered; for example, each administration may be given non-simultaneously (e.g., separately or sequentially) at several intervals over a given period of time. Moreover, the separate components may be administered to a subject by the same or by a different route (e.g., orally, intravenously, subcutaneously).

A "further therapeutic agent" is any agent, other than the chemokine, multimer or fusion thereof, that, when administered to a subject, brings about a desired or beneficial therapeutic effect, such as prevention, elimination or reduction of the progression or severity of symptoms associated with a given medical condition (e.g., an inflammatory disorder). A further therapeutic agent may be, for example, an anti-inflammatory agent or a pain reliever.

Further therapeutic agents that may be administered or combined in association with the chemokine, multimer or fusion thereof, for example, MCP1 or a fusion or multimer thereof include one or more non-steroidal anti-inflammatory drug (NSAIDs) such as aspirin, diclofenac, diflunisal, etodolac, fenoprofen, floctafenine, flurbiprofen, ibuprofen, indomethacin, ketoprofen, ketorolac, meclofenamate, mefenamic acid, meloxicam, nabumetone, naproxen, oxaprozin, phenylbutazone, piroxicam, salsalate, sulindac, tenoxicam, tiaprofenic acid or tolmetin.

Further therapeutic agents that may be administered or combined in association with the chemokine, multimer or fusion thereof, for example, MCP1 or a fusion or multimer thereof include one or more topical medications, for example, anthralin, calcipotriene, salicylic acid, coal tar, tazarotene, topical steroids (e.g., Clobetasol propionate; Clobetasol propionate; Betamethasone dipropionate; Clobetasol propionate; Diflorasone diacetate; Clobetasol propionate Halobetasol propionate; Amcinonide; Betamethasone dipropionate; Betamethasone dipropionate; Mometasone furoate; Diflorasone diacetate; Halcinonide; Fluocinonide; Diflorasone diacetate; Betamethasone dipropionate; Diflorasone diacetate; Desoximetasone; Desoximetasone; Triamcinolone acetonide; Fluticasone propionate; Amcinonide; Betamethasone dipropionate; Diflorasone diacetate; Fluocinonide; Betamethasone valerate; Diflorasone diacetate; Betamethasone dipropionate; Desoximetasone; Betamethasone valerate; Triamcinolone acetonide; Flurandrenolide; Fluocinolone acetonide; Mometasone furoate; Triamcinolone acetonide; Fluocinolone acetonide; Betamethasone benzoate; Hydrocortisone valerate; Flurandrenolide; Fluticasone propionate; Prednicarbate; Desonide; Betamethasone dipropionate; Triamcinolone acetonide; Hydrocortisone; Fluocinolone acetonide; Betamethasone benzoate; Betamethasone valerate; Hydrocortisone valerate; Alclometasone dipropionate; Desonide; Fluocinolone acetonide; Desonide; Betamethasone valerate; or a mixture of hydrocortisone, dexamethasone, methylprednisolone and prednisolone), petroleum jelly, aloe vera, oilated oatmeal, epsom salts or Dead Sea salts.

Further therapeutic agents that may be administered or combined in association with the chemokine, multimer or fusion thereof, for example, MCP1 or a fusion or multimer thereof include one or more of alefacept, etanercept, cyclosporine, methotrexate, acitretin, isotretinoin, hydroxyurea, mycophenolate mofetil, sulfasalazine or 6-Thioguanine.

Further therapeutic agents that may be administered or combined in association with the chemokine, multimer or fusion thereof, for example, MCP1 or a fusion or multimer thereof include one or more of anakinra, injectable gold, penicillamine, azathioprine, chloroquine, hydroxychloroquine, sulfasalazine or oral gold (e.g., auranofin, gold sodium thiomalate or aurothioglucose).

Further therapeutic agents that may be administered or combined in association with the chemokine, multimer or fusion thereof, for example, MCP1 or a fusion or multimer thereof include one or more of mesalamine, sulfasalazine, budesonide, metronidazole, ciprofloxacin, azathioprine, 6-mercaptopurine or dietary supplementation of calcium, folate or vitamin B12.

Further therapeutic agents that may be administered or combined in association with the chemokine, multimer or fusion thereof, for example, MCP1 or a fusion or multimer thereof include one or more COX2 inhibitors such as celecoxib (Celebrex®), rofecoxib (Vioxx®), valdecoxib (Bextra®), lumiracoxib (Prexige™) or etoricoxib (Arcoxia®).

Further therapeutic agents that may be administered or combined in association with the chemokine, multimer or fusion thereof, for example, MCP1 or a fusion or multimer thereof include one or more antibodies such as efalizumab (Raptiva®), adalimumab (Humira®), infliximab (Remicade®) or ABX-IL8.

In an embodiment of the invention, the chemokine, multimer or fusion thereof, for example, MCP1 or a fusion or multimer thereof is administered, to a subject, in association with phototherapy, particularly, wherein the subject suffers from psoriasis. In such an embodiment, the subject is exposed to sunlight, UVB light, PUVA (psoralen plus ultraviolet A). PUVA (psoralin-UVA) or laser light. PUVA uses ultraviolet A light to treat psoriasis in combination with psoralen, an oral or topical medication that makes your skin more sensitive to light. Lasers emit highly focused beams of light that affects primarily the psoriatic skin while healthy skin isn't exposed significantly. One type of laser, the XTRAC excimer laser, uses highly focused ultraviolet B light. Another type of laser used for psoriasis is a pulsed dye laser, which uses pulses of yellow light—different from the ultraviolet rays used in UVB or XTRAC—to destroy some of the blood cells that grow in patches of psoriasis. Treatment with pulsed dye lasers usually takes a few months, with appointments every three weeks.

Dosage and Administration

Typical protocols for the therapeutic administration of a composition of the invention are well known in the art. Pharmaceutical compositions of the invention may be administered, for example, by any parenteral (e.g., subcutaneous injection, intramuscular injection, intravenous injection) or non-parenteral route (e.g., orally, nasally).

Pills and capsules of the invention can be administered orally. Injectable compositions can be administered with medical devices known in the art; for example, by injection with a hypodermic needle.

Injectable pharmaceutical compositions of the invention may also be administered with a needleless hypodermic injection device; such as the devices disclosed in U.S. Pat. Nos. 5,399,163; 5,383,851; 5,312,335; 5,064,413; 4,941,880; 4,790,824 or 4,596,556.

In an embodiment, the daily dose of a "further therapeutic agent" (e.g., an anti-inflammatory agent) administered in association with the chemokine, multimer or fusion thereof, for example, MCP1 or a fusion or multimer thereof is, where possible, administered accordance with the *Physicians' Desk Reference* 2003 (*Physicians' Desk Reference*, 57th Ed); Medical Economics Company; ISBN: 1563634457; 57th edition (November 2002). The proper dosage can, however, be altered by a clinician to compensate for particular characteristics of the subject receiving the therapy depending, for example, on the potency of the compound administered or of the chemokine, multimer or fusion thereof (e.g., MCP1-Ig), side-effects, age, weight, medical condition, overall health and response.

The present invention provides methods for treating or preventing an inflammatory condition in a subject by administering, to the subject, a therapeutically effective amount of chemokine, multimer or fusion thereof, for example, MCP1 or a fusion or multimer thereof, optionally in association with a therapeutically effective amount of a further therapeutic agent. The term "therapeutically effective amount" means that amount of a therapeutic agent or substance (e.g., MCP1-Ig) that will elicit a biological or medical response of a tissue, system, subject or host that is being sought by the administrator (such as a researcher, doctor or veterinarian) which includes, for example, alleviation, reversal, elimination or halting or slowing of progression of a target medical disorder or any symptom thereof to any degree including prevention of the disorder in the subject. In an embodiment of the invention, a therapeutically effective amount or dosage of chemokine, multimer or fusion thereof, for example, MCP1 or a fusion or multimer thereof (e.g., MCP1-Ig; for example a polypeptide comprising any amino acid sequence as set forth in SEQ ID NO: 8, 9, 10, 11 or 12) is from about 0.1 mpk (mg per kilogram of body weight) to about 10 mpk (e.g., 0.25, 0.5, 0.75 1, 2, 3, 4, 5, 6, 7, 8, 9, 10 mpk) once a day, every 2 days, every 4 days or every 5 days or once a week.

A composition of the invention can be administered, for example, three times a day, twice a day, once a day, three times weekly, twice weekly or once weekly, once every two weeks or 3, 4, 5, 6, 7 or 8 weeks. Moreover, the composition can be administered over a short or long period of time (e.g., 1 week, 1 month, 1 year, 5 years)

Dosage regimens can be adjusted to provide the optimum desired response (e.g., a therapeutic response). For example, the dose can be reduced or increased as indicated by exigencies of the therapeutic situation. For example, dosage can be adjusted, by a practitioner of ordinary skill in the art (e.g., physician or veterinarian) according to the drug's efficacy, progression or persistence of the disease or any of its symptoms or the patient's age, weight, height, past medical history, present medications and the potential for cross-reaction, allergies, sensitivities and adverse side-effects.

A physician or veterinarian having ordinary skill in the art can readily determine and prescribe the effective amount of the pharmaceutical composition required. For example, the physician or veterinarian could start doses of chemokine, multimer or fusion thereof, for example, MCP1 or a fusion or multimer thereof or a pharmaceutical composition thereof at levels lower than that required in order to achieve the desired therapeutic effect and gradually increase the dosage until the desired effect is achieved.

For example, psoriasis progress can be monitored, by the physician or veterinarian by a variety of methods, and the dosing regimen can be altered accordingly. Methods by which to monitor psoriasis include, for example, by skin biopsy, or scraping and culture of skin patches, monitoring the spread of the condition on the skin of the subject or by an X-ray to check for psoriatic arthritis if joint pain is present and persistent.

For example, rheumatoid arthritis progress can be monitored, by the physician or veterinarian, by a variety of methods, and the dosing regimen can be altered accordingly. Methods by which to monitor rheumatoid arthritis include, for example, joint X-rays, a rheumatoid factor blood test, checking for elevated erythrocyte sedimentation rate (ESR), a complete blood count to check for low hematocrit (anemia) or abnormal platelet counts, a blood test to check for C-reactive protein or synovial fluid analysis.

For example, Crohn's disease progress can be monitored, by the physician or veterinarian, by a variety of methods, and the dosing regimen can be altered accordingly. Methods by which to monitor Crohn's disease include, for example, monitoring the severity of symptoms reported by the subject or patient, sigmoidoscopy, colonoscopy, ERCP (endoscopic retrograde cholangiopancreatography), endoscopic ultrasound, capsule endoscopy, Plain X-rays, X-rays with Contrast, CT Scan or white blood cell scan.

For example, uveitis progress can be monitored, by the physician or veterinarian, by a variety of methods, and the dosing regimen can be altered accordingly. Methods by which to monitor uveitis include, for example, examination of the eye with a slit lamp microscope and ophthalmoscopy, measuring visual acuity and intraocular pressure.

For example, ulcerative colitis progress can be monitored, by the physician or veterinarian, by a variety of methods, and the dosing regimen can be altered accordingly. Methods by which to monitor ulcerative colitis include, for example, routine check-ups, colonoscopies, rectal or colon biopsy, stool testing for blood or pus, blood tests to examine white blood cell levels or X-ray examination.

EXAMPLES

The following examples are provided to more clearly describe the present invention and should not be construed to limit the scope of the invention. Any method or composition disclosed in the Examples section constitute part of the present invention.

Example 1

Design, Construction, Expression and Purification of Human MCP1-Mouse Ig Heavy Chain γ1 (hinge-CH2-CH3) Fusion Design of Constructs.

hMCP1-mIg ($NH_2$-human MCP1-Mouse Ig Heavy chain γ1 (hinge-CH2-CH3)-COOH): A BamH1 site was introduced as a linker in the cDNA, resulting in an insertion of a dipeptide, Gly-Ser, at the junction of the MCP1 and the Ig H chain. The product was expected to form a dimer with predicted molecular mass of 68,993.

hMCP1-hIgG4 ($NH_2$-human MCP1-human Ig H chain γ4 (hinge-CH2-CH3)-COOH): A BamH1 site was introduced as a linker in the cDNA, resulting in an insertion of a dipeptide, Gly-Ser, at the junction of the MCP1 and the Ig H chain. The product was expected to form a dimer with predicted molecular mass of 69,146.

hMCP1-hIgG4 monomeric variant ($NH_2$-human MCP1-human Ig Heavy chain γ4 (hinge-CH2-CH3)-COOH): The two cysteine residues were replaced by serine residues to eliminate the intermolecular disulfide bonds. A BamH1 site was introduced as a linker in the cDNA, resulting in an insertion of a dipeptide, Gly-Ser, at the junction of the MCP1 and the Ig H chain. The product was expected to form a dimer with predicted molecular mass of 34,543.

hMCP1-hIgG1 ($NH_2$-human MCP1-human Ig H chain γ1 (hinge-CH2-CH3)-COOH): A BamH1 site was introduced as a linker in the cDNA, resulting in an insertion of a dipeptide, Gly-Ser, at the junction of the MCP1 and the Ig H chain. The product was expected to form a dimer with predicted molecular mass of 70,000.

hMCP1-hIgG1 monomeric variant ($NH_2$-human MCP1-human Ig Heavy chain γ1 (hinge-CH2-CH3)-COOH): The three cysteine residues were replaced by serine residues to eliminate the intermolecular disulfide bonds. A BamH1 site was introduced as a linker in the cDNA, resulting in an insertion of a dipeptide, Gly-Ser, at the junction of the MCP1 and the Ig H chain. The product was expected to form a dimer with predicted molecular mass of 34,955.

Expression and purification. In this example, MCP1-Ig was expressed in mammalian cells, secreted and then isolated from the cellular growth media. The isolated protein was analyzed by SDS-PAGE analysis.

The cDNA of human MCP1 (see Genbank accession No. NM_002982) and a partial cDNA derived from the constant region of mouse Ig (see Genbank accession No. BC057688) (including the coding sequences for the hinge, the CH2, and the CH3 regions) were cloned by reverse-transcription polymerase chain reaction (RT-PCR). The MCP1-Ig cDNA was cloned into mammalian expression vector pcDNA3.1 (+) (Invitrogen, Carlsbad, Calif.) as a Hind3-Not1 fragment by standard molecular biology procedures to create the pcDNA3.1 (+)hMCP1 mIgG plasmid.

CHO-K1 (ATCC CRL-9618) cells were maintained in D-MEM/F-12 medium (Invitrogen, Carlsbad, Calif.) supplemented with 5% fetal bovine serum). The plasmid DNA was introduced into CHO-K1 cells using the Lipofectamine 2000 transfection kit (Invitrogen, Carlsbad, Calif.) by following the protocol suggested by the manufacturer. At forty-eight hours post-transfection, G418 (Invitrogen) was added to the culture at 1 mg/ml for selection of stably transfected cells. The G418 resistant cells appeared as colonies in about 10-14 days post transfection. The cells were then pooled and transfected by limiting dilution into 96-well tissue culture plates at frequencies of 3 cells per well, 1 cells per well, and 0.3 cells per well. Single cell-derived clones appeared in about 7-10 days and the conditioned media were examined by enzyme-linked immunosorbent assay (ELISA) specific for mouse IgG1 (Bethyl, Montgomery, Tex.). Clones giving highest titers were re-examined for expression level by normalizing the yield to the cell numbers. A clone producing at greater than 40 mg per liter was chosen for production (clone 52).

Production of the hMCP1-mIg protein was carried out under serum-free conditions. Clone 52 cells were stepwisely weaned into suspension culture of protein-free medium consisting of IS-CHO V base medium (Irvine Scientific, Irvine, Calif.). Each liter of the protein-free medium contains 8 mM glutamine (Invitrogen, Gaithersburg, Md.), 10 ml of 100×HT (Invitrogen), 1 ml of CD-lipid (Invitrogen), 8 ml of 45% glucose (Sigma, St. Louis, Mo.), 20 ml of GSEM (Sigma), 1 ml each of Trace Element A and Trace Element B (Cellgro, Herndon, Va.). For production, cells were seeded at a density of $0.5×10^6$ per ml in a volume of 1 liter in a 3-liter shaker flask. The flask was shaken at a speed of 75 rpm at a constant temperature of 37° C. in the presence of 7.5% $CO_2$. The concentration of glutamine was maintained at about 300 milligrams per liter and the concentration of glucose was maintained at 1-2 gram per liter. Conditioned media were harvested at approximately 14 days when cell viability was about 20%. The conditioned media were filtered through a 2-micron filtration unit followed by processing through an Affi-gel protein-A affinity column (BioRad, Hercules, Calif.) according to the manufacturer's suggested protocol. The purified protein was analyzed by SDS-polyacrylamide gel electrophoresis (SDS-PAGE) under reducing conditions. A single band was observed after the gel was stained by SimplyBlue SafeStain (Invitrogen), with an estimated size of about 34 kilodaltons. The purity of the product was estimated greater than 99%.

Example 2

Cell Migration Assay

In this example, the presence of human MCP1-mIg was demonstrated to impede the ability of THP-1 human monocytic cells to migrate toward a recombinant human MCP1 gradient was demonstrated.

THP-1 cells (ATCC TIB202) were maintained in RPMI1640 supplemented with 10% fetal bovine serum, 1 mM sodium pyruvate, 4.5 g/liter glucose, 1.5 g/l sodium bicarbonate, 10 mM HEPES, 0.05 mM beta-mercaptoethanol, and penicillin/streptomycin. Cell migration assay was performed using 96-well ChemoTx microplates with a 5 µm filter (NeuroProbe, Gathersburg, Md.) according to the manufacturer's instructions. Recombinant human MCP1 (rhMCP1) (R & D Systems, Minneapolis, Minn.) was placed in the bottom chamber. hMCP1-mIg or isotype control IgG was placed in both the top and the bottom chambers. Cells were dispensed in the top wells. The microplates were placed in a 37° C. humidified $CO_2$ (5%) incubator for 2 hours to allow the cells to migrate toward human MCP1 in the bottom chamber. Cell migration was quantitated as relative luminescent units (RLU) by CellTiter-Glo Luminiscent Cell Viability Assay Kit (Promega, Madison, Wis.) according to the manufacturer's protocol. Cell migration was calculated by subtracting the RLU of spontaneous migration from the RLU of the migration in the presence of the chemokine reagents. The relative % of migration was calculated by using the highest number of cell migration as 100%.

The approximated EC50 values for hMCP1-mIg and rhMCP1 were about 0.5 nM and 0.05 nM, respectively (Table 1, left and middle columns). hMCP1-mIg at 3 nM caused a significant reduction of the ability of THP-1 cells to migrate toward a gradient of rhMCP1 (Table 1, right column).

TABLE 1

Effects of hMCP1-mIg and recombinant human MCP1 (rhMCP1) on the migration of THP-1 human monocytic cells.
Relative % of cell migration

| Conc. (nM) | hMCP1-mIg alone | rhMCP1 alone | rhMCP1 plus hMCP1-mIg at 3 nM |
|---|---|---|---|
| 0.01 | 8.3 | 41 | −3 |
| 0.03 | 14.2 | 49.2 | 5.8 |
| 0.1 | 29.8 | 59.4 | 8.7 |
| 0.3 | 30.0 | 72.0 | −0.2 |
| 1 | 59.0 | 90.5 | 7.6 |
| 3 | 81.2 | 100 | 34.1 |
| 10 | 73.0 | 58.6 | 35.5 |
| 30 | 96.6 | 24.8 | 3.5 |
| 100 | 75.5 | −18.3 | −10.7 |

Example 3

Collagen-Induced Arthritis Assay

Male B10.RIII mice, 12-13 weeks of age, were immunized with bovine type II collagen (BCII) (Elastin Products, Owensville, Mo.), Difco incomplete Freunds adjuvant and *Mycobacteria tuberculosis* (MBT, strain H37RA, Sigma, St. Louis, Mo.). BCII was dissolved overnight at 4° C. in 0.01 M acetic acid (60 mg BCII in 25 ml 0.01 M acetic acid). Complete Freunds adjuvant (CFA) was prepared by mixing *M. tuberculosis* with Difco incomplete Freunds adjuvant (1 mg/ml). One volume of BCII and one volume of CFA were then mixed to emulsify. The emulsion contained 1200 µg/ml BCII and 0.5 mg/ml *M. tuberculosis*.

Mice were immunized by intradermal injection at 5 sites on the back including 1 site at the base of the tail. Each mouse received a total volume of 0.25 ml of the emulsion, which is equivalent to 300 µg BCII/mouse.

Mice were scored for symptoms and severity of arthritis 16 days after the immunization and divided into groups of 15 for dosing such that each group has the same number of mice with arthritis. Scores were based on a scale of 0 to 4 as follows:

0=normal
1=redness
2=one or more digits swollen
3=entire paw swollen
4=ankylosis Scores were taken 4 days before the boost and on days 0, 2, 4, 7 & 9. Swelling was also evaluated on these days by caliper measurement.

The immunizations were also boosted: BCII was dissolved overnight in 0.01M acetic acid (12.5 mg BCII in 25 ml 0.01M acetic acid). Mice were boosted, ip, with 100 µg BCII/0.2 ml/mouse, 20 days after immunization (Day 0 based on the boost).

hMCP1-mIg (SEQ ID NO: 8) and mIgG1 (TC31-27F11, SP-BioPharma, Palo Alto, Calif.) were prepared in phosphor-buffered saline at 2 mg/ml and administered intraperitoneally to the mice at indicated time points. The first dose was given at 20 milligrams per kilogram body weight (mpk). The subsequent doses were given at 10 mpk.

Serum samples were taken at the termination for determination of anti-collagen antibody (IgG2a).

A protecting effect was observed in the group of hMCP1-mIg-treated mice as indicated by the mean disease scores of Table 2 as well as by the paw swelling values of Table 3.

Plasma levels of anti-collagen IgG2a were determined by ELISA. The plates were coated with ELISA grade Type II Bovine Collagen (Chondrex, Redmond, Wash.) at 50 µl per ml at 4° C. overnight. The plate was washed by PBS followed by blocking with 1% BSA at 4° C. overnight. After a brief wash, samples were diluted at 1:10,000 and applied to the plate along with the standards (US Biologicals, Swampscott, Mass.) of 2-fold serial dilutions starting at 40 pg per ml. The plate was incubated at 4° C. overnight. After wash 100 µl of Peroxidase-conjugated anti-IgG (Abcam, Cambridge, Mass.) (1:500 diluted) was added to the wells and incubated at room temperature for 2 hours. The plate was washed and 100 µl of TMB (Sigma) was added to the wells. The plate was read at 490 nM.

In hMCP1-mIg treated animals, the levels of anti-collagen IgG2a antibody were suppressed, as compared to the levels of the isotype control (mIgG1)-treated animals (Table 4).

TABLE 2

Arthritic score of collagen arthritis in mice (mean ± SEM).

| | Scores | | | | | |
|---|---|---|---|---|---|---|
| | Day −4 | Day 0 | Day 2 | Day 4 | Day 7 | Day 9 |
| Normal | 0 | 0 | 0 | 0 | 0 | 0 |
| Isotype ctrl (mIgG1) | 0 | 0.6 ± 0.3 | 2.4 ± 0.7 | 3.1 ± 0.7 | 5.2 ± 0.8 | 5.2 ± 0.8 |
| hMCP1-mIg | 0 | 0.1 ± 0.1 | 0.8 ± 0.3* | 1.1 ± 0.4* | 2.7 ± 0.5* | 3.5 ± 0.7 |

*p < 0.05.

TABLE 3

Paw swelling of collagen arthritis in mice (mean ± SEM).

| | Paw swelling (mm) | | | | | |
|---|---|---|---|---|---|---|
| Treatment | Day −4 | Day 0 | Day 2 | Day 4 | Day 7 | Day 9 |
| Normal | 1.80 ± 0.00 | 1.80 ± 0.00 | 1.80 ± 0.00 | 1.82 ± 0.01 | 1.83 ± 0.01 | 1.83 ± 0.02 |
| Isotype ctrl (mIgG1) | 1.80 ± 0.00 | 1.83 ± 0.03 | 1.88 ± 0.04 | 1.99 ± 0.05 | 2.15 ± 0.07 | 2.23 ± 0.08 |
| hMCP1-mIg | 1.80 ± 0.00 | 1.81 ± 0.00 | 1.80 ± 0.00* | 1.82 ± 0.01* | 1.89 ± 0.04* | 2.03 ± 0.06* |

*p < 0.05 of the paw sizes of the hMCP1-mIg-treated comparing to those of the isotype control group.

TABLE 4

Plasma levels of anti-collagen IgG$_{2a}$ at day 9.

| Treatment | Plasma levels (μg/ml) of anti-collagen IgG$_{2a}$ |
| --- | --- |
| Normal | 731.40 ± 30.91 |
| Isotype control (mIgG1) | 100554 ± 25576 |
| hMCP1-mIg | 51738 ± 13880 |

Data were expressed as mean with standard error.

Example 4

Receptor Binding Assay

In this example, the ability of hMCP1 (R & D Systems) and hMCP1-mIg (SEQ ID NO: 8) to bind the CCR2 receptor was assayed.

'Full-length human CCR2 cDNA (Genbank Accession No. NM_000648) was generated from human peripheral blood mononuclear cells by RT-PCR using oligonucleotide sequence derived from a published sequence. Full-length mouse CCR2 cDNA (Genbank Accession No. NM_009915) was also generated from mouse splenocytes by RT-PCR using oligonucleotide sequence derived from a published sequence.

Murine IL-3 dependent pro-B cells Ba/F3 were maintained in RPMI 1640 medium (Invitrogen, Gaithersburg, Md.) supplemented with 10% fetal bovine serum, 2 mM L-glutamine, 100 μg per ml streptomycin, and 100 ug per ml penicillin, 50 μM 2-mercaptoethanol and 2 μg per ml of recombinant mouse IL-3 (Biosource International, Camarillo, Calif.). Recombinant Ba/F3 cells expressing human CCR2 and mouse CCR2 were established by stably transfecting Ba/F3 mouse pre-B cells with pME18Sneo-hCCR2 or mCCR2 plasmids by electroporation with a protocol described in Chou et al. British J. Pharmacology 137:663 (2002). Stable transfectants were selected in the presence of Geneticin (Invitrogen) at 1 mg/ml.

Cell membranes were prepared as previously described in Chou et al., 2002. Briefly, cells were pelleted, resuspended in a lysis buffer (10 mM HEPES, pH 7.5 and Complete® protease inhibitors (Boehringer Mannheim, Indianapolis, Ind.) and incubated on ice for 5 min. The cells were transferred to a 4639 cell disruption bomb (Parr Instrument, Moline, Ill.) and disrupted with 1500 psi nitrogen for 30 min on ice. Following removal of large cellular debris by centrifugation at 500 g for 5 min, cell membranes in the supernatant were pelleted by centrifugation at 100,000 g for 30 min. Membranes were resuspended in lysis buffer containing 10% sucrose and stored at −80° C. Radiolabeled human MCP1 (specific activity=2200 Ci/mmol) was purchased from Perkin-Elmer (Boston, Mass.).

In CCR2 receptor binding assay, the binding reaction was carried out under the following conditions: 50 mM HEPES, 10 mM NaCl, 1 mM CaCl$_2$, 10 mM MgCl$_2$, 0.1% bovine serum albumin, 2 μg cell membrane and 160 μg wheat-germ agglutinin SPA beads (Amersham, Piscataway, N.J.), 30 pM radioiodinated human MCP1, and competing agents at indicated concentrations. The reaction mixtures were incubated at room temperature with constant rocking. Membrane-bound radiolabeled rhMCP1 was measured using a 1450 Microbeta Trilux counter (Wallac, Gaithersburg, Md.). The EC$_{50}$ and the Ki values were calculated using the GraphPad Prism 4 software (San Diego, Calif.).

hMCP1-mIg competed with radiolabeled rhMCP1 in binding to the membranes of cells containing CCR2, with a potency of 5-12 fold less than unlabeled rhMCP1 (Table 5).

TABLE 5

Inhibition of CCR2 binding of radio-iodinated rhMCP1

| | Ba/F3-hCCR2 cells | | Ba/F3-mCCR2 cells | |
| --- | --- | --- | --- | --- |
| | IC$_{50}$ (pM) | K$_i$ (pM) | IC$_{50}$ (pM) | K$_i$ (pM) |
| rhMCP1 | 183.0 | 84.5 | 29.8 | 11.8 |
| hMCP1-mIg | 623.9 | 287.5 | 350.2 | 138.2 |

Example 5

Expression, Purification and Characterization of MCP1-Ig Fusions

In this example, fusions were expressed and purified and characterized.

Variants of hMCP-1-hIg fusion proteins. Human MCP1-hIg variant proteins were expressed in mammalian cells, secreted and then isolated from the cellular growth media. Purification was conducted using the same protocols as set forth above for purifying hMCP-1-mIg. The isolated proteins were analyzed by SDS-PAGE.

The cDNA of human MCP1 (see Genbank accession No. NM 002982) and a partial cDNA derived from the constant region of human immunoglobulin heavy chain gamma 1 isotype (see Genbank accession No. 019046) or gamma 4 isotype (see Genbank accession No. BC025985) (in both cases including the coding sequences for the hinge, the CH2, and the CH3 regions) were cloned by reverse-transcription polymerase chain reaction (RT-PCR). To create monomeric forms of the gamma 1 and gamma 4 variants, the cysteine residues in the hinge region were replaced by serine residues.

The cDNAs corresponding to the hMCP1-hIg variants were individually cloned into mammalian expression vector pcDNA3.1 (+) (Invitrogen, Carlsbad, Calif.) as Hind3-Not1 fragment by standard molecular biology procedures to create the pcDNA3.1(+)hMCP1-hIgG plasmid.

The hMCP-1-hIg variants were expressed by stably transfecting the corresponding plasmids into CHO-K1 cells. The protocols of transfection, selection of stable clones, tissue culture, and product purification were similar to those described in the example of hMCP-1-mIg.

The binding affinities of the hMCP-1-hIg variants to CCR2 receptor were determined using the membranes of THP-1 cells, as in the example of hMCP-1-mIg. The K$_i$ values of the variants were estimated to be 16.8 pM for the dimeric form of hMCP-1-hIg(γ1), 28.8 pM for the monomeric form of hMCP-1-hIg(γ1), 51.9 pM for the dimeric form of hMCP-1-hIg(γ4), and 90.1 pM for the monomeric form of hMCP-1-hIg(γ4). For comparison, the K$_i$ value of hMCP-1 in the same experiment was determined to be 65.7 pM.

The relative potencies of the variants were also determined by chemotaxis assays with THP-1 cells. The protocol was similar to that described in the example of hMCP-1-mIg. The estimated EC$_{50}$ values were 50 pM for the dimeric form of hMCP-1-hIg(γ1), 90 pM for the monomeric form of hMCP-1-hIg(γ1), 500 pM for the dimeric form of hMCP-1-hIg(γ4), and 500 pM for the monomeric form of hMCP-1-hIg(γ4). For comparison, the EC$_{50}$ value of hMCP-1 in the same experiment was determined to be 200-400 pM.

The ability of the hMCP-1-hIg variants to desensitize CCR2 was determined with THP-1 cells by chemotaxis assays. The protocol is similar to that described in the example of hMCP-1-mIg. The cells were incubated with each variant hMCP-1-hIg for 30 minutes prior to test for migration towards hMCP-1. With the pretreatment of either the dimeric or the monomeric forms of hMCP-1-hIg(γ1), at as low as 1 nM of the Ig-fusion proteins, the migration of THP-1 cells was completely abolished. When the cells were preincubated with the dimeric or the monomeric forms of hMCP-1-hIg(γ4) each at 1 nM, the $EC_{50}$ value of hMCP-1 increased by 2-4 fold. When the preincubation was carried out with the dimeric or the monomeric forms of hMCP-1-hIg(γ4) at 10 nM, the $EC_{50}$ value of hMCP-1 increased by 30 fold or more.

Purification of hMCP-1-mIg. For large-scale purification (200 mg and up) of hMCP-1-mIg (used in EAE and anti-collagen antibody-induced arthritis models set forth below), ProA affinity chromatography was employed using the rProA Sepharose FF or the MabSelect resin, from GE Healthcare (Uppsala, Sweden). The affinity column was equilibriated with a high salt buffer consisting of sodium phosphate at 10 mM, pH 7.2, and sodium chloride at 125 mM NaCl. Conditioned medium was loaded to the column followed by a 10 bed-volumes wash with the same buffer as indicated before. The sample-loaded column was then washed with 5 bed-volumes of phosphate buffer including sodium phosphate at 10 mM, pH 7.2. Product elution was carried out with 5 bed-volumes of acetic acid at 0.1 M at pH 2.9. The eluate was immediately neutralized by bringing the pH to 7.2 with Tris Base at 1 M. After the pH adjustment, the pool was filtered with Stericup Express GP Plus 0.22 μm (Millipore, Bedford Mass.).

An optional step of anion-exchange chromatography with Q Sepharose HiTRAP FF (GE Healthcare) was used as needed to remove minor impurities. The equilibration and wash buffer consisted of sodium phosphate at 10 mM, pH 7.2, and sodium chloride at 125 mM NaCl. The product was in the flow-through.

For product concentrating, an Amicon Stir Cell, Model 8050 with 10K regenerated cellulose (Millipore) was used.

Pharmacokinetics of hMCP-1-mIg. C57B6 mice were used for pharmacokinetic studies of hMCP-1-mIg. Mice in groups of three were injected intravenously, intraperitoneally, or subcutaneously with a single dose of hMCP-1-mIg at 10 milligrams per kilogram body weight. Serum samples were collected at time points from 30 minutes to 7 days. The residual levels of hMCP-1-mIg were determined by enzyme-linked immunosorbent assay (ELISA) using anti-hMCP-1 antibody (R&D Systems, Minneapolis, Minn.) as the capture antibody and horse-raddish peroxidase-conjugated anti-mouse IgG1 antibody (Bethyl, Montgomery, Tex.) as the detection antibody. The results indicated a serum half life of 3-5 days. The levels of hMCP-1-mIg remained to be about 10 nM at day 7.

Effect of hMCP-1-mIg on acute and relapsing EAE. Experimental autoimmunine encephalomyelitis (EAE) induction was performed in SJL mice. The mice were immunized on day 0 with 100 μg/mL PLP139-151 peptide (HCLGKWLGHPDKF (SEQ ID NO: 29); Biosynthesis; Lewisville, Tex.) in 2 mg/mL complete Freund's adjuvant (CFA) subcutaneously and 100 ng of pertussis toxin intravenously. Mice were treated on days 3, 5 or on days 3, 5, 7 with 10 milligram per kilogram body weight (mpk) of either an mouse IgG1 isotype-control antibody (SP-Biopharma) or the human MCP-1-mouse Ig (hMCP-1-mIg) fusion protein. Mice were then monitored for body weight and clinical signs of disease. Disease score was recorded as follows: 1=limp tail, 2=hind limb weakness, 3=partial hind limb paralysis, 4=total hind limb paralysis, and 5=moribund.

Cell invasion into the central nervous system was monitored by flow cytometry of cells isolated from the spinal cord. An n=3 of mice were utilized for each group. Mice were perfused with isotonic buffer containing heparin to remove peripheral blood from the CNS. Brain and spinal cord were harvested for CNS mononuclear isolation. Cells were pushed through a wire mesh, incubated with collagenase and dnase to release mononuclear cells. The cell suspension was then centrifuged through a percoll gradient. Cell recovery was determined by trypan blue cell counts and cellular profile was established through FACS analysis. Cells were stained with BD stains conjugated to antibodies against CD45, CD11b (for inflammatory macrophages), and CD4 (for activated T cells), respectively. The antibodies were purchased from BD Biosciences (San Jose, Calif.). The stained cells were analyzed on Facscaliber using cell quest software (BD Biosciences, San Jose, Calif.).

The results as shown in Table 6 indicated a protecting effect of hMCP-1-mIg in the EAE model. The protection appeared to be associated with the reduction of the number of macrophages in the spinal cord.

TABLE 6 hMCP-1-mIg fusion protein treatment inhibits EAE

| Experiment ID | Ave. Onset IgG1 Control | Ave. Onset huMCP-1-Ig fusion protein | Maximum Disease Score IgG1 Control | Maximum Disease Score huMCP-1-Ig fusion protein |
|---|---|---|---|---|
| Experiment A | 11.8 | 12.0 | 5, 4, 2 | 0, 0, 0 |
| Experiment B/C* | 10.0 | 13.5 | 4, 4, 3 | 0, 0, 2 |
| Experiment D | 9.6 | 14.5 | 4, 4, 4, 3 | 0, 0, 2, 3, 3 |
| Average Score-All Experiments | 10.47 | 13.33 | 3.72 | 0.91 |

*Clinical score data was combined for these two studies. Majority of mice were taken preclinically for early mechanistic studies and not included.

TABLE 7 hMCP-1-mIg fusion protein inhibits macrophage invasion into the CNS

| Dosing regime Set 10 mpk | CNS analysis | Treatment | Inflammatory Macrophages* | Activated T cells** |
|---|---|---|---|---|
| A d3, 5 | d5 | hMCP1-mIgG1 | 1.87E+04 | 6.29E+04 |
| | | mIgG1 | 2.25E+04 | 3.76E+04 |
| B d3, 5 | d6 | hMCP1-mIgG1 | 1.75E+04 | 7.26E+05 |
| | | mIgG1 | 4.73E+04 | 4.12E+05 |
| C d3, 5 | d6 | hMCP1-mIgG1 | 1.62E+05 | 6.28E+04 |
| | | mIgG1 | 3.35E+05 | 9.20E+04 |
| D d3, 5, 7 | d12 | hMCP1-mIgG1 | 0.69E+05 | 1.29E+05 |
| | | mIgG1 | 2.36E+05 | 3.72E+05 |

*Inflammatory Macrophage Population defined as CD45hi/CD11b+/CD4−
**Activated T cell Population defined as CD45hi/CD11b−/CD4+

Example 6

Effect of hMCP-1-mIg on Anti-Collagen Antibody-Induced Arthritis

In this example, the ability of hMCP-1-mIg to reduce anti-collagen antibody-induced arthritis was determined.

Antibody induced arthritis was induced by injecting 800 μg of Chemicon's arthrogen CIA antibody (Chemicon, Temecula, Calif.) cocktail intravenously into age matched male B10RIII mice. Prior to this induction, mice were treated with 40 mpk of either isotype control mIgG1 or hMCP-1-mIg fusion protein subcutaneously. Disease onset occurred by day 2 or 3. Animals were scored daily. The scoring system was utilized to measure each paw as follows: 1=one swollen joint, 2=two or more swollen joints, 3=entire foot swelling. Each mouse can receive a maximum disease score of 12. The results obtained are set forth below in Table 8.

TABLE 8

MCP-1 Ig fusion protein inhibits antibody induced arthritis
huMCP-1 Ig FP in antibody induced arthritis
Average Disease Scores

|  | Exp 1 | Exp 2 | Exp 1 | Exp 2 |
|---|---|---|---|---|
|  | IgG1 Control | | huMCP1 Ig FP | |
| day 0 | 0.0 | 0.0 | 0.0 | 0 |
| day 1 | 0.0 | 0.0 | 0.0 | 0 |
| day 2 | 0.5 | 2.0 | 0.0 | 0 |
| day 3 | 1.5 | 3.4 | 0.8 | 0.2 |
| day 4 | 3.3 | 4.0 | 0.8 | 0.6 |
| day 5 | 3.8 | 5.6 | 1.0 | 0.8 |
| day 6 | 5.5 | 5.8 | 1.3 | 0.8 |
| day 7 | 5.3 | 5.6 | 1.3 | 0.8 |

TABLE 8-continued

MCP-1 Ig fusion protein inhibits antibody induced arthritis
huMCP-1 Ig FP in antibody induced arthritis
Average Disease Scores

|  | Exp 1 | Exp 2 | Exp 1 | Exp 2 |
|---|---|---|---|---|
|  | IgG1 Control | | huMCP1 Ig FP | |
| day 8 | 6.0 | 5.6 | 1.3 | 0.8 |
| day 9 | 5.5 | 5.4 | 1.3 | 0.8 |
| day 10 | 5.5 | 5.4 | 1.3 | 0.8 |
| day 11 | 5.3 | 5.0 | 1.3 | 0.8 |
| day 12 | 5.0 | 4.0 | 1.3 | 1.2 |
| day 13 | 4.5 | 2.5 | 1.3 | 1.2 |
| day 14 | 4.0 | 1.5 | 1.3 | 1.2 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

We claim:

1. A method for impeding migration of CCR2-bearing cells into inflammatory tissue, in a subject with atherosclerosis, comprising administering, to the subject, a therapeutically effective amount of an isolated polypeptide comprising a human MCPI polypeptide comprising the amino acid sequence set forth in SEQ ID NO: 2 fused to a human immunoglobulin gamma-1 polypeptide comprising the amino acid sequence set forth in SEQ ID NO: 7.

2. The method of claim 1 wherein the polypeptide comprising the human MCP1 polypeptide and the human immunoglobulin gamma-1 polypeptide comprises one human MCP1 polypeptide fused to one human immunoglobulin gamma-1 polypeptide.

3. The method of claim 2 wherein the polypeptides are fused by a peptide linker.

4. The method of claim 1 wherein the polypeptide comprising the human MCP1 polypeptide and the human immunoglobulin gamma-1 polypeptide is in a pharmaceutical composition comprising a pharmaceutically acceptable carrier.

5. The method of claim 1 wherein the polypeptide comprising the human MCP1 polypeptide and the immunoglobulin gamma-1 polypeptide is administered to the subject in association with one or more further therapeutic agents.

6. The method of claim 5 wherein the further therapeutic agent is a member selected from the group consisting of valdecoxib; triamcinolone acetonide; tolmetin; tiaprofenic acid; tenoxicam; tazarotene; sulindac; sulfasalazine; salicylic acid; rofecoxib; prednicarbate; piroxicam, salsalate; phenylbutazone; petroleum jelly; penicillamine; oxaprozin; oilated oatmeal; naproxen; nabumetone; mycophenolate mofetil; mometasone furoate; metronidazole; methotrexate; mesalamine; meloxicam; mefenamic acid; meclofenamate; lumiracoxib; ketorolac; ketoprofen; isotretinoin; injectable gold; infliximab; indomethacin; ibuprofen; hydroxyurea; hydroxychloroquine; hydrocortisone; halobetasol propionate; halcinonide; gold sodium thiomalate; fluticasone propionate; flurbiprofen; flurandrenolide; fluocinonide; fluocinolone acetonide; floctafenine; fenoprofen; etoricoxib; etodolac; etanercept; epsom salts; efalizumab; diflunisal; diflorasone diacetate; diclofenac; desoximetasone; desonide; Dead Sea salts; cyclosporine; coal tar; clobetasol propionate; ciprofloxacin; chloroquine; celecoxib; calcipotriene; budesonide; betamethasone valerate; betamethasone dipropionate; betamethasone benzoate; azathioprine; aurothioglucose; auranofin; aspirin; anthralin; anakinra; amcinonide; aloe vera; alefacept; alclometasone dipropionate; adalimumab; acitretin; ABX-IL8; a mixture of hydrocortisone, dexamethasone, methylprednisolone and prednisolone; a dietary vitamin B12 supplement; a dietary folate supplement; a dietary calcium supplement; 6-Thioguanine; and 6-mercaptopurine.

7. The method of claim 1 wherein the polypeptide comprising the human MCP1 polypeptide and the human immunoglobulin gamma-1 polypeptide is administered in association with a non-steroidal anti-inflammatory drug or a COX-2 inhibitor.

* * * * *